(12) United States Patent
Mitchell et al.

(10) Patent No.: US 8,461,083 B2
(45) Date of Patent: Jun. 11, 2013

(54) HERBICIDAL COMPOUNDS

(75) Inventors: Glynn Mitchell, Bracknell (GB); David Phillip Bacon, Bracknell (GB); Ian Henry Aspinall, Bracknell (GB); Emma Briggs, Bracknell (GB); Alaric James Avery, Bracknell (GB); James Alan Morris, Bracknell (GB); Claire Janet Russell, Bracknell (GB); Roger Salmon, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 177 days.

(21) Appl. No.: 12/933,640

(22) PCT Filed: Mar. 16, 2009

(86) PCT No.: PCT/GB2009/000713
§ 371 (c)(1),
(2), (4) Date: Sep. 20, 2010

(87) PCT Pub. No.: WO2009/115788
PCT Pub. Date: Sep. 24, 2009

(65) Prior Publication Data
US 2011/0021352 A1    Jan. 27, 2011

(30) Foreign Application Priority Data

Mar. 20, 2008    (GB) .................................. 0805318.3

(51) Int. Cl.
   *A01N 43/40*      (2006.01)
   *A01N 43/42*      (2006.01)
   *A61K 31/44*      (2006.01)

(52) U.S. Cl.
   USPC ............ 504/246; 514/300; 546/122; 546/123

(58) Field of Classification Search
   USPC .................... 504/246; 514/300; 546/122, 123
   See application file for complete search history.

(56) References Cited

U.S. PATENT DOCUMENTS 5,059,240 A * 10/1991 Hagen et al. .................. 504/105
5,723,413 A * 3/1998 Bratz et al. .................... 504/246

FOREIGN PATENT DOCUMENTS

| DE | 4405712 | 8/1995 |
| EP | 387568 | 9/1990 |
| WO | WO9746530 | * 12/1997 |

* cited by examiner

*Primary Examiner* — Jane C Oswecki
(74) *Attorney, Agent, or Firm* — James Cueva

(57) ABSTRACT

The present invention relates to novel herbicidal [1,8]-naphthyridines of Formula (Ia) or (Ib), or an agronomically acceptable salt of said compound wherein $R^2$, $R^3$, $R^4$, $R^5$, $R^6$, $R^7$, $R^8$, n, m, X and Q are as defined herein. The invention further relates to processes and intermediates for the preparation of the [1,8]-naphthyridines, to compositions which comprise the herbicidal compounds, and to their use for controlling weeds, in particular in crops of useful plants.

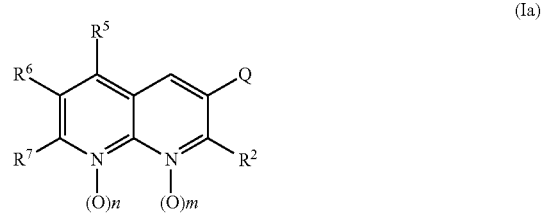

(Ia)

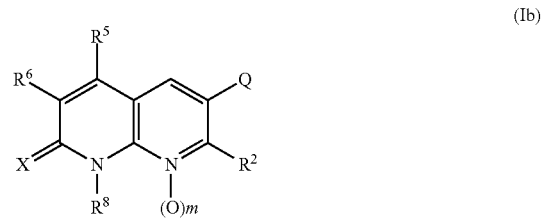

(Ib)

15 Claims, No Drawings

HERBICIDAL COMPOUNDS

This application is a 371 of International Application No. PCT/GB2009/000713 filed Mar. 16, 2009, which claims priority to GB 0805318.3 filed March 20, 2008, the contents of which are incorporated herein by reference.

The present invention relates to novel herbicidal [1,8]-naphthyridines, to processes for their preparation, to compositions which comprise the herbicidal compounds, and to their use for controlling weeds, in particular in crops of useful plants, or for inhibiting plant growth.

According to the present invention there is provided a herbicidal compound of Formula (Ia) or Formula (Ib)

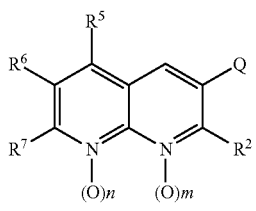
(Ia)

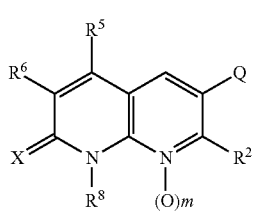
(Ib)

or an agronomically acceptable salt of said compound wherein:—

$R^2$ is selected from the group consisting of $C_1$-$C_3$alkyl, $C_1$-$C_3$haloalkyl, $C_1$-$C_3$alkoxy-$C_1$-$C_3$ alkyl, $C_1$-$C_3$ alkoxy-$C_2$-$C_3$alkoxy-$C_1$-$C_3$-alkyl, $C_1$-$C_3$alkoxy-$C_{1-3}$-haloalkyl, $C_1$-$C_3$-alkoxy-$C_1$-$C_3$-alkoxy-$C_1$-$C_3$-haloalkyl; $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$ alkyl and ($C_1$-$C_3$alkanesulfonyl-$C_3$-$C_4$ cycloalkylamino)-$C_1$-$C_3$ alkyl;

$R^5$ is hydrogen or methyl;

$R^6$ is selected from the group consisting of hydrogen, fluorine, chlorine, hydroxyl and methyl;

$R^7$ is selected from the group consisting of hydrogen, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_3$-$C_6$alkynyl, $C_1$-$C_6$alkoxy, $C_4$-$C_7$cycloalkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, amino, $C_1$-$C_6$alkylamino, $C_2$-$C_6$dialkylamino, $C_2$-$C_6$alkenylamino, $C_1$-$C_6$alkoxy-$C_1$-$C_6$-alkylamino, ($C_1$-$C_6$alkoxy-$C_2$-$C_4$-alkyl)-$C_1$-$C_6$-alkylamino, $C_3$-$C_6$cycloalkylamino, $C_3$-$C_6$cyclohaloalkylamino, $C_1$-$C_3$alkoxy-$C_3$-$C_6$ cycloalkylamino, $C_3$-$C_6$ alkynylamino, dialkylamino in which the substituents join to form a 4-6 membered ring (e.g pyrrolidinyl, piperidinyl) optionally containing oxygen (e.g morpholinyl) and/or optionally substituted by $C_1$-$C_3$-alkoxy and/or halogen especially fluorine, $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$ alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkylenyl-$CO_2$—R', $C_1$-$C_4$alkylenyl-(CO)N—R'R', aryl (e.g. phenyl), phenylthio, phenylsulfinyl, phenylsulfonyl, aryloxy (e.g phenoxy) and 5 or 6-membered heteroaryl or heteroaryloxy, the heteroaryl containing one to three heteroatoms, each independently selected from the group consisting of oxygen, nitrogen and sulphur, wherein the aryl or heteroaryl component may be optionally substituted by a substituent selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

X=O or S;

n=0 or 1;

m=0 or 1 with the proviso that if m=1 then n=0 and if n=1 then m=0;

p=0, 1 or 2;

R' is independently selected from the group consisting of hydrogen and $C_1$-$C_6$alkyl.

$R^8$ is selected from the group consisting of hydrogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkylalkeneyl for example cyclohexylmethylenyl, $C_3$-$C_6$alkynylalkylenyl for example propargyl, $C_2$-$C_6$-alkenylalkylenyl for example allyl, $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with a substituent selected from the group consisting of halo, $C_1$-$C_3$-alkoxy, $C_1$-$C_3$-alkyl, $C_1$-$C_3$ haloalkyl), $C_1$-$C_6$alkoxy $C_1$-$C_6$alkoxy $C_1$-$C_6$alkyl, aryl, 5 or 6-membered heteroaryl, 5 or 6-membered heteroaryl-$C_1$-$C_3$-alkyl or heterocyclyl-$C_1$-$C_3$-alkyl, the heteroaryl or heterocyclyl containing one to three heteroatoms each independently selected from the group consisting of oxygen, nitrogen and sulphur, wherein the aryl, heterocyclyl or heteroaryl component may be optionally substituted by a substituent selected from the group consisting of halo, $C_1$-$C_3$alkyl, $C_1$-$C_3$haloalkyl and $C_1$-$C_3$ alkoxy;

Q is selected from the group consisting of:—

(Q1)

(Q2)

(Q3)

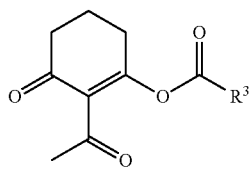
(Q4)

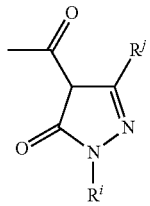
(Q5)

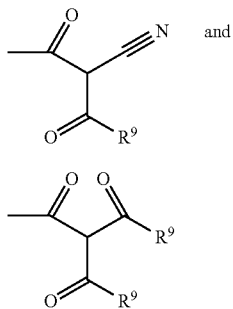
(Q6) and (Q7)

wherein

A¹ is selected from the group consisting of O, C(O), S, SO, SO$_2$ and (CR$^e$R$^f$)$_q$;

q=0, 1 or 2;

R$^a$, R$^b$, R$^c$, R$^d$, R$^e$ and R$^f$ are each independently selected from the group consisting of C$_1$-C$_4$alkyl which may be mono-, di- or tri-substituted by substituents selected from the group consisting of C$_1$-C$_4$alkoxy, halogen, hydroxy, cyano, hydroxycarbonyl, C$_1$-C$_4$alkoxycarbonyl, C$_1$-C$_4$alkylthio, C$_1$-C$_4$alkylsulfinyl, C$_1$-C$_4$alkylsulfonyl, C$_1$-C$_4$alkylcarbonyl, phenyl and heteroaryl, it being possible for the phenyl and heteroaryl groups in turn to be mono-, di- or tri-substituted by substituents selected from the group consisting of C$_1$-C$_4$alkoxy, halogen, hydroxy, cyano, hydroxycarbonyl, C$_1$-C$_4$alkoxycarbonyl, C$_1$-C$_4$alkylsulfonyl and C$_1$-C$_4$haloalkyl, the substituents on the nitrogen in the heterocyclic ring being other than halogen; or R$^a$, R$^b$, R$^c$, R$^d$, R$^e$ and R$^f$ are each independently selected from the group consisting of hydrogen, C$_1$-C$_4$alkoxy, halogen, hydroxy, cyano, hydroxycarbonyl, C$_1$-C$_4$alkoxycarbonyl, C$_1$-C$_4$alkylsulfinyl, C$_1$-C$_4$alkylsulfonyl, C$_1$-C$_4$alkylcarbonyl, phenyl or heteroaryl, it being possible for the phenyl and heteroaryl groups in turn to be mono-, di- or tri-substituted by substituents selected from the group consisting of C$_1$-C$_4$alkoxy, halogen, hydroxy, cyano, hydroxycarbonyl, C$_1$-C$_4$alkoxycarbonyl, C$_1$-C$_4$alkylsulfonyl and C$_1$-C$_4$haloalkyl, the substituents on the nitrogen in the heterocyclic ring being other than halogen; or R$^a$ and R$^b$ together form a 3- to 5-membered carbocyclic ring which may be substituted by C$_1$-C$_4$alkyl and may be interrupted by oxygen, sulfur, S(O), SO$_2$, OC(O), NR$^g$ or by C(O); or R$^a$ and R$^c$ together form a C$_1$-C$_3$alkylene chain which may be interrupted by oxygen, sulfur, SO, SO$_2$, OC(O), NR$^h$ or by C(O); it being possible for that C$_1$-C$_3$alkylene chain in turn to be substituted by C$_1$-C$_4$alkyl;

R$^g$ and R$^h$ are each independently of the other C$_1$-C$_4$alkyl, C$_1$-C$_4$haloalkyl, C$_1$-C$_4$alkylsulfonyl, C$_1$-C$_4$alkylcarbonyl or C$_1$-C$_4$alkoxycarbonyl;

R$^i$ is C$_1$-C$_4$alkyl;

R$^j$ is selected from the group consisting of hydrogen, C$_1$-C$_4$ alkyl and C$_3$-C$_6$ cycloalkyl. In a preferred embodiment R$^j$ is selected from the group consisting of hydrogen, methyl and cyclopropyl.

R$^3$ is selected from the group consisting of C$_1$-C$_6$alkyl, optionally substituted with halogen and/or C$_1$-C$_3$alkoxy; and C$_3$-C$_6$ cycloalkyl optionally substituted with halogen and/or C$_1$-C$_3$alkoxy.

R$^9$ is selected from the group consisting of cyclopropyl, CF$_3$ and i.-Pr,

R$^{10}$ is selected from the group consisting of hydrogen, I, Br, SR$^{11}$, S(O)R$^{11}$, S(O)$_2$R$^{11}$ and CO$_2$R$^{11}$.

R$^{11}$ is C$_{1-4}$ alkyl.

Halogen is, generally, fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Suitable alkylenyl radicals include, for example CH$_2$, CHCH$_3$, C(CH$_3$)$_2$, CH$_2$CHCH$_3$, CH$_2$CH(C$_2$H$_5$).

Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Preferred C$_2$-C$_6$alkenyl radicals substituted once, twice or three times by halogen are those having a chain length of from 2 to 5 carbon atoms. Suitable haloalkylalkynyl radicals include, for example, alkylalkynyl groups substituted one or more times by halogen, halogen being bromine or iodine and, especially, fluorine or chlorine, for example 3-fluoropropynyl, 5-chloropent-2-yn-1-yl, 5-bromopent-2-yn-1-yl, 3,3,3-trifluoropropynyl and 4,4,4-trifluoro-but-2-yn-1-yl.

Preferred alkylalkynyl groups substituted one or more times by halogen are those having a chain length of from 3 to 5 carbon atoms.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl, preferably methoxycarbonyl, ethoxycarbonyl or tert-butoxycarbonyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Cycloalkylamino or dicycloalkylamino is, for example cyclohexyl or dicyclopropylamino.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 6 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

Cycloalkyl groups preferably have from 3 to 6 ring carbon atoms and may be substituted by one or more methyl groups; they are preferably unsubstituted, for example cyclopropyl, cyclobutyl, cyclopentyl or cyclohexyl.

Phenyl, including phenyl as part of a substituent such as phenoxy, benzyl, benzyloxy, benzoyl, phenylthio, phenylalkyl, phenoxyalkyl or tosyl, may be in mono- or poly-substituted form, in which case the substituents may, as desired, be in the ortho-, meta- and/or para-position(s).

Heterocyclyl, for example, includes morpholinyl, tetrahydrofuryl.

Heteroaryl, including heteroaryl as part of a substituent such as heteroaryloxy, means a five or six member heteroaryl containing one to three heteroatoms, each independently selected from the group consisting of oxygen, nitrogen and sulphur. It should be understood that the heteroaryl component may be optionally mono or poly substituted. The term heteroaryl thus includes, for example, furanyl, thiopheneyl, thiazolyl, oxazolyl, isoxazolyl, thiazolyl, pyrazolyl, isothiazolyl, pyridyl, pyridazinyl, pyrazinyl, pyrimidinyl, triazolyl.

Compounds of Formula Ia or Ib may contain asymmetric centres and may be present as a single enantiomer, pairs of enantiomers in any proportion or, where more than one asymmetric centre are present, contain diastereoisomers in all possible ratios.

Typically one of the enantiomers has enhanced biological activity compared to the other possibilities.

Similarly, where there are disubstituted alkenes, these may be present in E or Z form or as mixtures of both in any proportion.

Compounds of Formula Ia where $R^7$ is hydroxyl may be in equilibrium with an alternative tautomeric form, for example in compounds of Formula 1b where $R^8$ is hydrogen. Similarly, Q1, Q5, Q6 or Q7 may be in equilibrium with alternative hydroxyl tautomeric forms. It should be appreciated that all tautomeric forms (single tautomer or mixtures thereof), racemic mixtures and single isomers are included within the scope of the present invention.

The skilled person will also appreciate that if n and/or m is 1 with regard to Formula Ia or Ib to form the N-oxide then the nitrogen and oxygen will be charged accordingly ($N^+O^-$).

In a preferred embodiment the herbicidal compound is of Formula Iaa.

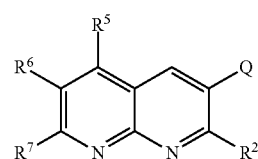

Iaa

In a more preferred embodiment of the present invention Q is Q1, in particular wherein $A^1$ is $CR^eR^f$ and wherein $R^a$, $R^b$, $R^c$, $R^d$, $R^e$ and $R^f$ are hydrogen, and wherein q=1.

In another preferred embodiment of the present invention Q is Q1, wherein $A^1$ is $CR^eR^f$ and wherein, $R^b$, $R^d$, $R^e$ and $R^f$ are hydrogen, $R^a$ and $R^c$ together form an ethylene chain and wherein q=1

In another preferred embodiment $R^2$ is (i) haloalkyl, in particularly fluoroalkyl, and most preferably difluoromethyl or trifluoromethyl, or (ii) $C_{1-3}$alkoxy-$C_{1-3}$-haloalkyl, in particular $C_{1-3}$alkoxy-$C_{1-3}$-fluoroalkyl, most preferably methoxydifluoromethyl or 2-methoxy-1,1-difluoroethyl.

In another preferred embodiment $R^5$ is hydrogen.

In another preferred embodiment $R^6$ is hydrogen or fluorine.

In another preferred embodiment $R^7$ is selected from the group consisting of hydrogen, hydroxyl, halogen, $C_1$-$C_6$alkyl, $C_3$-$C_6$cycloalkyl, $C_1$-$C_6$haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl, $C_1$-$C_6$-alkoxy-$C_2$-$C_6$-alkoxy-$C_1$-$C_6$ alkyl, $C_1$-$C_6$alkylamino, $C_1$-$C_6$dialkylamino, $C_2$-$C_6$alkenylamino, $C_1$-$C_6$alkoxy-$C_2$-$C_3$-alkylamino, ($C_1$-$C_6$alkoxy-$C_2$-$C_3$-alkyl)-$C_1$-$C_3$-alkylamino, $C_3$-$C_6$ cycloalkylamino, $C_3$-$C_6$ cyclohaloalkylamino, $C_1$-$C_3$alkoxy-$C_3$-$C_6$cycloalkylamino, $C_3$-$C_6$ alkynylamino and a dialkylamino group in which the substituents join to form a 4-6 membered ring, optionally containing oxygen, or optionally substituted by $C_1$-$C_3$-alkoxy or halogen, especially fluorine. In an even more preferred embodiment $R^7$ is selected from the group consisting of hydrogen, methyl, ethyl, 1-methylethyl, cyclopropyl, fluoromethyl, difluoromethyl, trifluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, methoxyethyl, ethoxyethoxy, ethoxyethoxymethyl, methoxyethoxy, methoxyethoxymethyl, (2-methoxyethyl)amino and (2-methoxyethyl)methylamino.

In another preferred embodiment $R^8$ is selected from the group consisting of hydrogen, $C_1$-$C_6$alkyl, $C_1$-$C_3$alkoxy$C_1$-$C_3$alkylenyl and $C_1$-$C_6$haloalkyl.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (Ia) or (Ib) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

For the avoidance of doubt, reference to compounds of Formula I below includes reference to compounds of either Formula (Ia) and (Ib).

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+fluorochloridone, I+fluoroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl) phenoxy]-2-pyridyloxy]acetic acid ethyl ester (CAS RN 353292-31-6), I+4-hydroxy-3-[[2[(2-methoxyethoxy)methyl]-6-(trifluoro-methyl)-3-pyridinyl]carbonyl]-bicyclo [3.2.1]oct-3-en-2-one (CAS RN 352010-68-5), and I+4-hydroxy-3-[[2-(3-methoxypropyl)-6-(difluoromethyl)-3-pyridinyl]carbonyl]-bicyclo[3.2.1]oct-3-en-2-one. The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners.

Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, and N-isopropyl-4-(2-methoxy-benzoyl-sulfamoyl)-benzamide (CAS RN 221668-34-4). Particularly preferred are mixtures of a compound of Formula I with cyprosulfamide, isoxadifen-ethyl and/or cloquintocet-mexyl.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf. Maize is particularly preferred.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared using the following methods.

The preparation of compounds Formula I(a) or I(b)

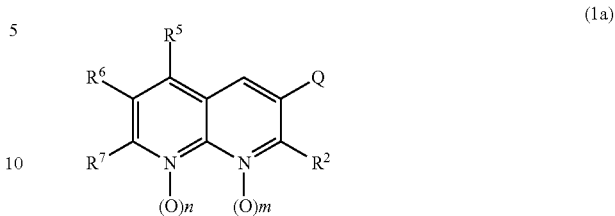

(1a)

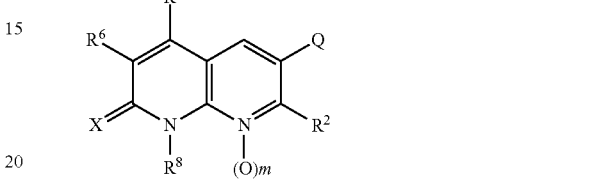

(1b)

where Q is selected from Q1 and Q5 is carried out analogously to known processes (for example those described in WO97/46530, EP0353187 and U.S. Pat. No. 6,498,125) and comprises reacting a compound of the Formula 2a or 2b

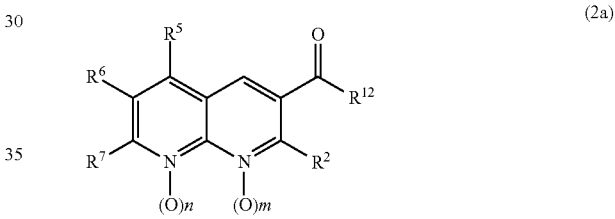

(2a)

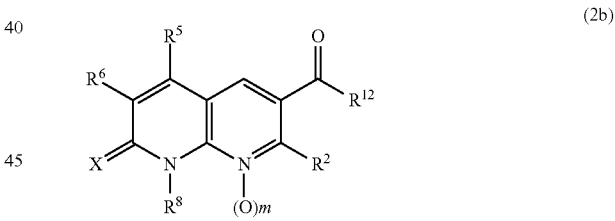

(2b)

where Formula 2a and Formula 2b retain the definitions $R^2$, $R^5$, $R^6$, $R^7$, $R^8$, X, n and m of Formulae 1a and 1b and $R^{12}$ is a suitable leaving group, for example a halogen atom, such as chlorine, or an alkoxy or aryloxy group, such as 4-nitrophenoxy, in an inert organic solvent, such as dichloromethane or acetonitrile, in the presence of a base, such as triethylamine, with compounds

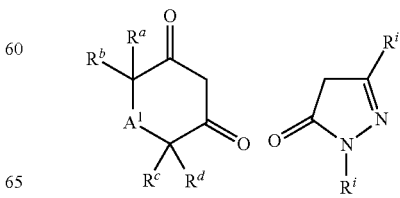

wherein

A$^1$ and R$^a$, R$^b$, R$^c$, R$^d$, R$^e$, R$^f$ and R$^i$ are as defined previously;

to give compounds of the Formula 3a, 3b, 4a, 4b

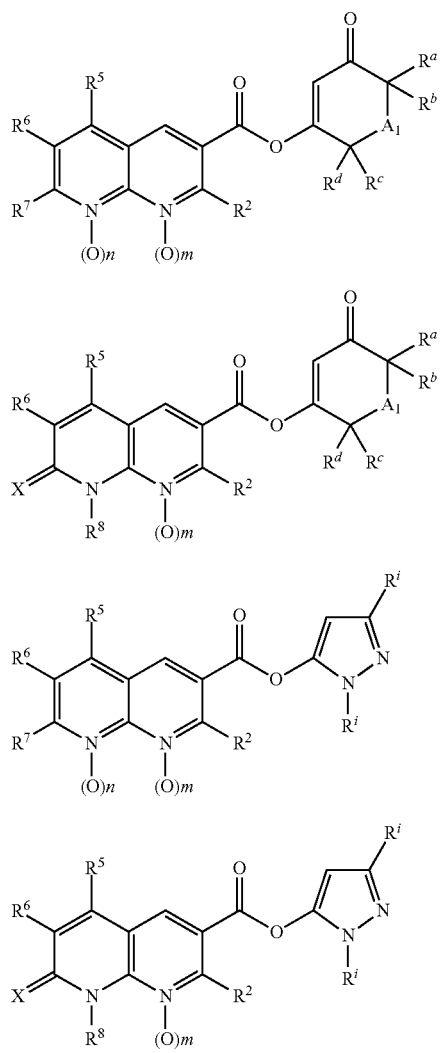

(3a)

(3b)

(4a)

(4b)

where Formulae 3a, 3b, 4a, 4b retain the definitions of Formula 2a and 2b.

Alternatively, esters 3a, 3b, 4a, 4b may be produced from compounds of Formula 2a, 2b where R$^{12}$ is a leaving group produced by reacting a carboxylic acid of Formula 2a, 2b where R$^{12}$ is hydroxy with an activating reagent, such as N,N'-dicyclohexylcarbodiimide, in a suitable solvent, such as acetonitrile.

Esters 3a, 3b, 4a, 4b may be rearranged using catalysts, such as 4-dimethylaminopyridine, or acetone cyanhydrin, or a metal cyanide salt, such as sodium cyanide, in the presence of a suitable base, such as triethylamine, to give compounds of Formula 1a or 1b. It is advantageous to have a dehydrating agent, such as molecular sieves, present in the reaction medium to ensure any water initially present in the solvent or associated with the other components of the reaction mixture is prevented from causing any unwanted hydrolysis of intermediates.

Scheme 1

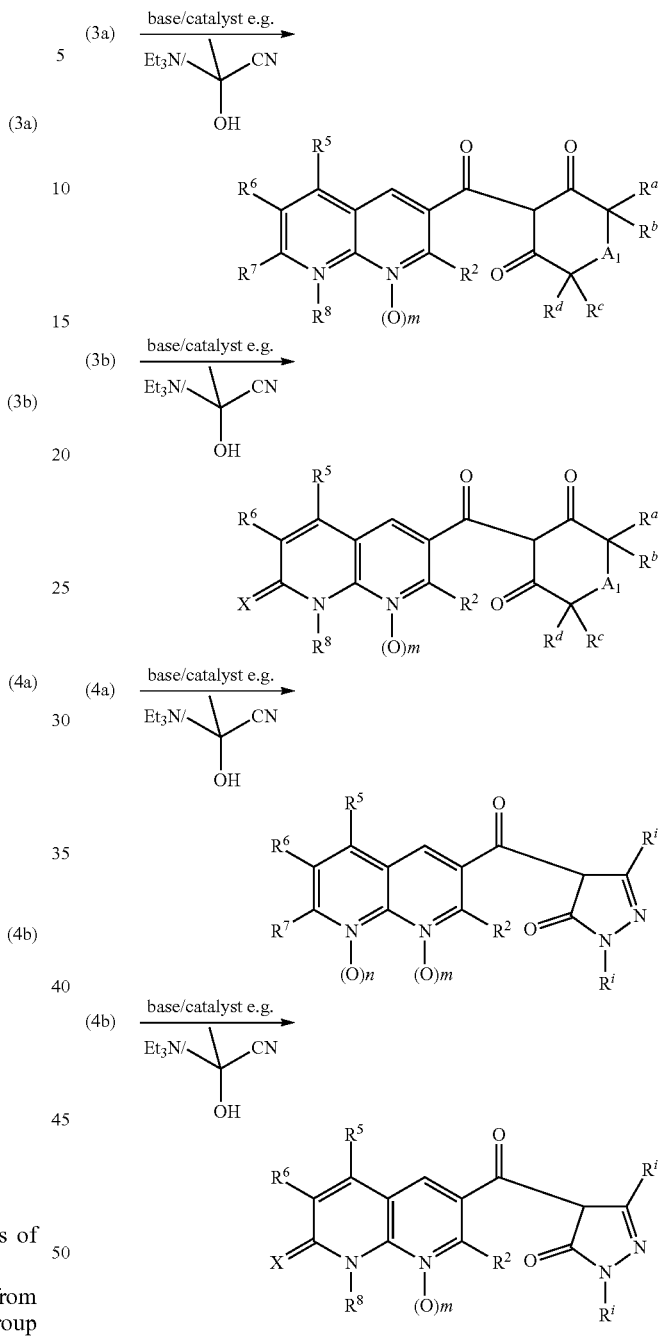

[1,8]Naphthyridine-3-carboxylic acid derivatives of Formula 2a or 2b may be prepared from carboxylic acids, for example by reaction with a suitable halogenating agent, such as oxalyl chloride, in a suitable inert solvent, such as dichloromethane, to generate the corresponding carboxylic acid chlorides. These derivatives may in turn be reacted with, for example, 4-nitrophenol and a suitable base, such as triethylamine, in an inert solvent, such as dichloromethane, to generate the corresponding 4-nitrophenyl esters.

By way of illustration as shown in Scheme 2, [1,8]naphthyridine-3-carboxylic acid esters of Formula 5a may be obtained from 2-amino-3-formylpyridines, analogous to methods described in the literature [*J. Org. Chem.* 1990, 55, 4744-4750; *Indian Journal of Chemistry, Section B; Organic Chemistry including Medicinal Chemistry* (2006), 45B (4), 1051-1053; *Indian Journal of Chemistry, Section B; Organic Chemistry including Medicinal Chemistry* (2004), 43B (4), 897-900; *J. Org. Chem.* (1993), 58 (24), 6625-6628; *J. Chem. Soc. Org.* (1966), (3), 315-321].

Scheme 2

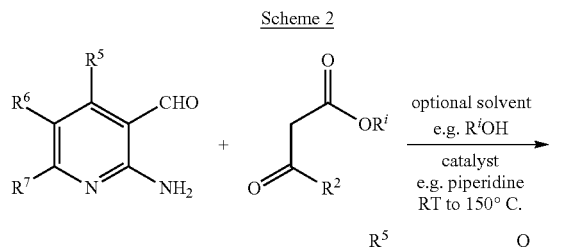

The required β-ketoesters are either commercially available or may be prepared analogously to methods described in the literature.

The required 2-amino-3-formyl pyridines are either commercially available or may be prepared by methods described in the literature [for example *J. Org. Chem.* 1983, 48, 3401-3408 and *J. Org. Chem.* 1990, 55, 4744-4750] or by analogous methods. By way of illustration as shown in Scheme 3, optionally substituted 2-aminopyridines may be N-acylated, for example with a suitable acylating reagent, such as acetyl chloride or pivaloyl chloride, and a suitable base, such as triethylamine, optionally with a suitable acylation catalyst such as 4-dimethylaminopyridine, in an inert solvent, such as dichloromethane, to give the corresponding N-(pyridin-2-yl)amides. Analogous to methods described in the literature, these amides may in turn be reacted with a strong base, such as t.butyl lithium and then a formyl transfer agent, such as N,N-dimethylformamide or N-formyl-N-methylaniline, to give the corresponding N-(3-formylpyridin-2-yl)amides. The required 2-amino-3-formylpyridines can be obtained by hydrolysis of these amides using, for example, aqueous hydrochloric acid heated under reflux for 1 to 24 hours.

Scheme 3

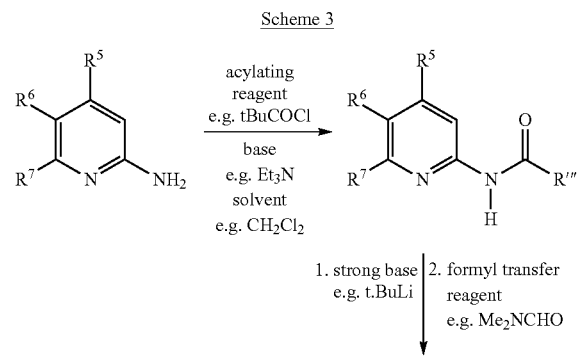

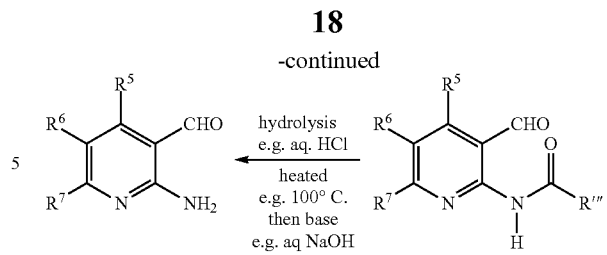

With regard to scheme 3, R''' is for example, $C_1$-$C_6$ alkyl.

In another aspect, as shown in Scheme 4, 2-amino-3-formylpyridines may be further transformed into 2-amino-3-formyl-5-halopyridines using a halogenating agent, such as N-bromosuccinimide, in a suitable solvent, such as acetonitrile. Such 2-amino-3-formyl-5-halopyridines can be used to prepare naphthyridines (as shown in Scheme 2).

Scheme 4

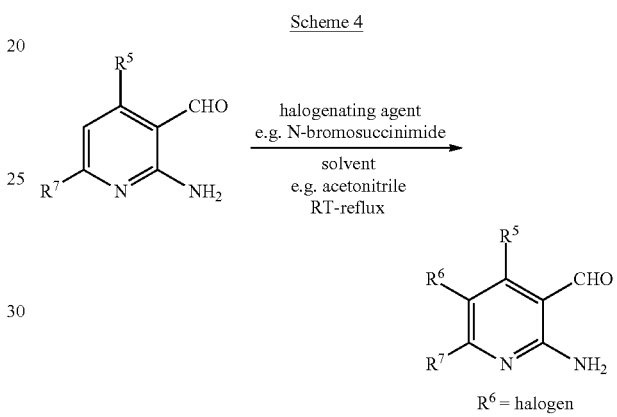

As shown in Scheme 5, [1,8]naphthyridine-3-carboxylic acid esters of Formula 5a may be conveniently hydrolysed to the corresponding carboxylic acids using standard procedures, for example using aqueous sodium hydroxide and an inert co-solvent such as ethanol, or lithium hydroxide in aqueous tetrahydrofuran.

Scheme 5

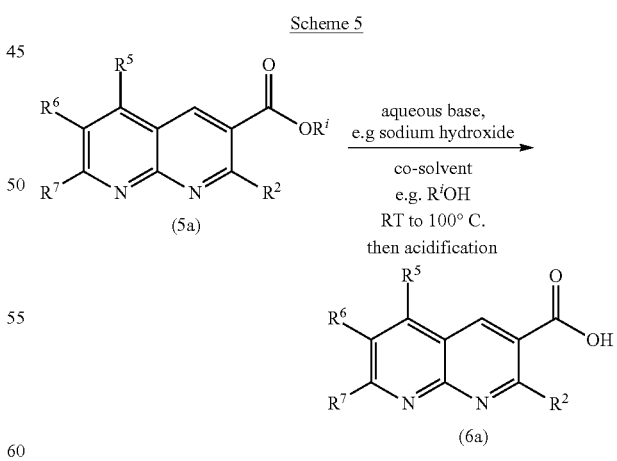

As shown in Scheme 6, [1,8]naphthyridine-3-carboxylic acid esters of Formula 5a may be conveniently converted to the corresponding 8-oxides using a suitable oxidant such as a peracid, for example per-trifluoroacetic acid generated from urea hydrogen peroxide complex and trifluoroacetic acid anhydride.

The 8-oxides generated may be further reacted with a suitable acid halide reagent, such as phosphoryl chloride, optionally with a suitable base, such as triethylamine, in a suitable solvent, such as dichloromethane or 1,2-dichloroethane, at 20° C. to 100° C. to give the 7-halo or 5-halo derivatives or a mixture of both halogen regioisomers depending on the reaction conditions.

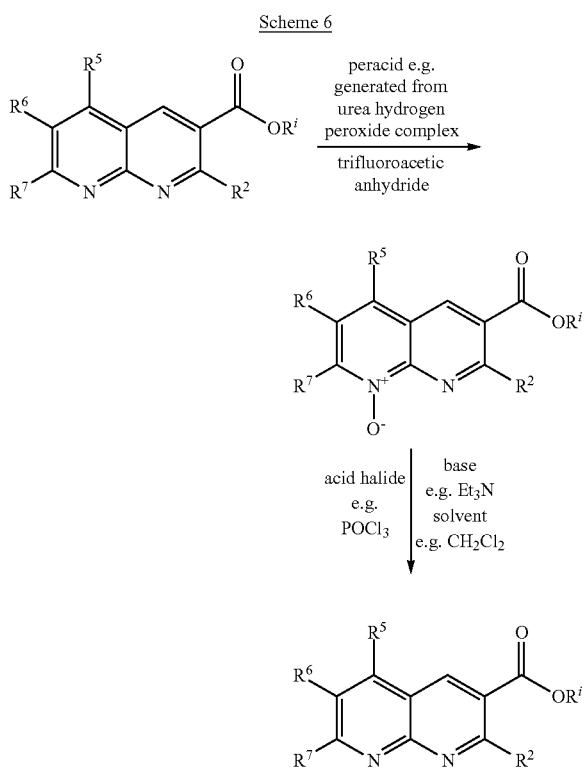

With regard to scheme 6, $R^i$ is, for example, $C_1$-$C_4$ alkyl.

As shown in Scheme 7, 5-halo-[1,8]naphthyridines and 7-halo[1,8]naphthyridines may be further transformed into additional naphthyridines useful for preparing compounds of Formula 1a or 1b. For example, when $R^5$ is hydrogen or methyl and $R^7$ is a chlorine atom, the chlorine may be displaced by an alkoxide reagent, such as sodium ethoxide, in a suitable solvent, such as tetrahydrofuran or N,N-dimethylformamide or an alcohol, such as ethanol, to generate the corresponding 7-alkoxy[1,8]naphthyridine. Similarly, 7-halo[1,8]naphthyridines may be reacted with an amine, such as morpholine, in a suitable solvent, such as tetrahydrofuran, to generate the corresponding 7-alkylamino[1,8] naphthyridine or 7-dialkylamino[1,8]naphthyridine. Additionally, 5-halo- or 7-halo-[1,8]naphthyridines, such as 7-chloro[1,8]naphthyridines, and 5-alkoxy- or 7-alkoxy- [1,8]naphthyridines, such as 7-ethoxy[1,8]naphthyridines, may be converted to 5-hydroxy- or 7-hydroxy-[1,8]naphthyridines, for example by hydrolysis under acidic conditions, such as heating with aqueous hydrochloric acid. Such reactions may be conducted at temperatures from 20° C. to 150° C., for example in a microwave oven.

Additionally, 5-hydroxy or 7-hydroxy[1,8]naphthyridines may be transformed to the corresponding haloalkanesulfonate esters of [1,8]naphthyridines, such as 7-trifluoromethanesulfonyloxy[1,8]naphthyridines, with a suitable acylation agent, such as trifluoromethane sulfonic anhydride, and a suitable base, such as triethylamine, in a suitable solvent, such as dichloromethane.

In another aspect, 5-halo or 7-halo[1,8]naphthyridines, such as 7-chloro[1,8]naphthyridines, or 5- or 7-haloalkanesulfonate esters of [1,8]naphthyridines, such as 7-trifluoromethanesulfonyloxy[1,8]naphthyridines, may be reacted with a boronic acid reagent, such as methyl boronic acid, in the presence of a palladium catalyst, such as palladium acetate, and a suitable base such as potassium phosphate and a suitable palladium ligand, such as dicyclohexyl-(2',6'-dimethoxybiphenyl-2-yl) phosphane, to generate 5-alkyl or 7-alkyl[1,8]naphthyridine derivatives.

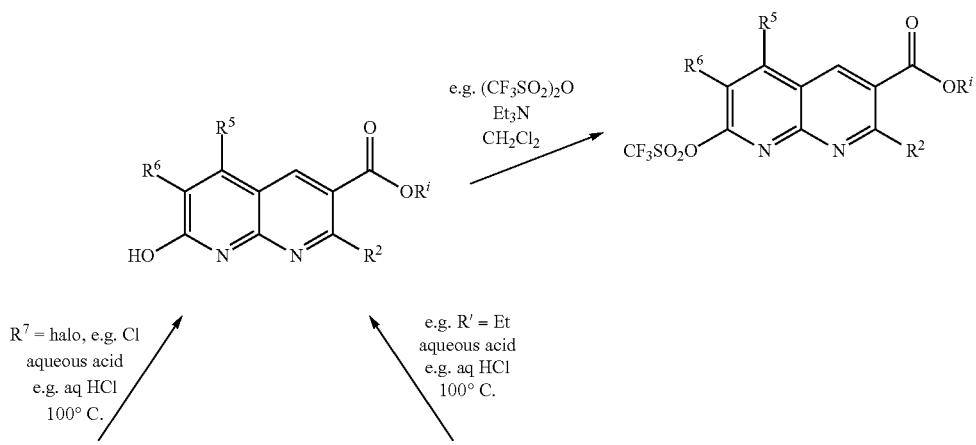

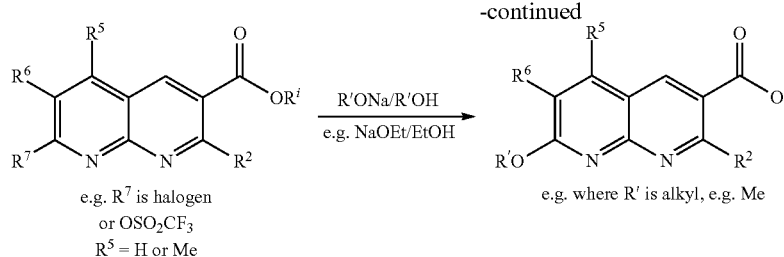

e.g. $R^7$ is halogen or $OSO_2CF_3$
$R^5$ = H or Me e.g. where R' is alkyl, e.g. Me

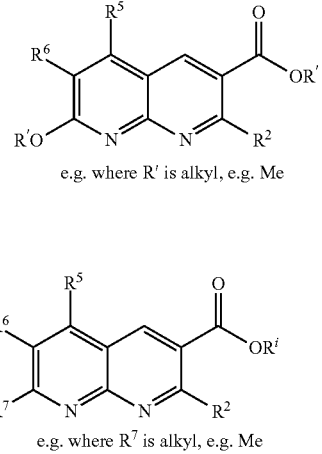

X = amine e.g. morpholine

Pd catalyst/base
$R^7B(OH)_2$
e.g. $MeB(OH)_2$
SPhos
$Pd(OAc)_2$
$K_3PO_4$ e.g. where $R^7$ is alkyl, e.g. Me

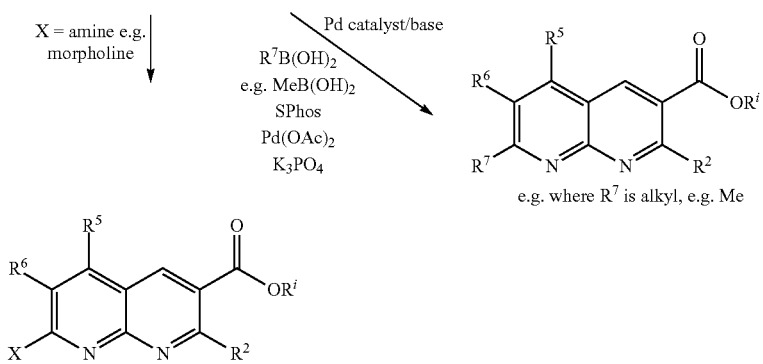

In another aspect as shown in Scheme 8, [1,8]naphthyridine esters in which $R^7$ is hydrogen may be reacted with an alkyl α-ketoacid, such as pyruvic acid, under catalysis by silver (I) salts, such as silver nitrate, in the presence of an oxidant, such as ammonium persulfate, and an acid, such as trifluoroacetic acid or sulfuric acid, in water and an inert co-solvent, such as dichloromethane, to generate 7-alkylcarbonyl[1,8]naphthyridine esters.

Scheme 8

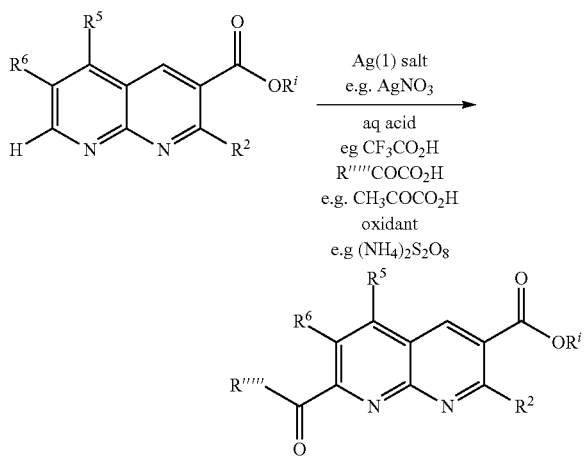

With regard to Scheme 8, R'''' is, for example, $C_1$-$C_5$ alkyl or $C_1$-$C_3$alkoxy-$C_1$-$C_5$-alkyl.

Alternatively as shown in Scheme 9, 7-acetyl[1,8]naphthyridines may be produced by reacting 7-halo[1,8]naphthyridines or 7-trifluoromethanesulfonyloxy[1,8] naphthyridines with a suitable organotin reagent, such as (1-ethoxyvinyl)tributylstannane, in the presence of a palladium catalyst, such as bis-(triphenylphosphine)palladium dichloride, heated in a suitable solvent, such as toluene, to generate the corresponding 7-(1-alkoxyvinyl)-[1,8]naphthyridines. 7-(1-Alkoxyvinyl)-[1,8]naphthyridines when treated with a suitable acid, such as aqueous hydrochloric acid, provide the corresponding 7-acetyl[1,8]naphthyridines.

Scheme 9

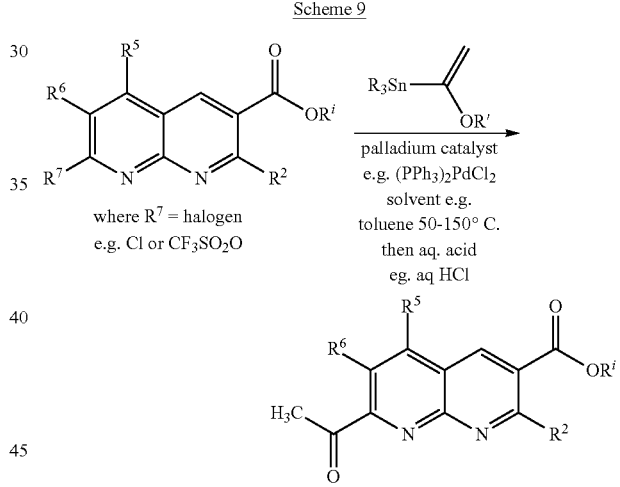

With regard to Scheme 9, $R^i$ is, for example, $C_1$-$C_4$ alkyl and R' is, for example, $C_1$-$C_6$ alkyl.

As shown in Scheme 10, 7-alkylcarbonyl[1,8]naphthyridines may be treated with a suitable fluorinating agent, such as diethylaminosulfur trifluoride, in a suitable inert solvent, such as dichloromethane, to provide 7(1,1-difluoroalkyl)[1,8]naphthyridines. Alternatively, 7-alkylcarbonyl-[1,8] naphthyridines may be reacted with an organometallic reagent, such as methyl magnesium chloride, in an inert solvent, such as tetrahydrofuran, to generate 7(1-alkyl-1-hydroxyalkyl)-[1,8]naphthyridines.

In another aspect, 7-alkylcarbonyl-[1,8]naphthyridines may be reduced with a suitable reducing agent, such as sodium borohydride, in a suitable solvent, such as ethanol, to provide 7-(1-hydroxyalkyl)[1,8]naphthyridines.

Both 7(1-hydroxyalkyl)[1,8]naphthyridines and 7(1-alkyl-1-hydroxyalkyl)[1,8]naphthyridines may be treated with a suitable fluorinating agent, such as diethylaminosulfur trifluoride, to provide 7-(1-fluoroalkyl)[1,8]naphthyridines and 7-(1-alkyl-1-fluoroalkyl)[1,8]naphthyridines respectively.

Scheme 10

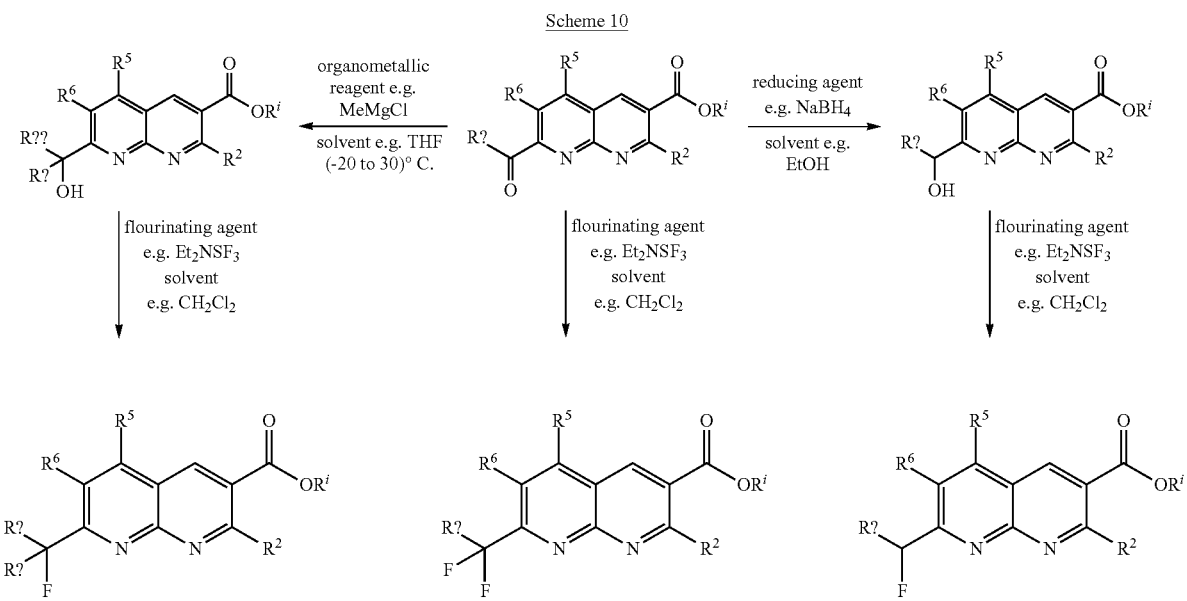

With regard to Scheme 10, R? and R?? are, for example, independently hydrogen or $C_1$-$C_4$ alkyl.

Using processes known to those skilled in the art as shown in Scheme 11, a compound where $R^6$ is halogen, such as bromine, may be transformed to a compound where $R^6$ is amino, using an amino transfer reagent, such as dibenzophenone imine, and a suitable palladium catalyst, such as palladium acetate, and a suitable palladium ligand, such as 4,5-bis-(diphenylphosphoranyl)-9,9-dimethyl-9H-xanthene, with a suitable base, such as cesium carbonate.

Scheme 11

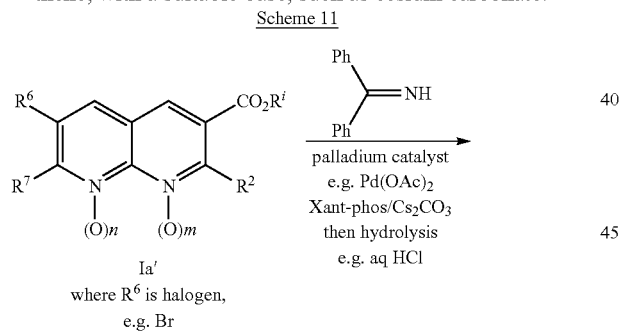

-continued

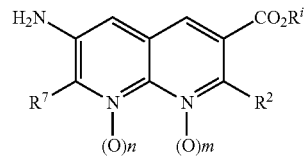

As shown in Scheme 12, 6-amino-[1,8]naphthyridines may be transformed into a 6-fluoro-[1,8]naphthyridine via diazonium salts that are subsequently decomposed to generate the required fluoronaphthyridines either after isolation of the salt or in situ using procedures known to those skilled in the art.

Scheme 12

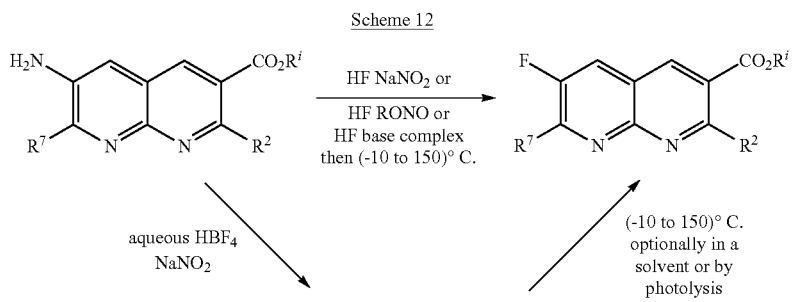

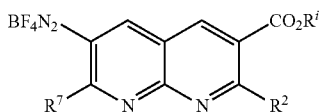

Naphthyridine diazonium salts may be prepared from aminonaphthyridines with sodium nitrite or an alkyl nitrite ester, such as t.-butyl nitrite, in anhydrous or aqueous hydrogen fluoride or hydrogen fluoride-pyridine complex or hydrogen fluoride-triethylamine complex and converting the intermediate diazonium salt or diazoether to the fluoro derivative using procedures known to those skilled in the art, for example by warming the diazo intermediate to its decomposition temperature. Alternatively, the diazonium salt may be fluoro-dediazotised in a suitable reactor using a source of ultra-violet radiation to produce the corresponding 7-fluoro[1,8]naphthyridine. Additionally, compound III in aqueous tetrafluoroboric acid may be treated with an aqueous solution of an alkaline metal nitrite salt, such as sodium nitrite, to generate a diazonium tetrafluoroborate salt that may be isolated, for example by filtration. The dry diazonium salt may be heated directly or in a suitable inert solvent, such as n-octane, toluene or 1,2-dichlorobenzene to decompose the salt to the corresponding 7-fluoro[1,8]naphthyridine.

In another aspect of the invention as shown in Scheme 13, compounds of Formula 1a where $R^7$ is an alkoxy group, such as ethoxy, may be heated, for example using a microwave oven, with an acid, such as hydrochloric acid, and a suitable solvent such as ethanol, at 80-130° C. to generate compounds of Formula 1b where $R^8$ is hydrogen. In solution, 7-hydroxy-[1,8]naphthyridines are in equilibrium with their corresponding 7-oxo-7,8-dihydro[1,8]naphthyridine tautomers. Depending on the reaction conditions employed, these tautomers may be alkylated to give mainly 7-O-alkyl or 8-N-alkyl products or mixtures of both.

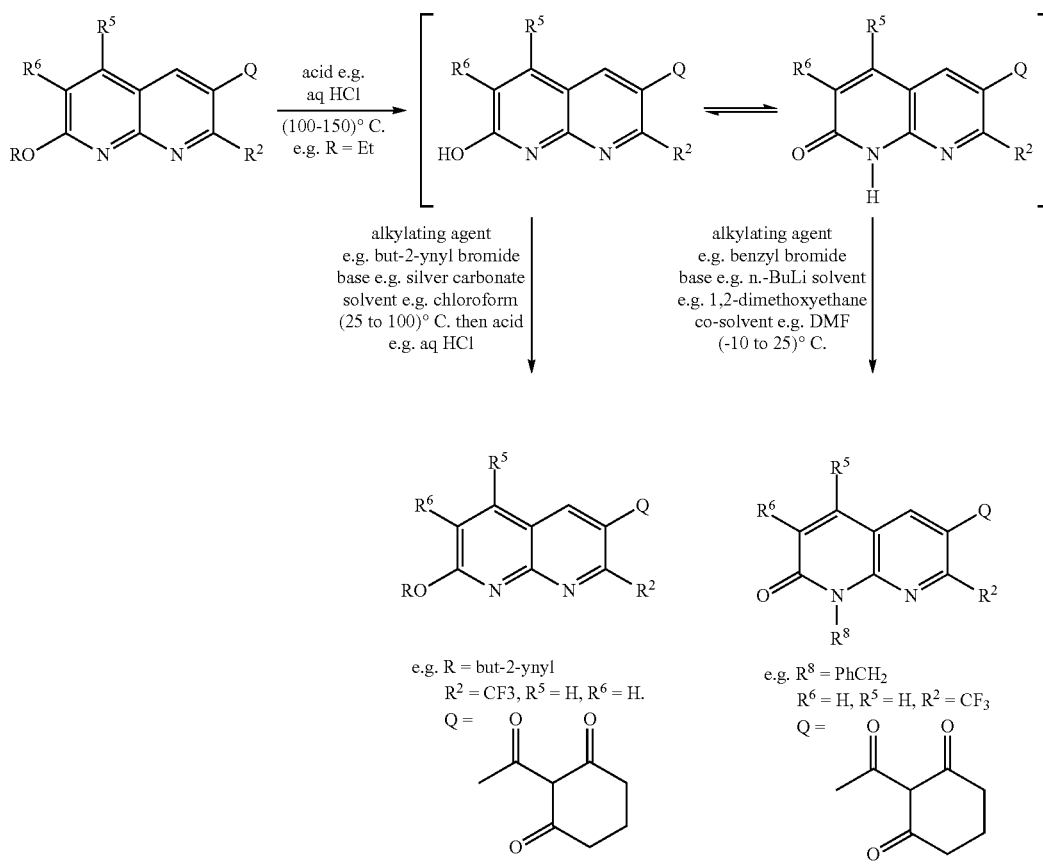

Furthermore, the compounds depicted in Scheme 14 can be obtained as shown. Providing $R^8$ is not hydrogen, the starting compounds may be reacted with a suitable acylation agent, such as isobutyryl chloride, in the presence of a suitable base, such as triethylamine or potassium carbonate, in a suitable inert solvent, such as tetrahydrofuran or dichloromethane, at temperatures from 0° C. to 150° C.

In another aspect of the invention as shown in Scheme 15, compounds of Formula Ia, where Q is Q6 may be obtained by treating compounds of Formula Ia where Q is Q2 or Q3 with a suitable base, such as triethylamine, in an inert solvent, such as dichloromethane or toluene, at 20° C. to 100° C. The salt of the required product obtained is subsequently treated with a suitable acid, such as hydrochloric acid, to provide the corresponding [1,8]naphthyridine cyanodiketone.

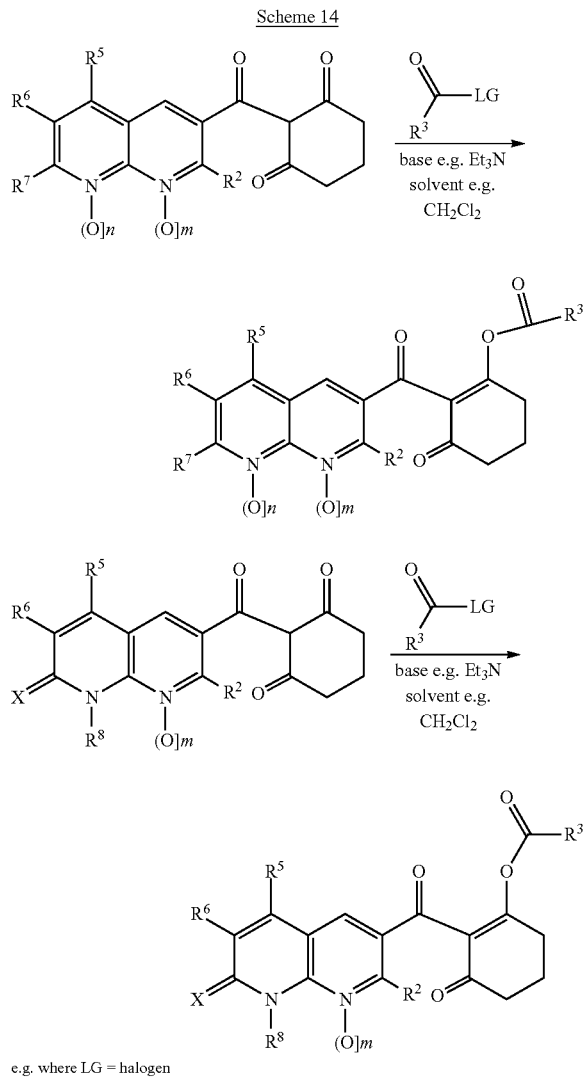

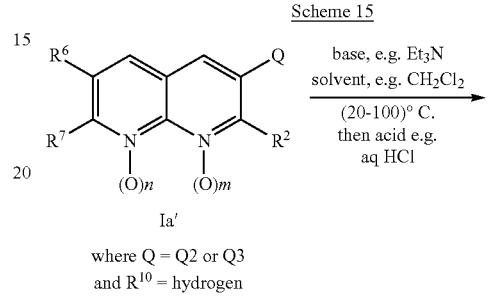

In another aspect of the invention as shown in Scheme 16, a [1,8]naphthyridin-3-yl propan-1,3-dione can be reacted with a N,N-dialkylformamide dialkylacetal reagent, such as N,N-dimethylformamide dimethyl acetal, in a suitable solvent, such as tetrahydrofuran, optionally with an organic acid, such as acetic acid, at temperatures between 20° C. and 150° C. to produce a 2-[1-dialkylaminomethylidene][1,8]naphthyridin-3-ylpropan-1,3-dione. Such a compound can be treated with hydroxylamine in a suitable solvent, such as ethanol, at temperatures from 20° C. to 150° C. to generate compounds as indicated where Q is Q2 or Q3.

[1,8]naphthyridin-3-yl propan-1,3-diones may be prepared by reacting a suitable compound with a t. butyl β-ketoester derivative using procedures analogous to those known to those skilled in the art.

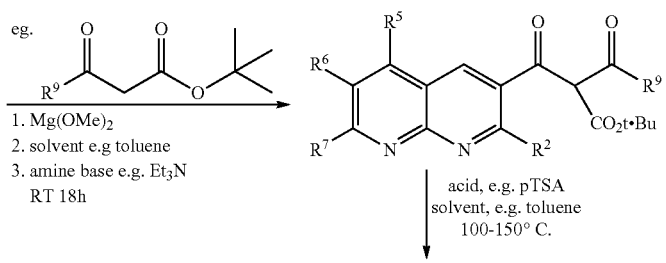

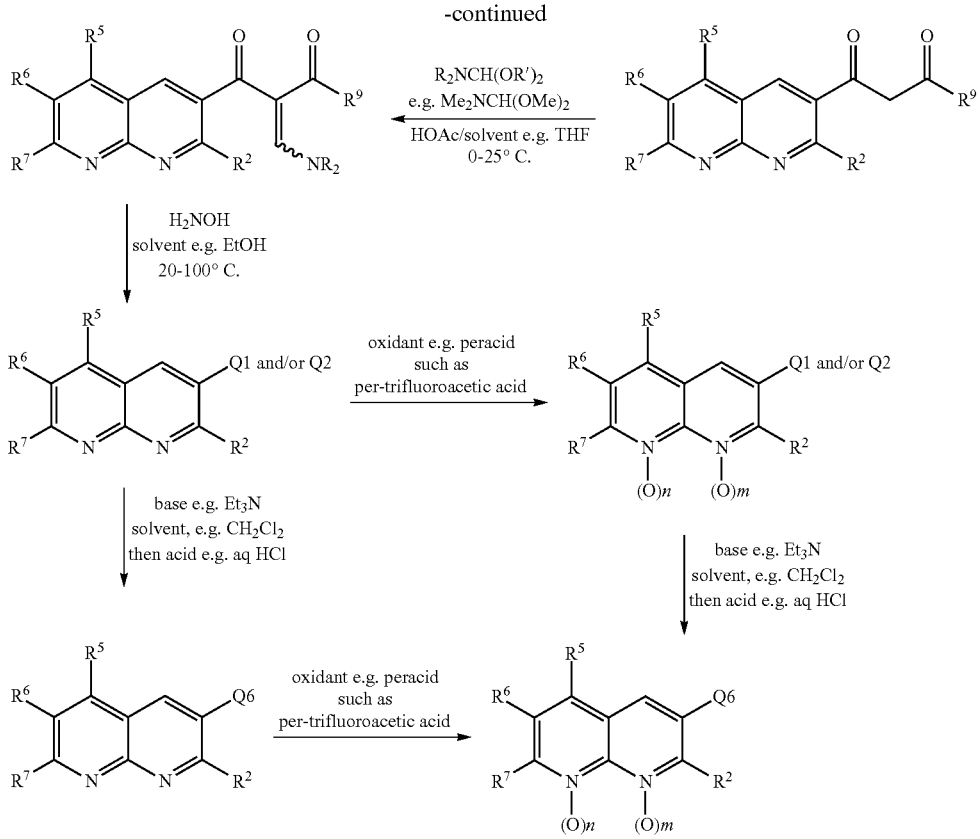

In another aspect of the invention as shown in Scheme 17, a compound of Formula 1a where Q=Q7 may be prepared from a magnesium salt of a [1,8]naphthyridin-3-yl propan-1,3-dione in a suitable solvent, such as tetrahydrofuran, and a suitable acylating agent, such as cyclopropanecarboxylic acid chloride, at temperatures from 25° C. to 100° C. The required [1,8]naphthyridine triketone derivative is obtained by acidification of triketone salt.

Scheme 17

In a further aspect of the invention as shown in Scheme 18, compounds of Formula 1a or 1b where n=m=0 may be oxidised to compounds of Formula 1a or 1b where n or m (but not both) equal 1 using a suitable oxidant such as a peracid, for example pertrifluoroacetic acid generated using urea hydrogen peroxide complex and trifluoroacetic anhydride, to produce compounds of Formula 1a or 1b, where n or m (but not both) equal 1.

Scheme 18

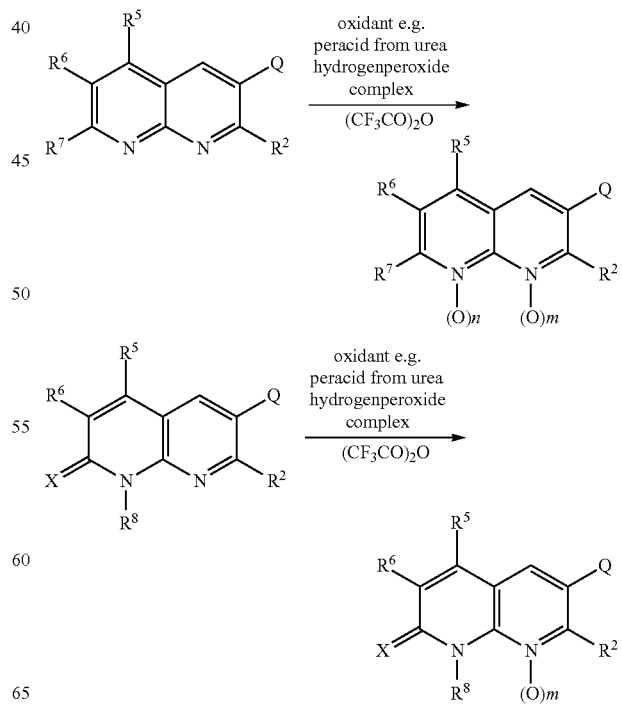

In a further aspect of the invention as shown in Scheme 19, certain substituted naphthyridine esters may be obtained from certain naphthyridine ester N-oxides and optionally substituted alkenyl, optionally substituted aryl or optionally substituted heteroarylboronic acids by heating from 30-200° C., typically (80-150)° C., in a suitable inert solvent, for example toluene, and optionally dehydrating the intermediate product with a suitable reagent, such as an acid, for example para-toluene sulfonic acid (PTSA).

Scheme 19

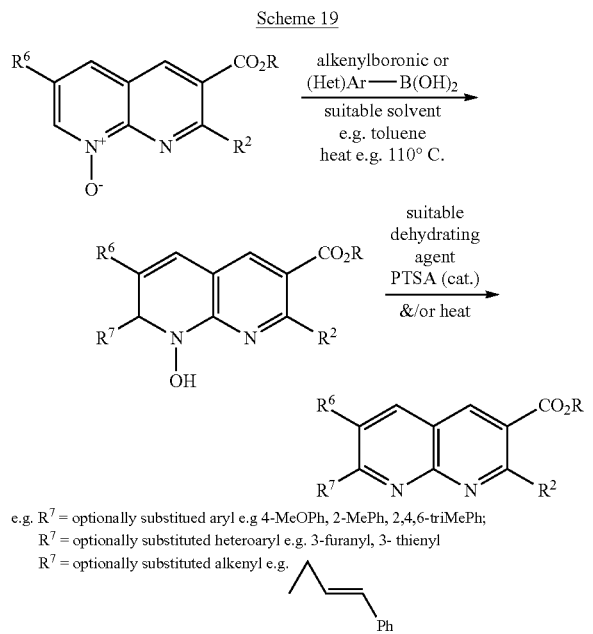

e.g. $R^7$ = optionally substitued aryl e.g 4-MeOPh, 2-MePh, 2,4,6-triMePh;
$R^7$ = optionally substituted heteroaryl e.g. 3-furanyl, 3- thienyl
$R^7$ = optionally substituted alkenyl e.g.

In a further aspect of the invention as shown in Scheme 20, certain substituted naphthyridine esters may be obtained from certain naphthyridine ester N-oxides and optionally substituted alkyl or cycloalkyl Grignard reagents, for example isopropylmagnesium chloride or cyclopropylmagnesium bromide or allyl magnesium chloride, in a suitable inert solvent or mixture of solvents, for example tetrahydrofuran, N-methylpyrrolidin-2-one typically under an inert atmosphere and anhydrous conditions and optionally dehydrating the intermediate product with a suitable reagent, such as an acid anhydride, for example acetic anhydride.

Scheme 20

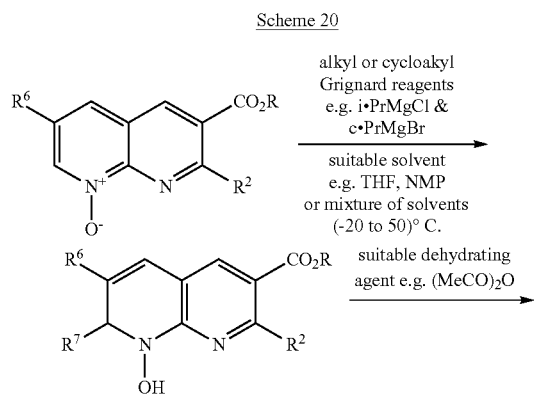

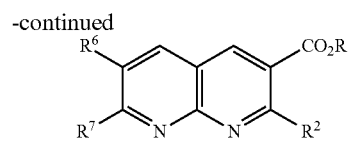

for example $R^7$ = i•Pr, c•Pr

Scheme 21

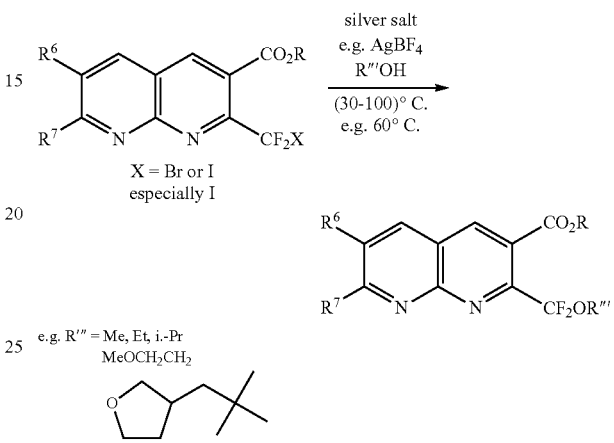

e.g. R''' = Me, Et, i.-Pr
MeOCH₂CH₂

In a further aspect of the invention as shown in Scheme 21, certain alkoxyfluoroalkyl substituted naphthyridine esters may be obtained from certain haloalkylnaphthyridine esters and alcohols in the presence of a silver salt, such as silver tetrafluoroborate, at a temperature between 30° C. and 150° C., typically at 60° C.

Abbreviations as used in the following examples are as follows: s=singlet, d=doublet, t=triplet, m=multiplet, bs=broad signal, dd=double doublet, dt=double triplet, td=triple doublet and dq=double quartet.

EXAMPLE 1

Preparation of 2-(2-trifluoromethyl-[1,8]-naphthyridine-3-carbony)-cyclohexane-1,3-dione Stage 1

Preparation of ethyl 2-trifluoromethyl-[1,8]-naphthyridine-3-carboxylate

A mixture of 2-amino-pyridine-3-carboxaldehyde (30.0 g), ethyl 4,4,4-trifluoroacetoacetate (37 ml) and piperidine (25 ml) in ethanol (100 ml) were heated to reflux with stirring for 2 hours, allowed to cool to ambient temperature then chilled to 0° C. The colourless solid that precipitated was filtered from solution, washed with a small volume of cold diethyl ether and sucked to dryness to give the required product as a colourless solid, 45.5 g. ¹H NMR (CDCl₃) δ: 9.33 (1H, m), 8.77 (1H, s), 8.38 (1H, dd), 7.70 (1H, m), 4.50 (2H, q), 1.45 (3H, t).

The following compounds were prepared in a similar procedure:

From 2-amino-6-methoxymethylpyridinyl-3-carboxaldehyde and ethyl 4,4,4-trifluoroacetoacetate to give ethyl 2-trifluoromethyl-7-methoxymethyl-[1,8]-naphthyridine-3-carboxylate, red-brown solid, ¹H NMR (CDCl₃) δ: 8.75

(1H, s), 8.37 (1H, d), 7.94 (1H, d), 4.88 (2H, s), 4.48 (2H, q), 3.55 (3H, s), 1.45 (3H, t).

From 2-amino-6-methylpyridinyl-3-carboxaldehyde and methyl 4-chloro-4,4-difluoroacetoacetate to give methyl 2-chlorodifluoromethyl-7-methyl-[1,8]-naphthyridine-3-carboxylate, solid, m.p. 134-137° C., $^1$H NMR (CDCl$_3$) δ: 8.60 (1H, s), 8.21 (1H, d), 7.55 (1H, d), 4.02 (3H, s), 2.90 (3H, s).

From 2-amino-6-methylpyridinyl-3-carboxaldehyde and ethyl 4,4-difluoroacetoacetate to give ethyl 2-difluoromethyl-7-methyl-[1,8]-naphthyridine-3-carboxylate, solid, m.p. 112-114° C., $^1$H NMR (CDCl$_3$) δ: 8.84 (1H, s), 8.21 (1H, d), 7.52-7.54 (1H, d), 7.30-7.56 (1H, t), 4.46-4.52 (2H, q), 2.88 (3H, s), 1.45-1.49 (3H, t).

From 2-amino-6-methylpyridinyl-3-carboxaldehyde and methyl 4-methoxyacetoacetate to give methyl 2-methoxymethyl-7-methyl-[1,8]-naphthyridine-3-carboxylate, yellow solid, $^1$H NMR (CDCl$_3$) δ: 8.64 (1H, s), 8.13 (1H, d), 7.44 (1H, d), 5.08 (2H, s), 3.93 (3H, s), 3.43 (3H, s), 2.84 (3H, s). Molecular ion: (MH)$^+$247.

Stage 2

Preparation of 2-trifluoromethyl-[1,8]-naphthyridine-3-carboxylic acid

To a stirred solution of ethyl 2-trifluoromethyl-[1,8]-naphthyridine-3-carboxylate (25.0 g) in ethanol (100 ml) and water (35 ml) was added sodium hydroxide (11.1 g) at ambient temperature. The mixture was stirred for 6 hours, acidified with aqueous 2M hydrochloric acid and the solid that precipitated from solution was filtered from solution, sucked to dryness then finally dried under vacuum to give the required product as a colourless solid, 25 g, containing some sodium chloride. $^1$H NMR (d$_6$-DMSO) δ: 9.35 (1H, m), 9.18 (1H, s), 8.77 (1H, dd), 7.94 (1H, m).

Stage 3

To a stirred suspension of 2-trifluoromethyl-[1,8]-naphthyridine-3-carboxylic acid (2.0 g) and cyclohexane-1,3-dione (1.11 g) in dry acetonitrile (60 ml) was added in portions N,N'-dicyclohexylcarbodiimide (1.87 g) at ambient temperature. The mixture was stirred for 6 hours, the insolubles were filtered from solution and triethylamine (1.75 ml) and acetone cyanhydrin (0.14 ml) were added to the filtrate. The solution was stirred at ambient temperature for 16 hours then evaporated under reduced pressure. The residual solid was purified by chromatography (silica, (toluene:dioxane, ethanol:triethylamine:water, ratio by volume 20:8:4:1) to give the triethylamine salt of the required product. $^1$H NMR (CDCl$_3$) δ 9.13 (1H, dd), 8.18 (1H, dd), 8.00 (1H, s), 7.52 (1H, dd), 3.20 (6H, q), 2.40 (4H, t), 1.95 (2H, quintet), 1.30 (9H, t).

The salt was washed with ethyl acetate, filtered then suspended in dichloromethane and acidified with aqueous 2M hydrochloric acid (5 ml). The organic fraction was separated, washed with water (2×10 ml), dried over magnesium sulfate then evaporated under reduced pressure to give the required product as a pale yellow solid, 0.56 g, m.p. 175-177° C.
$^1$H NMR (d$_6$-DMSO) δ: 9.29 (1H, dd), 8.65 (1H, s), 8.61 (1H, dd), 7.86 (1H, dd), 2.64-2.58 (4H, m), 1.96 (2H, quintet). Molecular ion: (MH)$^+$337.

In a similar procedure to Example 1, 2-trifluoromethyl-[1,8]-naphthyridine-3-carboxylic acid was reacted with 2-methyl-2,4-dihydropyrazol-3-one to give 2-methyl-4-(2-trifluoromethyl-[1,8]-naphthyridine-3-carbony)-2,4-dihydropyrazol-3-one as a solid, $^1$H NMR (D$_2$O) δ: 9.18 (1H, d), 8.59 (1H, s), 8.55 (1H, dd), 7.80 (1H, dd), 4.76 (1H, s), 3.29 (3H, s), Molecular ion: (M-H) 321.

In a similar procedure to Example 2-(1,1-difluoro-2-methoxyethyl)-1,6-fluoro-7-methyl-[1,8]-naphthyridine-3-carboxylic acid was reacted with 2-ethyl-2,4-dihydropyrazol-3-one to give 2-ethyl-4-[6-fluoro-2-(1,1-difluoro-2-methoxyethyl)-[1,8]-naphthyridine-3-carbony]-2,4-dihydropyrazol-3-one, orange foamy solid, Molecular ion: (MH)$^+$395, $^1$H NMR (CDCl$_3$) δ: 8.26 (1H, s), 7.78-7.80 (1H, d), 7.30 (1H, s), 4.32-4.40 (2H, t), 4.06-4.12 (2H, q), 3.50 (3H, s), 2.86 (3H, d), 1.44-1.48 (3H, t).

The following compounds were prepared in a similar procedure to Example 1, Stage 3 from 2-trifluoromethyl-[1,8]-naphthyridine-3-carboxylic acid and the corresponding ketones:

2-(2-trifluoromethyl-[1,8]-naphthyridine-3-carbony)-5-methylcyclohexane-1,3-dione, yellow solid, $^1$H NMR (CDCl$_3$) δ: 16.64 (1H, s), 9.28 (1H, dd), 8.27 (1H, dd), 8.11 (1H, s), 7.64 (1H, dd), 2.87 (1H, m), 2.56 (1H, dd), 2.48 (1H, m), 2.37-2.32 (1H, m), 2.16 (1H, d), 1.14 (3H, d).

4-(2-trifluoromethyl-[1,8]-naphthyridine-3-carbony)-(2,2,6,6-tetramethylpyran-3,5-dione), pale yellow solid, $^1$H NMR (CDCl$_3$): δ 16.75 (1H, s), 9.29-9.28 (1H, m), 8.30 (1H, dd), 8.2 (1H, s), 7.67 (1H, dd), 1.65 (6H, s,) 1.34 (6H, s).

6-(2-trifluoromethyl-[1,8]-naphthyridine-3-carbony)-(2,2,4,4-tetramethylcyclohexane-1,3,5-trione), pale yellow solid, $^1$H NMR (CDCl$_3$), δ 17.21 (1H, s), 9.31 (1H, bs), 8.32 (1H, bd), 8.22 (1H, bs), 7.69 (1H, bs), 1.60 (6H, s) 1.30 (6H, s). Molecular ion: (MH)$^+$407.

5-(2-trifluoromethyl-[1,8]-naphthyridine-3-carbony)-spiro[2.5]octane-4,6-dione, brown solid, $^1$H NMR (CDCl$_3$) δ: 16.78 (1H, s), 9.28-9.25 (1H, m), 8.29-8.26 (1H, m), 8.13 (1H, s), 7.66-7.63 (1H, m), 2.90 (1H, t), 2.51 (1H, t), 1.98-1.93 (2H, m), 1.73 (1H, q), 1.17-1.13 (2H, m), 0.71 (1H, q).

3-(2-trifluoromethyl-[1,8]-naphthyridine-3-carbony)-bicyclo[3.2.1]octane-2,4-dione, off-white solid, m.p. 189-191° C. $^1$H NMR (CDCl$_3$): δ 9.30 (1H, dd), 8.65 (1H, s), 8.62 (1H, dd), 7.86 (1H, dd), 2.91 (2H, bs), 2.07-2.16 (3H, m), 1.78-1.68 (3H, m).

From 1-methylbicyclo[3.2.1]octane-2,4-dione (WO 2005105717), 3-(2-trifluoromethyl-[1,8]-naphthyridine-3-carbony)-1-methyl-bicyclo[3.2.1]octane-2,4-dione, pale yellow gum, $^1$H NMR (CD$_3$OD): δ 9.23 (1H, double doublet), 8.58 (1H, double doublet), 8.50 (1H, s), 7.83 (1H, double doublet), 2.98-3.03 (1H, m), 2.34-2.42 (1H, m), 2.09 (1H, d), 1.81-2.03 (3H, m), 1.81 (1H, double doublet), 1.40 (3H, s).

From 6-methylbicyclo[3.2.1]octane-2,4-dione (WO 2005105717), 3-(2-trifluoromethyl-[1,8]-naphthyridine-3-carbony)-6-methyl-bicyclo[3.2.1]octane-2,4-dione, pale yellow gum, $^1$H NMR (CD$_3$OD): δ 9.20 (1H, double doublet), 8.57 (1H, double doublet), 8.47 (1H, s), 7.80 (1H, double doublet), 2.44-2.53 (1H, m), 1.80-1.91 (1H, m), 1.53-2.32 (5H, m), 1.06 (3H, d).

The following compounds were prepared in a similar procedure to Example 1, Stage 3 from cyclohexane1,3-dione and the corresponding naphthyridine carboxylic acids.

From 2-pentafluoroethyl-[1,8]-naphthyridine-3-carboxylic acid, 2-(2-pentafluoroethylnaphthyridine-3-carbonyl)-cyclohexane-1,3-dione, colourless solid. $^1$H NMR (CDCl$_3$)

δ: 16.67 (1H, s), 9.31 (1H, bs), 8.30 (1H, m), 8.13 (1H, m), 7.69 (1H, m), 2.90 (2H, m), 2.45 (2H, m), 2.13 (2H, m). Molecular ion: (M-H) 385.

From 6-chloro-2-trifluoromethylnaphthyridine-3-carboxylic acid, 2-(6-chloro-2-trifluoromethyl-[1,8]-naphthyridine-3-carbonyl)-cyclohexane-1,3-dione, maroon solid. $^1$H NMR (CDCl$_3$) δ: 16.55 (1H, s), 9.16 (1H, d), 8.23 (1H, d), 8.02 (1H, s), 2.85 (2H, t), 2.42 (2H, t), 2.08 (2H, quintet). Molecular ion: (MH)$^+$371.

From 7-chloro-2-trifluoromethylnaphthyridine-3-carboxylic acid, 2-(7-chloro-2-trifluoromethyl-[1,8]-naphthyridine-3-carbonyl)-cyclohexane-1,3-dione, pale yellow solid. $^1$H NMR (CDCl$_3$) δ: 8.19 (1H, d), 8.10 (1H, s), 7.64 (1H, d), 2.85 (2H, bs), 2.42 (2H, bs), 2.08 (2H, quintet) Molecular ion: (MH)$^+$371.

From 2,7-bis(trifluoromethyl)-[1,8]-naphthyridine-3-carboxylic acid, 2-(2,7-bis(-trifluoromethyl)-[1,8]-naphthyridine-3-carbonyl)-cyclohexane-1,3-dione, pale yellow solid. $^1$H NMR (CDCl$_3$) δ: 8.19 (1H, d), 8.10 (1H, s), 7.64 (1H, d), 2.85 (2H, bs), 2.42 (2H, bs), 2.08 (2H, quintet) Molecular ion: (MH)$^+$371.

Also as triethylamine salt: $^1$H NMR (CDCl$_3$) δ: 8.42 (1H, d), 8.10 (1H, s), 7.92 (1H, d), 3.18 (6H, q), 2.52-2.48 (4H, m), 2.02-1.95 (2H, quintet). 1.30 (9H, t), Molecular ion: (MH)$^+$ 405.

From 2-difluoromethyl-[1,8]-naphthyridine-3-carboxylic acid, 2-(2-difluoromethyl-[1,8]-naphthyridine-3-carbony)-cyclohexane-1,3-dione $^1$H NMR (CDCl$_3$) δ: 16.80 (1H, s), 9.23 (1H, dd), 8.25 (1H, dd), 8.10 (1H, s), 7.62 (1H, dd), 6.87 (1H, t), 2.10-2.06 (4H, m), 1.29-1.25 (2H, m). Molecular ion: (MH)$^+$321.

From 2-difluoromethyl-7-methylnaphthyridine-3-carboxylic acid, 2-(2-difluoromethyl-7-methyl-[1,8]-naphthyridine-3-carbonyl)-cyclohexane-1,3-dione, gum. $^1$H NMR (CDCl$_3$) δ: 8.32-8.34 (1H, d), 8.14 (1H, s), 7.60-7.62 (1H, d), 6.68-6.94 (1H, t), 2.96 (3H, s), 2.50-2.80 (4H, broad s), 2.06-2.10 (2H, t).

From 2-difluoromethyl-6-fluoro-7-methylnaphthyridine-3-carboxylic acid, 2-(2-difluoromethyl-6-fluoro-7-methyl-[1,8]-naphthyridine-3-carbonyl)-cyclohexane-1,3-dione, gum. $^1$H NMR (CDCl$_3$) δ: 8.02 (1H, s), 7.76 (1H, d), 6.83 (1H, t), 2.43 (3H, broad s), 2.07 (2H, quintet).

From 2-chlorodifluoromethyl-6-fluoro-7-methylnaphthyridine-3-carboxylic acid, 2-(2-chlorodifluoromethyl-6-fluoro-7-methyl-[1,8]-naphthyridine-3-carbonyl)-cyclohexane-1,3-dione, yellow solid. $^1$H NMR (CDCl$_3$) δ: 7.97 (1H, s), 7.74 (1H, d), 2.84 (3H, d), 2.83 (2H, t), 2.42 (2H, broad signal), 2.07 (2H, quintet).

From 2-methyl-[1,8]-naphthyridine-3-carboxylic acid, 2-(2-methyl-[1,8]-naphthyridine-3-carbony)-cyclohexane-1,3-dione $^1$H NMR (CDCl$_3$) δ: 9.39 (1H, dd), 8.47 (1H, dd), 8.03 (1H, s), 7.74 (1H, dd), 2.76 (3H, s), 2.34-2.89 (4H, m), 2.11 (2H, quintet). Molecular ion: (M-H) 281.

From 7-(morpholin-4-yl)-2-trifluoromethyl-[1,8]-naphthyridine-3-carboxylic acid, 2-[(7-(morpholin-4-yl)-2-trifluoromethyl-[1,8]-naphthyridine-3-carbony)-cyclohexane-1,3-dione, yellow solid. $^1$H NMR (CDCl$_3$) δ: 7.89 (1H, d, 7.82 (1H, s), 7.10 (1H, d), 3.90 (4H, m), 3.84 (4H, m), 2.80 (2H, bs), 2.44 (2H, bs), 2.06 (2H, quintet).

From 7-(6-fluoropyrid-3-yl)-2-trifluoromethyl-[1,8]-naphthyridine-3-carboxylic acid, 2-[7-(6-fluoropyrid-3-yl)-2-trifluoromethyl-[1,8]-naphthyridine-3-carbony)-cyclohexane-3-dione, yellow solid.

$^1$H NMR (CDCl$_3$) δ: 16.63 (1H, s), 9.05 (1H, m), 8.90 (1H, m), 8.37 (1H, d), 8.12 (1H, d), 7.14 (1H, dd), 2.86 (2H, bs), 2.44 (2H, bs), 2.09 (2H, quintet).

From 6-methyl-2-trifluoromethyl-[1,8]-naphthyridine-3-carboxylic acid, 2-[6-methyl-2-trifluoromethyl-[1,8]-naphthyridine-3-carbony]-cyclohexane-1,3-dione, yellow solid.

$^1$H NMR (CDCl$_3$) δ: 16.66 (1H, s), 9.10 (1H, d), 8.01 (1H, s), 7.98 (1H, d), 2.80 (2H, bs), 2.60 (3H, s), 2.44 (2H, bs), 2.07 (2H, quintet).

From 7-methyl-2-trifluoromethyl-[1,8]-naphthyridine-3-carboxylic acid, 2-[7-methyl-2-trifluoromethyl-[1,8]-naphthyridine-3-carbony]-cyclohexane-1,3-dione, yellow solid.

$^1$H NMR (CDCl$_3$) δ: 16.73 (1H, s), 8.13 (1H, d), 8.05 (1H, s), 7.52 (1H, d), 2.87 (3H, s), 2.84 (2H, t), 2.42 (2H, broad t), 2.07 (2H, quintet).

From 7-ethyl-2-trifluoromethyl-[1,8]-naphthyridine-3-carboxylic acid, 2-[7-ethyl-trifluoromethyl-[1,8]-naphthyridine-3-carbony]-cyclohexane-1,3-dione, yellow solid, $^1$H NMR (CDCl$_3$) δ: 16.74 (1H, s), 8.15 (1H, d), 8.06 (1H, d), 7.54 (1H, d), 3.15 (2H, q), 2.84 (2H, t), 2.42 (2H, t), 2.08 (2H, quintet), 1.46 (3H, t). Molecular ion: (MH)$^+$365.

From 7-methoxymethyl-2-trifluoromethyl-[1,8]-naphthyridine-3-carboxylic acid, 2-[7-methoxymethyl-trifluoromethyl-[1,8]-naphthyridine-3-carbony]-cyclohexane-1,3-dione, yellow solid, $^1$H NMR (CDCl$_3$) δ: 16.70 (1H, s), 8.27 (1H, s), 7.88 (1H, d), 4.87 (s, 2H), 3.53, (3H, s), 2.85 (2H, t), 2.43 (2H, t), 2.08 (2H, quintet).

From 7-ethyl-6-fluoro-2-trifluoromethyl-[1,8]-naphthyridine-3-carboxylic acid, 2-[7-ethyl-6-fluoro-2-trifluoromethyl-[1,8]-naphthyridine-3-carbony]-cyclohexane-1,3-dione, yellow solid, $^1$H NMR (CDCl$_3$) δ: 8.02 (1H, s), 7.75 (1H, s), 3.20-3.14 (2H, m), 2.83 (2H, broad s), 2.43 (2H, broad s), 2.07 (2H, quintet), 1.46 (3H, t). Molecular ion: (MH)$^+$383.

From 6-fluoro-7-methylethyl-2-trifluoromethyl-[1,8]-naphthyridine-3-carboxylic acid, 2-[6-fluoro-7-methylethyl-2-trifluoromethyl-[1,8]-naphthyridine-3-carbony]-cyclohexane-1,3-dione, yellow solid, $^1$H NMR (CDCl$_3$) δ: 8.01 (1H, s), 7.75 (1H, d), 3.03 (2H, double doublet), 2.80 (2H, broad s), 2.41 (2H, broad s), 2.42-2.33 (1H, m), 1.01 (6H, d). Molecular ion: (MH)$^+$397.

From 7-cyclopropyl-6-fluoro-2-trifluoromethyl-[1,8]-naphthyridine-3-carboxylic acid, 2-[7-cyclopropyl-6-fluoro-2-trifluoromethyl-[1,8]-naphthyridine-3-carbony]-cyclohexane-1,3-dione, yellow solid, $^1$H NMR (CDCl$_3$) δ: 7.97 (1H, s), 7.79 (1H, d), 2.86-2.37 (5H, m), 2.07 (2H, quintet), 1.59-1.57 (2H, m), 1.29-1.24 (2H, m). Molecular ion: (MH)$^+$395

From 6-fluoro-7-(2-methylpropyl)-2-trifluoromethyl-[1,8]-naphthyridine-3-carboxylic acid, 2-[6-fluoro-7-(2-methylpropyl)-2-trifluoromethyl-[1,8]-naphthyridine-3-carbony]-cyclohexane-1,3-dione, yellow solid, $^1$H NMR (CDCl$_3$) δ: 8.01 (1H, s), 7.75 (1H, d), 3.03 (2H, double doublet), 2.80 (2H, broad s), 2.41 (2H, broad s), 2.42-2.33 (1H, m), 1.01 (6H, d). Molecular ion: (MH)$^+$411.

From 7-n.butyl-6-fluoro-2-trifluoromethyl-[1,8]-naphthyridine-3-carboxylic acid, 2-[7-butyl-6-fluoro-2-trifluoromethyl-[1,8]-naphthyridine-3carbonyl]-cyclohexane-1,3-dione, yellow solid, $^1$H NMR (CDCl$_3$) δ: 8.01 (1H, s), 7.74 (1H, d), 3.14 (2H, td), 2.78 (2H, broads), 2.47 (2H, broad s), 2.07 (2H, quintet), 1.87 (2H, quintet), 1.52-1.43 (2H, m), 0.98 (3H, t). Molecular ion: (MH)$^+$410.

From 6-fluoro-7-[(E)(prop-1-enyl)]-2-trifluoromethyl-[1,8]-naphthyridine-3-carboxylic acid, 2-(6-fluoro-7-[(E)(prop-1-enyl)]-2-trifluoromethyl-[1,8]-naphthyridine-3-carbony)-cyclohexane-1,3-dione, pale orange solid, $^1$H NMR (CDCl$_3$) δ:16.67 (1H, s), 7.97 (1H, s), 7.75 (1H, d), 7.63-

7.52 (1H, m), 6.92 (1H, d), 2.84 (2H, t), 2.42 (2H, t), 2.09-2.07 (5H, m). Molecular ion: (MH)$^+$395.

From 6-fluoro-7-[(E)(styryl)]-2-trifluoromethyl-[1,8]-naphthyridine-3-carboxylic acid, 2-(6-fluoro-7-[(E)(styryl)]-2-trifluoromethyl-[1,8]-naphthyridine-3-carbony)-cyclohexane-1,3-dione, yellow solid, Molecular ion: (MH)$^+$457.

From 6-fluoro-7-[(4-methoxyphenyl)]-2-trifluoromethyl-[1,8]-naphthyridine-3-carboxylic acid, 2-[6-fluoro-7-[(4-methoxyphenyl)]-2-trifluoromethyl-[1,8]-naphthyridine-3-carbony]-cyclohexane-1,3-dione, yellow solid, $^1$H NMR (CDCl$_3$) δ: 8.28 (2H, d), 8.02 (1H, s), 7.86 (1H, d), 7.05 (2H, d), 3.92 (3H, s), 2.84 (2H, t), 2.42 (2H, t), 2.05 (2H, quintet). Molecular ion: (MH)$^+$461.

From 6-fluoro-7-(thiophen-3-yl)-2-trifluoromethyl-[1,8]-naphthyridine-3-carboxylic acid, 2-[6-fluoro-7-(thiophen-3-yl)-2-trifluoromethyl-[1,8]-naphthyridine-3-carbony]-cyclohexane-1,3-dione, yellow solid, $^1$H NMR (CDCl$_3$) δ: 16.57 (1H, s), 8.45 (1H, broad s), 8.19 (1H, d), 8.02 (1H, d), 7.46 (1H, double doublet), 2.85 (2H, broad s), 2.43 (2H, broad s), 2.08 (2H, quintet). Molecular ion: (MH)$^+$437.

From 6-fluoro-7-[(4-fluorophenyl)]-2-trifluoromethyl-[1,8]-naphthyridine-3-carboxylic acid, 2-[6-fluoro-7-[(4-fluorophenyl)]-2-trifluoromethyl-[1,8]-naphthyridine-3-carbony]-cyclohexane-1,3-dione, yellow solid, $^1$H NMR (CDCl$_3$) δ: 8.26-8.28 (2H, m), 8.05 (1H, s), 7.92 (1H, d), 7.24 (2H, d), 2.85 (2H, broad s), 2.44 (2H, broad s), 2.05 (2H, quintet). Molecular ion: (MH)$^+$449.

From 7-(1,1-difluoroethyl)-6-fluoro-2-trifluoromethyl-[1,8]-naphthyridine-3-carboxylic acid, 2-[7-(1,1-difluoroethyl)-6-fluoro-2-trifluoromethyl-[1,8]-naphthyridine-3-carbony]-cyclohexane-1,3-dione, yellow solid, $^1$H NMR (CDCl$_3$) δ: 8.08 (1H, s), 7.95 (1H, d), 2.85 (2H, broad s), 2.42 (2H, broad s), 2.23 (3H, t), (2H, quintet). Molecular ion: (MH)$^+$418.

From 6-fluoro-7-fluoromethyl-2-trifluoromethyl-[1,8]-naphthyridine-3-carboxylic acid, 2-[6-fluoro-7-fluoromethyl-2-trifluoromethyl-[1,8]-naphthyridine-3-carbony]-cyclohexane-1,3-dione, yellow solid, $^1$H NMR (CDCl$_3$) δ: 8.08 (1H, s), 7.92 (1H, d), 5.82 (2H, d), 2.83 (2H, t), 2.42 (2H, t), 2.08 (2H, t). Molecular ion: (MH)$^+$387.

From 6-fluoro-2-methoxymethyl-[1,8]-naphthyridine-3-carboxylic acid, 2-[6-fluoro-2-methoxymethyl-[1,8]-naphthyridine-3-carbony]-cyclohexane-1,3-dione, brown solid. $^1$H NMR (CDCl$_3$) δ: 9.03 (1H, d), 7.93 (1H, s), 7.81 (1H, double doublet), 4.83 (2H, s), 3.25 (3H, s), 2.83 (2H, t), 2.44 (2H, t), 2.06 (2H, quintet). Molecular ion: (MH)$^+$ 331.

From 5,7-dimethyl-6-fluoro-2-trifluoromethyl-[1,8]-naphthyridine-3-carboxylic acid, 2-[5,7-dimethyl-6-fluoro-2-trifluoromethyl-[1,8]-naphthyridine-3-carbony]-cyclohexane-1,3-dione, yellow solid. $^1$H NMR (CDCl$_3$) δ: 16.69 (1H, s), 8.13 (1H, s), 7.82 (1H, d), 2.85 (2H, t), 2.81 (3H, d), 2.59 (3H, d), 2.42 (2H, t), 2.08 (2H, quintet).

From 6-fluoro-2-methoxymethyl-7-methyl-[1,8]-naphthyridine-3-carboxylic acid, 2-[6-fluoro-2-methoxymethyl-7-methyl-[1,8]-naphthyridine-3-carbony]-cyclohexane-1,3-dione, brown solid. $^1$H NMR (CDCl$_3$) δ: 7.88 (1H, s), 7.69 (1H, d), 4.81 (2H, s), 3.23 (3H, s), 2.79 (3H, d), 2.61 (4H, broad signal), 2.07 (2H, quintet).

From 6-fluoro-2-(1,1-difluoro-2-methoxyethyl)-7-methyl-[1,8]-naphthyridine-3-carboxylic acid, 2-[6-fluoro-2-(1,1-difluoro-2-methoxyethyl)-[1,8]-naphthyridine-3-carbony]-cyclohexane-1,3-dione, colourless solid, Molecular ion: (MH)$^+$395, $^1$H NMR (CDCl$_3$) δ:16.7 (1H, s), 7.94 (1H, s), 7.72-7.74 (1H, d), 4.28-4.38 (2H, broad triplet), 3.50 (3H, s), 2.84 (3H, d), 2.80-2.84 (2H, t), 2.38-2.42 (2H, t), 2.04-2.10 (2H, m).

From 2-methyl-7-trifluoromethyl-[1,8]-naphthyridine-3-carboxylic acid, 2-[2-methyl-7-trifluoromethyl-[1,8]-naphthyridine-3-carbony]-cyclohexane-1,3-dione, brown solid. $^1$H NMR (CDCl$_3$) δ: 17.25 (1H, s), 8.35 (1H, d), 7.93 (1H, s), 7.82 (1H, d), 2.86 (2H, d), 2.72 (3H, s), 2.47 (2H, t), 2.10 (2H, quintet).

From 2-ethyl-7-trifluoromethyl-[1,8]-naphthyridine-3-carboxylic acid, 2-[2-ethyl-7-trifluoromethyl-[1,8]-naphthyridine-3-carbony]-cyclohexane-1,3-dione, yellow solid. $^1$H NMR (CDCl$_3$) δ: 17.26 (1H, s), 8.34 (1H, d), 7.90 (1H, s), 7.82 (1H, d), 2.98 (2H, q), 2.88 (2H, t), 2.46 (1H, t), 2.12 (2H, qi), 1.40 (3H, t)

From 2-(methanesulfonyl-N-methylaminomethyl)-7-trifluoromethyl-[1,8]-naphthyridine-3-carboxylic acid, 2-[{methanesulfonyl-N-methylaminomethyl}-7-trifluoromethyl-[1,8]-naphthyridine-3-carbony]-cyclohexane-1,3-dione, $^1$H NMR (CD$_3$OD) δ: 8.75 (1H, d), 8.35 (1H, s), 8.05 (1H, d), 4.65 (2H, s), 2.95 (3H, s). 2.65 (3H, s), 2.30-3.00 (4H, broad signal), 2.10 (2H, quintet).

From 6-fluoro-7-(2,2,2-trifluoroethylamino)-2-trifluoromethyl-[1,8]-naphthyridine-3-carboxylic acid, 2-[6-fluoro-7-(2,2,2-trifluoroethylamino)-2-trifluoromethyl-[1,8]-naphthyridine-3-carbony]-cyclohexane-1,3-dione. $^1$H NMR (CDCl$_3$) δ: 16.78 (1H, s), 7.86 (1H, s), 7.58 (1H, d), 5.69 (1H, broad s), 4.59-4.50 (2H, m), 2.83 (2H, t), 2.42 (2H, t), 2.07 (2H, quintet).

From 7-(3,3-difluoroazetidin-1-yl)-6-fluoro-2-trifluoromethyl-[1,8]-naphthyridine-3-carboxylic acid, 2-[7-(3,3-difluoroazetidin-1-yl)-6-fluoro-2-trifluoromethyl-[1,8]-naphthyridine-3-carbony]-cyclohexane-1,3-dione. $^1$H NMR (CDCl$_3$) δ: 16.80 (1H, s), 7.84 (1H, s), 7.55 (1H, d), 4.79 (4H, m), 2.83 (2H, t), 2.42 (2H, t), 2.07 (2H, quintet).

From 6-fluoro-7-(3-methoxyazetidin-1-yl)-2-trifluoromethyl-[1,8]-naphthyridine-3-carboxylic acid, 2-[6-fluoro-7-(3-methoxyazetidin-1-yl)-2-trifluoromethyl-[1,8]-naphthyridine-3-carbony]-cyclohexane-1,3-dione. $^1$H NMR (CDCl$_3$) δ: 16.89 (1H, s), 7.75 (1H, s), 7.41 (1H, d), 4.66-4.62 (2H, m), 4.42-4.34 (3H, m), 3.37 (3H, s), 2.81 (2H, t), 2.42 (2H, t), 2.06 (2H, quintet).

From 7-(cyclopropylamino)-6-fluoro-2-trifluoromethyl-[1,8]-naphthyridine-3-carboxylic acid, 2-[7-(cyclopropylamino)-6-fluoro-2-trifluoromethyl-[1,8]-naphthyridine-3-carbony]-cyclohexane-1,3-dione. $^1$H NMR (CDCl$_3$) δ: 16.88 (1H, s), 7.79 (1H, s), 7.42 (1H, d), 5.62 (1H, s), 5.27-5.23 (1H, m), 2.82 (2H, t), 2.42 (2H, t), 2.06 (2H, quintet), 1.03-0.98 (2H, m), 0.69-0.65 (2H, m).

From 6-fluoro-7-methylamino-2-trifluoromethyl-[1,8]-naphthyridine-3-carboxylic acid, 2-[6-fluoro-7-methylamino-2-trifluoromethyl-[1,8]-naphthyridine-3-carbony]-cyclohexane-1,3-dione. $^1$H NMR (CDCl$_3$) δ: 7.80 (1H, s), 7.46 (1H, d), 6.78 (1H, bs), 3.22 (3H, d), 2.75 (4H, bs), 2.05 (2H, quintet).

From 7-(dimethylamino)-6-fluoro-2-trifluoromethyl-[1,8]-naphthyridine-3-carboxylic acid, 2-[7-(dimethylamino)-6-fluoro-2-trifluoromethyl-[1,8]-naphthyridine-3-carbony]-cyclohexane-1,3-dione. $^1$H NMR (CDCl$_3$) δ: 7.76 (1H, s), 7.46 (1H, d), 3.40 (6H, d), 2.86 (2H, broad signal), 2.42 (2H, broad signal), 2.06 (2H, quintet).

From 7-(diethylamino)-6-fluoro-2-trifluoromethyl-[1,8]-naphthyridine-3-carboxylic acid, 2-[7-(diethylamino)-6-fluoro-2-trifluoromethyl-[1,8]-naphthyridine-3-carbony]-cyclohexane-1,3-dione. $^1$H NMR (CDCl$_3$) δ: 16.90 (1H, s), 7.72 (1H, s), 7.44 (1H, d), 3.78 (4H, q), 2.80 (2H, m), 2.40 (2H, m), 2.05 (2H, m), 1.30 (6H, t).

From 6-fluoro-7-(N-methylethylamino)-2-trifluoromethyl-[1,8]-naphthyridine-3-carboxylic acid, 2-[6-fluoro-7-(N-methylethylamino)-2-trifluoromethyl-[1,8]-naphthyridine-3-carbony]-cyclohexane-1,3-dione. $^1$H NMR (CDCl$_3$) δ: 7.74 (1H, s), 7.46 (1H, d), 3.80 (2H, q) 3.37 (3H, d), 2.60 (4H, bs), 2.04 (2H, quintet), 1.29 (3H, t).

From 6-fluoro-7-(2-methoxyethylamino)-2-trifluoromethyl-[1,8]-naphthyridine-3-carboxylic acid, 2-[6-fluoro-7-(2-methoxyethylamino)-2-trifluoromethyl-[1,8]-naphthyridine-3-carbony]-cyclohexane-1,3-dione, yellow solid, $^1$H NMR (CDCl$_3$) δ: 16.88 (1H, s), 7.76 (1H, s), 7.46 (1H, d), 5.90 (1H, bs), 3.98 (2H, m), 3.68 (2H, t), 3.42 (3H, s), 2.80 (2H, t), 2.42 (2H, broad signal), 2.06 (2H, quintet).

From 6-fluoro-7-(2-methoxyethylmethylamino)-2-trifluoromethyl-[1,8]-naphthyridine-3-carboxylic acid, 2-[6-fluoro-7-(2-methoxyethylmethylamino)-2-trifluoromethyl-[1,8]-naphthyridine-3-carbony]-cyclohexane-1,3-dione. $^1$H NMR (CDCl$_3$) δ: 16.97 (1H, s), 7.76 (1H, s), 7.49 (1H, d), 3.98 (2H, m), 3.69 (2H, t), 3.45 (3H, d), 3.35 (3H, d), 2.81 (2H, t), 2.42 (2H, t), 2.06 (2H, quintet).

From 6-fluoro-7-(morpholin-4-yl)-2-trifluoromethyl-[1,8]-naphthyridine-3-carboxylic acid, 2-[6-fluoro-7-(morpholin-4-yl)-2-trifluoromethyl-[1,8]-naphthyridine-3-carbony]-cyclohexane-1,3-dione. $^1$H NMR (CDCl$_3$) δ: 7.82 (1H, s), 7.58 (1H, d), 3.98 (4H, m), 3.86 (4H, m), 3.45 (3H, d), 2.81 (2H, t), 2.42 (2H, t), 2.06 (2H, quintet).

From 6-fluoro-7-propargylamino-2-trifluoromethyl-[1,8]-naphthyridine-3-carboxylic acid, 2-[6-fluoro-7-propargylamino)-2-trifluoromethyl-[1,8]-naphthyridine-3-carbony]-cyclohexane-1,3-dione $^1$H NMR (CDCl$_3$) δ: 7.82 (1H, s), 7.51 (1H, d), 5.60 (1H, bs), 4.60 (1H, m), 2.82 (2H, t), 2.42 (2H, t), 2.34 (1H, t), 2.08 (2H, quintet).

From 6-fluoro-7-methyl-2[(2,2,2-trifluoroethoxy)difluoromethyl]-[1,8]-naphthyridine-3-carboxylic acid, 2-[6-fluoro-7-methyl-2[(2,2,2-trifluoroethoxy)difluoromethyl]-[1,8]-naphthyridine-3-carbony]-cyclohexane-1,3-dione, yellow solid. $^1$H NMR (CDCl$_3$) δ: 7.95 (1H, s), 7.72 (1H, d), 4.38 (2H, q), 2.83 (3H, d), 2.81 (2H, broad s), 2.39 (2H, broad s), 2.04 (2H, quintet).

EXAMPLE 2

Preparation of 2-(7-ethoxy-2-trifluoromethyl-[1,8]-naphthyridine-carbonyl)-cyclohexane-1,3-dione Stage 1

Preparation of ethyl 8-oxy-2-trifluoromethyl-[1,8]-naphthyridine-3-carboxylate

To a stirred solution of ethyl 2-trifluoromethyl-[1,8]-naphthyridine-3-carboxylate (74 g) in dichloromethane (1000 ml) at 10° C. was added urea hydrogen peroxide (130 g, 30% active oxygen) followed by trifluoroacetic anhydride (63 ml) in portions allowing the mixture to reflux. The mixture was stirred for 6 hours during which time the mixture cooled to ambient temperature. It was then heated to reflux for 0.5 hours, cooled to ambient temperature then washed with aqueous sodium thiosulfate (20 ml, 0.1M), then aqueous sodium hydrogen carbonate (2×15 ml) and brine (20 ml). The organic phase was separated, dried over magnesium sulphate, filtered then evaporated under reduced pressure to give a solid. The solid was purified by chromatography (silica, ethyl acetate then methanol) to give the required product as a pale yellow solid, 41 g. $^1$H NMR (CDCl$_3$) δ: 8.83 (1H, dd), 8.81 (1H, s), 7.79 (1H, dd), 7.56 (1H, dd), 4.51 (2H, q), 1.45 (3H, t).

Stage 2

Preparation of ethyl 7-chloro-2-trifluoromethyl-[1,8]-naphthyridine-3-carboxylate To a stirred solution of ethyl 8-oxy-2-trifluoromethyl-[1,8]-naphthyridine-3-carboxylate (41.0 g) in dry dichloromethane (700 ml) containing triethylamine (26 ml) at 10° C. was added dropwise phosphorus oxychloride (17.0 ml). The mixture was allowed to warm to ambient temperature and stirred for 1 hour then heated to reflux for a further 4 hours. The mixture was cooled to ambient temperature, poured into water then taken to pH 7 with sodium hydrogen carbonate. The organic phase was separated, washed with brine, dried over magnesium sulphate, filtered then evaporated under reduced pressure. The residual material was purified by chromatography (silica, hexane/ethyl acetate/ 3:2 by volume) to give a pink solid, 34 g, that contained a mixture of the ethyl 7-chloro-2-trifluoromethyl-[1,8]-naphthyridine-3-carboxylate (4 parts) and ethyl 5-chloro-2-trifluoromethyl-[1,8]-naphthyridine-3-carboxylate (1 part). The material was used in the next stage without further purification. A sample was purified by chromatography (silica, hexane/ethyl acetate, 4:1 by volume) to give a pure sample of ethyl 7-chloro-2-trifluoromethyl-[1,8]-naphthyridine-3-carboxylate as a pale pink solid.
$^1$H NMR (CDCl$_3$) δ: 8.76 (1H, s), 8.30 (1H, d), 7.70 (1H, d), 4.50 (2H, q), 1.45 (3H, t). Molecular ion: (MH)$^+$305.

Stage 3

Preparation of ethyl 7-ethoxy-2-trifluoromethyl-[1,8]-naphthyridine-3-carboxylate To a stirred solution of ethyl 7-chloro-2-trifluoromethyl-[1,8]-naphthyridine-3-carboxylate (4.65 g) in ethanol (15 ml) at ambient temperature was added in portions sodium ethoxide (1.14 g). The mixture was stirred for 1 hour then heated to reflux for a further 16 hours. The mixture was cooled to ambient temperature, diluted with water (20 ml) and extracted with ethyl acetate (30 ml). The organic fraction was separated, washed with brine, dried over magnesium sulphate, filtered and evaporated under reduced pressure. The residual solid was purified by chromatography (silica, hexane/ethyl acetate) to give the required product, 3.15 g. $^1$H NMR (CDCl$_3$) δ: 8.60 (1H, s), 8.11 (1H, d), 7.15 (1H, d), 4.70 (2H, q), 4.47 (2H, q), 1.48 (3H, t), 1.43 (3H, t).

Stage 4

Preparation of 7-ethoxy-2-trifluoromethyl-[1,8]-naphthyridine-3-carboxylic acid

Ethyl 7-ethoxy-2-trifluoromethyl-[1,8]-naphthyridine-3-carboxylate (3.10 g) in ethanol (20 ml) was added aqueous 2M sodium hydroxide (10 ml) at ambient temperature. The mixture was stirred for 3 hours, acidified to pH 1 with aqueous 2M hydrochloric acid and extracted three times with ethyl acetate. The extracts were combined, washed with brine, dried over magnesium sulphate, filtered and evaporated under reduced pressure to give the required product, 2.86 g. $^1$H NMR (d$_6$-DMSO) δ: 8.98 (1H, s), 8.54 (1H, d), 7.36 (1H, d), 4.58 (2H, q), 1.43 (3H, t). Molecular ion: (MH)$^+$287.

Stage 5

In a similar procedure to Example 1, Stage 3, cyclohexane-1,3-dione was reacted with 7-ethoxy-2-trifluoromethyl-[1, 8]-naphthyridine-3-carboxylic acid to give the required product as a yellow solid. $^1$H NMR (CDCl$_3$) δ: 16.76 (1H, s), 8.01 (1H, d), 7.96 (1H, s), 7.09 (1H, d), 4.69 (2H, q), 2.34-2.94 (4H, bs), 2.07 (2H, quintet), 1.46 (3H, t). Molecular ion: (MH)$^+$371.

In a similar procedure to Example 1, Stage 3, the following compounds were prepared from the corresponding 7-alkoxynaphthyridine-3-carboxylic acids and cyclohexane-1,3-dione or bicyclo[3.2.1]octane-2,4-dione:

2-(7-methoxy-2-trifluoromethyl-[1,8]-naphthyridine-3-carbonyl)-cyclohexane-1,3-dione, yellow solid. $^1$H NMR (CDCl$_3$) δ: 16.69 (1H, s), 8.02 (1H, d), 7.98 (1H, s), 7.11 (1H, d), 4.21 (3H, s), 2.82 (2H, broad s), 2.42 (2H, broad s), 2.06 (2H, quintet).

3-(7-methoxy-2-trifluoromethyl-[1,8]-naphthyridine-3-carbony)-bicyclo[3.2.1]octane-2,4-dione, colourless solid. $^1$H NMR (CDCl$_3$) δ: 16.79 (1H, s), 8.03 (1H, d), 8.00 (1H, s), 7.12 (1H, d), 3.18 (3H, bs), 2.88 (1H, broad s), 2.23-2.02 (4H, m), 1.78-1.72 (2H, m).

2-(7-isopropoxy-2-trifluoromethyl-[1,8]-naphthyridine-3-carbonyl)-cyclohexane-1,3-dione, colourless solid. $^1$H NMR (CDCl$_3$) δ: 16.83 (1H, s), 7.99 (1H, d), 7.95 (1H, s), 7.04 (1H, d), 5.85 (1H, septet), 2.83 (2H, t), 2.43 (2H, t), 2.07 (2H, quintet).

2-(7-Allyloxy-2-trifluoromethyl-[1,8]-naphthyridine-3-carbonyl)-cyclohexane-1,3-dione, yellow solid. $^1$H NMR (CDCl$_3$) δ: 16.85 (1H, s), 8.09 (1H, d), 8.03 (1H, s), 7.20 (1H, d), 6.27-6.16 (1H, m), 5.55 (1H, m), 5.38 (1H, m), 5.20 (2H, m), 2.88 (2H, broad s), 2.47 (2H, broad s), 2.12 (2H, quintet).

2-(2-Methoxyethoxy)-2-trifluoromethyl-[1,8]-naphthyridine-3-carbonyl)-cyclohexane-1,3-dione, yellow solid. $^1$H NMR (CDCl$_3$) δ: 16.79 (1H, s), 8.04 (1H, d), 7.98 (1H, s), 7.20 (2H, d), 4.82-4.79 (2H, m), 3.84-3.82 (2H, m), 3.46 (3H, s), 2.83 (2H, t), 2.42 (3H, t), 2.07 (2H, quintet).

2-(7-(2,2,2-Trifluoroethoxy)-2-trifluoromethyl-[1,8]-naphthyridine-3-carbonyl)-cyclohexane-1,3-dione, yellow solid. $^1$H NMR (CDCl$_3$) δ: 16.70 (1H, s), 8.15 (1H, d), 8.04 (1H, s), 7.26 (2H, d), 5.06 (2H, q), 2.84 (2H, broad s), 2.43 (2H, broad s), 2.33 (2H, t), 2.08 (2H, quintet).

In a similar procedure to Example 1, Stage 3,7-phenoxy-2-trifluoromethylnaphthyridine-3-carboxylic acid was reacted with cyclohexane-1,3-dione to give 2-(7-phenoxy-2-trifluoromethyl-[1,8]-naphthyridine-3-carbonyl)-cyclohexane-1,3-dione. $^1$H NMR (CDCl$_3$) δ: 16.75 (1H, s), 8.18 (1H, d), 8.02 (1H, s), 7.45 (2H, m), 7.35 (1H, d), 7-27 (3H, m), 2.83 (2H, t), 2.33 (2H, t), 2.06 (2H, quintet). Molecular ion: (MH)$^+$429.

In a similar procedure to Example 1, Stage 3 the following compounds were prepared from 7-ethoxy-2-trifluoromethyl-[1,8]-naphthyridine-3-carboxylic acid and the corresponding ketones:

6-(7-ethoxy-2-trifluoromethyl-[1,8]-naphthyridine-3-carbonyl)-2,2,4,4-tetramethylcyclohexane-1,3,5-trione, yellow solid, $^1$H NMR (CDCl$_3$) δ: 17.32 (1H, s), 8.06 (1H, s), 8.05 (1H, d), 7.13 (1H, d), 4.70 (2H, q), 1.58 (6H, s), 1.48 (3H, t), 1.30 (6H, s), 1.32 (12H, s).

3-(7-ethoxy-2-trifluoromethyl-[1,8]-naphthyridine-3-carbonyl)-bicyclo[3.2.1]octane-2,4-dione, pale yellow solid. $^1$H NMR (CDCl$_3$) δ: 16.79 (1H, s), 8.02 (1H, d), 7.98 (1H, s), 7.09 (1H, d), 4.69 (2H, q), 3.17-2.91 (2H, m), 2.23-2.02 (4H, m), 1.77-1.72 (2H, m), 1.47 (3H, t).

2-ethyl-4-(7-ethoxy-2-trifluoromethyl-[1,8]-naphthyridine-3-carbony)-2,4-dihydropyrazol-3-one, pale yellow solid. $^1$H NMR (CDCl$_3$) δ: 8.31 (1H, s), 8.09 (1H, d), 7.35 (1H, s), 7.17 (1H, d), 4.71 (2H, q), 4.10 (2H, q), 1.49 (6H, dt).

EXAMPLE 3

Preparation of 2-ethyl-4-(7-hydroxy-2-trifluoromethyl-[1,8]-naphthyridine-3-carbony)-2,4-dihydropyrazol-3-one A suspension of 2-ethyl-4-(7-ethoxy-2-trifluoromethyl-[1,8]-naphthyridine-3-carbony)-2,4-dihydropyrazol-3-one (0.35 g) in ethanol (2 ml) and aqueous 2M hydrochloric acid (3 ml) was heated with stirring to 130° C. in a sealed vessel in a microwave oven for 15 minutes where upon a solution was obtained. This was diluted with water (20 ml), extracted with ethyl acetate and the organic fraction separated, dried over magnesium sulphate, filtered then evaporated under reduced pressure to give the required product as a pale yellow solid, 0.29 g. $^1$H NMR (d$_6$-DMSO) δ: 12.67 (1H, s), 8.43 (1H, s), 8.04 (1H, d), 7.53 (1H, s), 6.77 (1H, dd), 3.91 (2H, q), 1.26 (3H, t). Molecular ion: (MH)$^+$ 353.

The following compounds were prepared in a similar procedure to Example 3 from the corresponding 7-ethoxynaphthyridines:

2-(7-hydroxy-2-trifluoromethyl-[1,8]-naphthyridine-3-carbony)-cyclohexane-1,3-dione, colourless solid. $^1$H NMR (CDCl$_3$) δ: 15.87 (1H, bs), 12.68 (1H, bs), 8.25 (1H, s), 7.96 (2H, d), 6.77 (2H, d), 3.34 (2H, bs), 2.59 (2H, bs), 1.95 (2H, quintet).

3-(7-hydroxy-2-trifluoromethyl-[1,8]-naphthyridine-3-carbony)-bicyclo[3.2.1]octane-2,4-dione, colourless solid. $^1$H NMR (d$_6$-DMSO) δ: 12.66 (1H, s), 8.23 (1H, s), 7.98 (1H, d), 6.65 (1H, dd), 3.34-1.67 (8H, m).

6-(7-hydroxy-2-trifluoromethyl-[1,8]-naphthyridine-3-carbony)-2,2,4,4-tetramethylcyclohexane-1,3,5-trione, colourless solid. $^1$H NMR (d$_6$-DMSO) δ: 12.67 (1H, s), 8.23 (1H, s), 7.98 (1H, d), 6.75 (1H, d), 1.32 (12H, s).

EXAMPLE 4

Preparation of 6-fluoro-2-trifluoromethyl-[1,8]-naphthyridine-3-carbonyl)-cyclohexane-1,3-dione Stage 1

Preparation of 2-amino-5-bromopyridine-3-carboxaldehyde

To a stirred solution of 2-aminopyridine-3-carboxaldehyde (20 g) in acetonitrile (300 ml) was added N-bromosuccinimide (30.0 g) and the mixture was heated to reflux for 1.5 hours. The mixture was cooled to ambient temperature and the required product that precipitated from solution as a golden brown solid was filtered and sucked to dryness, 22.5 g.

$^1$H NMR (CDCl$_3$) δ: 9.83 (1H, s), 8.31 (1H, d), 8.24 (1H, d), 7.70 (2H, s).

Stage 2

Preparation of ethyl 6-bromo-2-trifluoromethyl-[1,8]-naphthyridine-3-carboxylate A mixture of 2-amino-5-bromopyridine-3-carboxaldehyde (15.0 g) and ethyl 4,4,4-trifluoroacetoacetate (10.8 ml) in ethanol (100 ml) containing piperidine (7.4 ml) was stirred and heated to reflux for 3 hours. The reaction mixture was cooled in an ice bath and the required product that precipitated as a yellow solid, 17.5 g, was filtered from solution, washed with a little cold ethanol and sucked to dryness.
$^1$H NMR (CDCl$_3$) δ: 9.30 (1H, d, 8.67 (1H, s), 8.52 (1H, d), 4.50 (2H, q), 1.45 (3H, t).

Stage 3

Preparation of ethyl 6-amino-2-trifluoromethyl-[1,8]-naphthyridine-3-carboxylate A mixture of ethyl 6-bromo-2-trifluoromethyl-[1,8]-naphthyridine-3-carboxylate (3.0 g), cesium carbonate (4.19 g), palladium acetate (0.096 g), benzophenone imine (1.7 ml) and 4,5-bis-diphenylphosphoranyl-9,9-dimethyl-9H-xanthene (0.372 g) in dioxane (5 ml) was heated with stirring to 150° C. in a sealed vessel in a microwave oven for 15 minutes then cooled to ambient temperature. Another batch of these reagents was processed in the same manner and the combined solutions combined and evaporated under reduced pressure to remove most of the solvent. The residue was treated with concentrated hydrochloric acid (15 ml), washed with ethyl acetate and the aqueous fraction separated. The organic fraction was further extracted with dilute hydrochloric acid (3×20 ml) and the aqueous acidic fractions combined, taken to pH 7 with aqueous sodium hydroxide then extracted with ethyl acetate (3×30 ml). The organic fractions were combined, washed with brine (2×20 ml), dried over magnesium sulphate, filtered and evaporated under reduced pressure to give an orange solid. The solid was purified by chromatography (silica, hexane/ethyl acetate) to give the required product as a yellow solid, 2.3 g. $^1$H NMR (CDCl$_3$) δ: 8.85 (1H, d), 8.44 (1H, s), 7.26 (1H, d), 4.47 (2H, q), 1.43 (3H, t).

Stage 4

Preparation of ethyl 6-fluoro-2-trifluoromethyl-[1,8]-naphthyridine-3-carboxylate To a stirred suspension of ethyl 6-amino-2-trifluoromethyl-[1,8]-naphthyridine-3-carboxylate (1.40 g) in tetrafluoroboric acid (1.3 ml, 48%) cooled in an icebath was added dropwise a solution of sodium nitrite (0.70 g) in water (0.9 ml). On complete addition, the mixture was stirred for a further 1 hour and the fine precipitate that had formed was filtered from solution, sucked to dryness then washed with hexane and dried under vacuum. The dry solid was heated until the diazonium tetrafluoroborate salt had fully decomposed producing a dark brown gum of the required fluoride. The gum was dissolved in ethyl acetate, washed with aqueous sodium hydrogen carbonate (2×30 ml), dried over magnesium sulphate, filtered and evaporated under reduced pressure. The residue was purified by chromatography (silica, hexane/diethyl ether) to provide the required product as a pale yellow solid. 0.80 g.
$^1$H NMR (CDCl$_3$) δ: 9.24 (1H, d), 8.77 (1H, s), 8.00 (1H, d), 4.54 (2H, q), 1.49 (3H, t).

Stage 5

Preparation of 6-fluoro-2-trifluoromethyl-[1,8]-naphthyridine-3-carboxylic acid

To a stirred suspension of ethyl 6-fluoro-2-trifluoromethyl-[1,8]-naphthyridine-3-carboxylate (0.73 g) in a mixture of ethanol (30 ml) and water (10 ml) was added lithium hydroxide hydrate (0.152 g) at ambient temperature. The mixture was stirred for 1 hour, diluted with ethyl acetate (50 ml), the organic fraction was separated and extracted with aqueous 2M sodium hydroxide (2×10 ml). The aqueous fractions were combined, taken to pH 1 with aqueous 2M hydrochloric acid and extracted into ethyl acetate (4×20 ml). The extracts were combined, dried over magnesium sulphate, filtered and evaporated under reduced pressure to give the required product as a pale yellow solid, 0.52 g. $^1$H NMR (CDCl$_3$) δ: 9.39 (1H, dd), 9.13 (1H, s), 8.60 (1H, dd).

Stage 6

To a stirred suspension of 6-fluoro-2-trifluoromethyl-[1,8]-naphthyridine-3-carboxylic acid (0.390 g) and cyclohexan-1,3-dione (0.190 g) in dry acetonitrile (10 ml) at ambient temperature was added N,N'-dicyclohexylcarbodiimide (0.344 g). The reaction mixture was stirred for 4 hours, filtered and the filtrate treated with triethylamine (0.290 ml) and acetone cyanohydrin (0.040 ml). The mixture was stirred for 16 hours, evaporated under reduced pressure and the residue purified by chromatography (silica, toluene/dioxane/ethanol/triethylamine/water, 20:8:4:4:1 by volume) to give the required product as the triethylamino salt. The salt was dissolved in ethyl acetate (30 ml), washed with aqueous 2M hydrochloric acid (2×5 ml), water (3×10 ml), dried over magnesium sulfate then evaporated under reduced pressure to give the required product as a pale brown solid, 0.130 g.
$^1$H NMR (CDCl$_3$) δ: 16.56 (1H, s), 9.15 (1H, d), 8.06 (1H, s), 7.86 (1H, dd), 2.86 (2H, t), 2.43 (2H, t), 2.09 (2H, quintet).

EXAMPLE 5

Preparation of 2-(6-fluoro-7-hydroxy-2-trifluoromethyl-[1,8]-naphthyridine-3-carbonyl)-cyclohexane-1,3-dione Stage 1

Preparation of ethyl 8-oxy-6-fluoro-2-trifluoromethyl-[1,8]-naphthyridine-3-carboxylate To a stirred solution of ethyl 6-fluoro-2-trifluoromethyl-[1,8]-naphthyridine-3-carboxylate (4.2 g) in dichloromethane (60 ml) containing urea hydrogen peroxide (9.2 g, 30% peroxide) at ambient temperature was added in portions trifluoroacetic anhydride (4.2 ml). During the addition the mixture started to reflux then gradually cooled to ambient temperature again. The mixture was stirred for 3 hours, washed with aqueous 0.1M sodium dithionite (20 ml), brine (20 ml) then dried over magnesium sulphate, filtered and evaporated under reduced pressure to give a solid. The solid was purified by chromatography (silica, hexane/ethyl acetate) to give the required product as a solid, 2.5 g. $^1$H NMR (CDCl$_3$) δ: 8.78 (1H, m), 8.76 (1H, s), 7.49 (1H, m), 4.51 (2H, q), 1.45 (3H, t).
In a similar procedure, ethyl 6-fluoro-5-methyl-2-trifluoromethyl-[1,8]-naphthyridine-3-carboxylate was oxidised to ethyl 6-fluoro-5-methyl-8-oxy-2-trifluoromethyl-[1,8]-naphthyridine-3-carboxylate, yellow solid, $^1$H NMR (CDCl$_3$) δ: 8.92 (1H, s), 8.88 (1H, d), 4.54 (2H, q), 2.68 (3H, d), 1.45 (3H, t). Molecular ion: (MH)$^+$319

Stage 2

Preparation of ethyl 7-chloro-6-fluoro-2-trifluoromethyl-[1,8]-naphthyridine-3-carboxylate and ethyl 5-chloro-6-fluoro-2-trifluoromethyl-[1,8]-naphthyridine-3-carboxylate To a stirred solution of ethyl 8-oxy-6-fluoro-2-trifluoromethyl-[1,8]-naphthyridine-3-carboxylate (2.41 g) in dry dichloromethane (100 ml) containing dry triethylamine (1.4 ml) cooled to 10° C. was added dropwise at ambient temperature phosphoryl chloride (0.930 ml). On complete addition, the mixture was stirred for 30 minutes at ambient temperature then heated to reflux for 4 hours. The mixture was cooled to ambient temperature, washed with saturated aqueous sodium hydrogen carbonate then brine and dried over magnesium sulphate, filtered and evaporated under reduced pressure. The residue was purified by chromatography (silica, hexane/ethyl acetate) to give ethyl 7-chloro-6-fluoro-2-trifluoromethyl-[1,8]-naphthyridine-3-carboxylate, 0.45 g, $^1$H NMR (CDCl$_3$) δ: 8.73 (1H, s), 8.02 (1H, d), 4.49 (2H, q), 1.45 (3H, t) and ethyl 5-chloro-6-fluoro-2-trifluoromethyl-[1,8]-naphthyridine-3-carboxylate, 0.300 g. $^1$H NMR (CDCl$_3$) δ: 8.76 (1H, s), 8.02 (1H, d), 4.50 (2H, q), 1.44 (3H, t).

In a similar procedure, ethyl 6-fluoro-5-methyl-8-oxy-2-trifluoromethyl-[1,8]-naphthyridine-3-carboxylate was reacted to give ethyl 7-chloro-6-fluoro-5-methyl-2-trifluoromethyl-[1,8]-naphthyridine-3-carboxylate, yellow solid, $^1$H NMR (CDCl$_3$) δ: 8.82 (1H, s), 4.52 (2H, q), 2.76 (3H, d), 1.46 (3H, t). Molecular ion: (MH)$^+$337

Stage 3

Preparation of 7-ethoxy-6-fluoro-2-trifluoromethyl-[1,8]-naphthyridine-3-carboxylic acid A solution of ethyl 7-chloro-6-fluoro-2-trifluoromethyl-[1,8]-naphthyridine-3-carboxylate (0.45 g) in ethanol (4 ml) containing sodium ethoxide (0.143 g) was sealed in a tube and heated with stirring in a microwave oven at 100° C. for 10 minutes then allowed to cool to ambient temperature. The solution was diluted with ethanol (2 ml) and aqueous 2M sodium hydroxide (2 ml) was added then the mixture was stirred for 2 hours at ambient temperature. The solution was acidified to pH1 with 2M hydrochloric acid, extracted with ethyl acetate (2×10 ml), dried over magnesium sulphate, filtered then evaporated under reduced pressure to give the required product as a pale yellow solid, 0.40 g. $^1$H NMR (d$_6$-DMSO) δ: 8.95 (1H, s), 8.45 (1H, d), 4.66 (2H, q), 1.46 (3H, t).

Stage 4

In a similar procedure to Example 1, Stage 3, cyclohexane-1.3-dione and 6-fluoro-7-ethoxy-2-trifluoromethyl-[1,8]-naphthyridine-3-carboxylic acid were reacted to give 6-fluoro-7-ethoxy-2-trifluoromethyl-[1,8]-naphthyridine-3-carbonyl)-cyclohexane-1,3-dione as a pale yellow solid. $^1$H NMR (CDCl$_3$) δ: 16.72 (1H, s), 7.93 (1H, s), 7.67 (1H, d), 4.78 (2H, q), 2.83 (2H, t), 2.42 (3H, t), 2.07 (2H, quintet), 1.53 (3H, t).

Stage 5

A suspension of 2(6-fluoro-7-ethoxy-2-trifluoromethyl-[1,8]-naphthyridine-3-carbonyl)-cyclohexane-1,3-dione (0.12 g) in aqueous 2M hydrochloric acid (3 ml) and ethanol (2 ml) was heated with stirring in a sealed tube in a microwave oven at 130° C. for 15 minutes. The mixture was cooled to ambient temperature, filtered from solution, washed with water, sucked to dryness then washed with hexane to give the required product as a colourless solid, 0.082 g.
$^1$H NMR (CDCl$_3$) δ: 16.56 (1H, bs), 13.04 (1H, bs), 8.18 (1H, s), 7.84 (1H, d), 3.06 (4H, bs), 2.63 (2H, bs).

EXAMPLE 6

Preparation of 2-(7-methylmercapto-2-trifluoromethyl-[1,8]-naphthyridine-3-carbonyl)-cyclohexane-1,3-dione

Stage 1

Preparation of ethyl 7-methylmercapto-2-trifluoromethyl-[1,8]-naphthyridine-3-carboxylate A solution of ethyl 7-chloro-6-fluoro-2-trifluoromethyl-[1,8]-naphthyridine-3-carboxylate (1.0 g) in acetonitrile (3 ml) containing sodium thiomethoxide 0.65 g) was sealed in a tube and heated with stirring in a microwave oven at 130° C. for 10 minutes then allowed to cool to ambient temperature. The solution was diluted with ethyl acetate (20 ml), washed with brine (10 ml), dried over magnesium sulphate, filtered then evaporated under reduced pressure. The residue was purified by chromatography (silica, hexane/ethyl acetate, 4:1 by volume) to give the required product as a colourless solid, 0.49 g.
$^1$H NMR (CDCl$_3$) δ: 8.62 (1H, s), 7.98 (1H, d), 7.47 (1H, d), 4.47 (2H, q), 2.82 (3H, s), 1.44 (3H, t).

Stage 2

Preparation of 7-methylmercapto-2-trifluoromethyl-[1,8]-naphthyridine-3-carboxylic acid To a stirred solution of ethyl 7-methylmercapto-2-trifluoromethyl-[1,8]-naphthyridine-3-carboxylate (0.46 g) in ethanol (7.5 ml) containing water (2.5 ml) was added sodium hydroxide (0.12 g) at ambient temperature. The mixture was stirred for 3 hours, acidified to pH 1 with 2M hydrochloric acid and extracted with ethyl acetate. The organic fraction was separated, washed with brine, dried over magnesium sulfate, filtered and evaporated under reduced pressure to give the required product, 0.38 g. $^1$H NMR (d$_6$-DMSO) δ: 9.02 (1H, s), 8.44 (1H, d), 7.76 (1H, d), 2.71 (3H, s).

Stage 3

In a similar procedure to Example 1, Stage 3, cyclohexan-1,3-dione was reacted with 7-methylmercapto-2-trifluoromethyl-[1,8]-naphthyridine-3-carboxylic acid to give 2-(7-methylmercapto-2-trifluoromethyl-[1,8]-naphthyridine-3-carbonyl)-cyclohexane-1,3-dione as a yellow solid. $^1$H NMR (CDCl$_3$) δ: 16.75 (1H, s), 7.97 (1H, s), 7.89 (1H, d), 7.42 (1H, d), 2.83 (2H, t), 2.81 (3H, s), 2.42 (2H, t), 2.07 (2H, quintet).

EXAMPLE 7

Preparation of 2-(8-oxy-2-trifluoromethyl-[1,8]-naphthyridine-3-carbony)-cyclohexane-1,3-dione To a stirred solution of 2-(2-trifluoromethyl-[1,8]-naphthyridine-3-carbony)-cyclohexane-1,3-dione (0.500 g) in dry dichloromethane (10 ml) containing urea hydrogen peroxide (0.078 g, 30% peroxide) was added trifluoroacetic anhydride (0.115 ml). The mixture was stirred at ambient temperature for 20 hours, washed with water (20 ml) and evaporated under reduced pressure. The residue was purified by chromatography (silica, toluene:dioxane, ethanol:triethylamine:water, ratio by volume 20:8:4:4:1 increasing the ethanol content of the eluent until the desired product was eluted) to give the triethylamine salt of the required product. The salt was dissolved in dichloromethane (15 ml) and acidified with aqueous 2M hydrochloric acid (5 ml). The organic fraction was separated, washed with water (10 ml), dried over magnesium sulfate then evaporated under reduced pressure to give the required product as an orange solid, 0.17 g.
$^1$H NMR (CDCl$_3$) δ: 16.42 (1H, s), 8.81 (1H, dd), 8.16 (1H, s), 7.69 (1H, dd), 7.49 (1H, dd), 2.86 (2H, t), 2.43 (2H, t), 2.09 (2H, quintet). Molecular ion: (MH)$^+$337.

EXAMPLE 8

Preparation of 2-(7-(but-2-ynyloxy)-2-trifluoromethyl-[1,8]-naphthyridine-3-carbony)-cyclohexane-1,3-dione A mixture of 2-(7-hydroxy-2-trifluoromethyl-[1,8]-naphthyridine-3-carbony)-cyclohexane-1,3-dione (0.100 g) in chloroform (10 ml) containing but-2-ynyl bromide (0.051 ml) and silver carbonate (0.155 g) were stirred and heated to reflux for 17 hours. The reaction was cooled to ambient temperature, diluted with ethyl acetate (20 ml) then washed with water (2×10 ml), dried over magnesium sulfate, filtered and evaporated under reduced pressure to give a gum. The gum was purified by chromatography (silica, hexane/ethyl acetate) to give 3-(but-2-ynyloxy)-2-(7-[but-2-ynyloxy]-[1,8]-naphthyridin-3-carbonyl)-cyclohex-2-enone (0.050 g). This was dissolved in ethanol containing 2M aqueous hydrochloric acid and stirred at ambient temperature for 10 minutes then diluted with ethyl acetate (15 ml), washed with water (2×10 ml), dried over magnesium sulfate, filtered and evaporated under reduced pressure to give the required product, 0.026 g. $^1$H NMR (CDCl$_3$) δ: 16.70 (1H, s), 7.99 (1H, d), 7.92 (1H, s), 7.11 (1H, d), 5.18 (2H, q), 2.76 (2H, t), 2.35 (3H, t), 2.00 (2H, quintet), 1.85 (3H, t). Molecular ion: (MH)$^+$405.

EXAMPLE 9

Preparation of 2-(2-trifluoromethyl-[1,8]-naphthyridine-3-carbony)-1,3-dicyclopropylpropan-1,3-dione A mixture of 1-cyclopropyl-3-(2-trifluoromethyl-[1,8]-naphthyridin-3-yl)-propane-1,3-dione (0.446 g) and magnesium ethoxide (0.196 g) was suspended in dry tetrahydrofuran (8 ml) under an atmosphere of nitrogen and heated to reflux for 3 hours with stirring then cooled to ambient temperature. To the mixture was added cyclopropanecarbonyl chloride (0.13 ml) then the reaction mixture was stirred at ambient temperature for a further 18 hours. Additional cyclopropanecarbonyl chloride (0.15 ml) was added and the mixture heated to reflux with stirring for 2 hours, cooled to ambient temperature then stored for 2 days. The solvent was evaporated under reduced pressure and the residue acidified with aqueous 2M hydrochloric acid then extracted twice with ethyl acetate. The extracts were combined, washed with water and brine then dried over magnesium sulfate, filtered and evaporated under reduced pressure. The residue was re-dissolved in ethyl acetate, extracted three times with aqueous sodium hydrogen carbonate and the aqueous fractions were combined, washed with ethyl acetate then the aqueous fraction was acidified with aqueous 2M hydrochloric acid. The aqueous, acidic fraction was extracted three times with ethyl acetate, the extracts combined, dried over magnesium sulfate, filtered and evaporated under reduced pressure to give the required product as a brown gum, 0.168 g. $^1$H NMR (CDCl$_3$) indicated that the material exists as a tautomeric mixture (ca. 1:1) of geometric enol isomers δ: 18.60 (1H, s), 17.35 (1H, s), 9.32 (2H broad s), 8.61 (1H, s), 8.39 (1H, dd), 8.29 (2H, m), 7.72 (2H, m), 2.30 (1H, m), 1.92 (2H, m), 1.62 (1H, m), 1.45 (2H, m), 1.22 (4H, m), 1.06 (2H, m), 0.94 (2H, m), 0.82 (4H, m), 0.58 (2H, bs).

EXAMPLE 10

Preparation of 2-(2-trifluoromethyl-[1,8]-naphthyridine-3-carbony)-3-cyclopropyl-3-oxopropionitrile Stage 1

To a stirred suspension of 2-trifluoromethyl-[1,8]-naphthyridine-3-carboxylic acid (2.0 g) in dry dichloromethane (40 ml) at ambient temperature under an atmosphere of nitrogen was added N,N-dimethylformamide (0.05 ml, catalyst) followed by oxalyl chloride (1.3 ml). The mixture was heated to reflux with stirring for 3 hours, cooled to ambient temperature then evaporated under reduced pressure to give 2-trifluoromethyl-[1,8]-naphthyridine-3-carbonyl chloride.

Stage 2

To a solution of tert. butyl 1-cyclopropyl-1-oxopropionate (1.53 g) in dry methanol (48 ml) under an atmosphere of nitrogen was added magnesium turnings (0.20 g) and carbon tetrachloride (0.1 ml). The mixture was stirred at ambient temperature until the magnesium had dissolved (ca. 3 hours). The solvent was evaporated under reduced pressure then toluene (ca. 50 ml) was added and evaporated under reduced pressure to remove any residual methanol. Further toluene (30 ml) was added and to this was added a suspension of the product from Stage 1 in toluene (30 ml) followed by triethylamine (1.3 ml). The mixture was stirred at ambient temperature for 18 hours, evaporated under reduced pressure, water added then it was extracted twice with ethyl acetate. The organic fractions were combined, washed with water then brine and dried over magnesium sulfate, filtered and evaporated under reduced pressure to give a red-brown oil. The oil was dissolved in toluene (60 ml) containing p.toluene sulfonic acid (0.02 g) then heated to reflux for 3 hours with stirring, cooled to ambient temperature then stored for 18 hours. The solution was purified by eluting down a column of silica with ethyl acetate to give an oil, 1.16 g, containing 1-cyclopropyl-3 (2-trifluoromethyl-[1,8]-naphthyridin-3-yl)-propane-1,3-dione [$^1$NMR (CDCl$_3$) δ: 9.29 (1H, m), 8.50 (1H, s), 8.36 (1H, dd), 7.71 (1H, m), 6.04 (1H, s), 1.79 (1H, m), 1.28 (2H, m), 1.08 (2H, m)] and an impurity of methyl 2-trifluoromethyl-[1,8]-naphthyridine 3-carboxylate [$^1$H NMR (CDCl$_3$) δ: 9.32 (1H, m), 8.78 (1H, s), 8.39 (1H, dd), 7.71 (1H, m), 4.04 (3H, s)]. The material was used in Stage 3 without further purification.

Stage 3

The product from Stage 2 (0.50 g) was dissolved in tetrahydrofuran (4 ml) containing acetic acid (0.19 g) with stirring and cooled to 5° C. then a solution of N,N-dimethylformamide dimethylacetal (0.38 g) in tetrahydrofuran (1 ml) was added dropwise. The mixture was stirred for 30 minutes at 5° C., allowed to warm to ambient temperature, stirred for a further 30 minutes then poured into water. The mixture was extracted twice with ethyl acetate, the extracts combined, washed with brine, dried over magnesium sulfate, filtered and evaporated under reduced pressure to give a dark red-brown gum. The gum was purified by chromatography (silica, ethyl acetate then 10% methanol in ethyl acetate) to give 1-cyclopropyl-2-(1-dimethylaminomethylidene)-3-(2-trifluoromethyl-[1,8]-naphthyridin-3-yl)-propane-1,3-dione as a dark-red gum, (0.33 g). $^1$H NMR (CDCl$_3$) δ: 9.26 (1H, m), 8.29 (1H, s), 8.26 (1H, dd), 7.65 (1H, m), 7.48 (1H, bs), 3.27 (3H bs), 2.88 (3H, bs), 2.03 (1H, bs), 0.90 (2H, bs), 0.62 (2H, bs).

Stage 4

To a stirred solution of 1-cyclopropyl-2-(1-dimethylaminomethylidene)-3-(2-trifluoromethyl-[1,8]-naphthyridin-3-yl)-propane-1,3-dione (0.33 g) in ethanol (10 ml) was added hydroxylamine hydrochloride (0.069 g). The mixture was stirred at ambient temperature for 3 hours, evaporated under reduced pressure and water added. The mixture was extracted three times with dichloromethane, the extracts combined, washed with water then brine, dried over magnesium sulfate, filtered and evaporated under reduced pressure to give a pale pink solid. The solid was purified by chromatography (silica, ethyl acetate) to give (5-cyclopropyl-isoxazo-4-yl)(2-trifluoromethyl-[1,8]-naphthyridin-3-yl)ketone as a beige solid, 0.21 g. $^1$H NMR (CDCl$_3$) δ: 9.35 (1H, m), 8.41 (1H, s), 8.36 (1H, dd), 8.15 (1H, s), 7.75 (1H, m), 2.67 (1H, m), 1.41 (2H, m), 1.28 (2H, m).

Stage 5

The product from Stage 4 (0.10 g) was dissolved in dichloromethane (3 ml) containing triethylamine (0.1 ml) and stirred at ambient temperature for 3 hours then evaporated under reduced pressure. The residue was dissolved in water, acidified with aqueous 2M hydrochloric acid and extracted twice with ethyl acetate. The extracts were combined, washed with water then brine, dried over magnesium sulfate, filtered and evaporated under reduced pressure. The residue was washed with a little diethyl ether and filtered to give the required product as a yellow solid, 0.052 g. $^1$H NMR (CDCl$_3$) δ: 9.36 (1H, m), 8.57 (1H, s), 8.39 (1H, dd), 7.74 (1H, m), 2.40 (1H, m), 1.54 (2H, m), 1.40 (2H, m).

EXAMPLE 11

Preparation of 2-(8-methyl-7-oxo-7,8-dihydro-2-trifluoromethyl-[1,8]-naphthyridine-3-carbony)-cyclohexane-1,3-dione To a stirred suspension of 2-(7-hydroxy-2-trifluoromethyl-[1,8]-naphthyridine-3-carbony)-cyclohexane-1,3-dione (0.200 g) in dry 1,2-dimethoxyethane (10 ml) cooled to 0° C. was added drop-wise a solution of n-butyl lithium (0.875 ml of 1.6M solution in hexanes). On complete addition, the resulting suspension was stirred for 5 mins at 0° C. followed addition of methyl iodide (0.345 ml). The suspension was then allowed to warm to ambient temperature, dry N,N-dimethylformamide (5 ml) was added and the resulting solution was stirred for a further 2 hours. The mixture was diluted with ethyl acetate (20 ml), washed with aqueous 2M hydrochloric acid (5 ml) then water (2×10 ml). The organic extract was separated, dried over magnesium sulfate, filtered and evaporated under reduced pressure to afford the required product, 0.153 g.
$^1$H NMR (CDCl$_3$) δ: 16.80 (1H, s), 7.74 (1H, s), 7.65 (1H, d), 6.88 (1H, d), 4.77 (2H, t), 3.96 (3H, s), 2.83 (2H, t), 2.43 (3H, t), 2.07 (2H, quintet). Molecular ion: (MH)$^+$367.

In a similar procedure to Example 11, the following compounds were made from 2-(7-hydroxy-2-trifluoromethyl-[1,8]-naphthyridine-3-carbony)-cyclohexane-1,3-dione and a suitable alkylating agent:

2-(8-Benzyl-7-oxo-7,8-dihydro-2-trifluoromethyl-[1,8]-naphthyridine-3-carbony)-cyclohexane-1,3-dione (from benzyl bromide), $^1$H NMR (CDCl$_3$) δ: 16.80 (1H, s), 7.72 (1H, s), 7.64-7.61 (3H, m), 7.31-7.21 (3H, m), 6.88 (1H, d), 5.71 (2H, s), 2.83 (2H, t), 2.43 (3H, t), 2.07 (2H, quintet), Molecular ion: (MH)$^+$443.

2-(8-(But-2-ynyl)-7-oxo-7,8-dihydro-2-trifluoromethyl-[1,8]-naphthyridine-3-carbony)-cyclohexane-1,3-dione (from but-2-ynyl bromide), $^1$H NMR (CDCl$_3$) δ: 16.80 (1H, s), 7.75 (1H, s), 7.65 (1H, d), 6.88 (1H, d), 5.24 (2H, q), 2.84 (2H, t), 2.44 (3H, t), 2.08 (2H, quintet), 1.76 (3H, t), Molecular ion: (MH)$^+$405.

2-{8-(Tetrahydrofuran-2-yl-methyl)-7-oxo-7,8-dihydro-2-trifluoromethyl-[1,8]-naphthyridine-3-carbony}-cyclohexane-1,3-dione, yellow solid, (from tetrahydrofuran-2-ylmethyl bromide, heated at 65° C. for 40 hours), $^1$H NMR (CDCl$_3$) δ: 16.80 (1H, s), 7.72 (1H, s), 7.63 (1H, d), 6.87 (1H, d), 4.80 (1H, dd), 4.58-4.52 (1H, mt), 4.37 (1H, m), 3.43 (1H, dd), 3.74 (1H, dd), 2.83 (2H, t), 2.44 (2H, t), 2.07 (2H, m), 2.06-1.74 (3H, m), 0.88-0.83 (1H, m), Molecular ion: (MH)$^+$436.

2-{8-(2-Methoxyethyl)-7-oxo-7,8-dihydro-2-trifluoromethyl-[1,8]-naphthyridine-3-carbony}-cyclohexane-1,3-dione (from 2-methoxyethyl bromide, heated at 65° C. for 16 hours),
$^1$H NMR (CDCl$_3$) δ:16.80 (1H, s), 7.73 (1H, s), 7.63 (1H, d), 6.86 (1H, d), 4.77 (2H, t), 3.79 (2H, t), 3.40 (3H, s), 2.83 (2H, t), 2.44 (3H, t), 2.08 (2H, m). Molecular ion: (MH)$^+$411.

2-{8-(cyclopropylmethyl)-7-oxo-7,8-dihydro-2-trifluoromethyl-[1,8]-naphthyridine-3-carbony}-cyclohexane-1,3-dione (from cyclopropylmethyl bromide), $^1$H NMR (CDCl$_3$) δ: 16.80 (1H, s), 7.74 (1H, s), 7.66 (1H, d), 6.86 (1H, d), 4.40 (2H, d), 2.85 (2H, t), 2.45 (2H, t), 2.08 (2H, m), 1.42 (1H, m), 0.50 (4H, m).

2-{8-isobutyl-7-oxo-7,8-dihydro-2-trifluoromethyl-[1,8]-naphthyridine-3-carbony}-cyclohexane-1,3-dione (from cyclopropylmethyl bromide), $^1$H NMR (CDCl$_3$) δ:16.80 (1H, s), 7.73 (1H, s), 7.63 (1H, d), 6.88 (1H, d), 4.38 (2H, d), 2.85 (2H, m), 2.45 (2H, t), 2.32 (1H, m), 2.08 (2H, m), 0.96 (6H, d).

2-{8-(2-phenoxyethyl)-7-oxo-7,8-dihydro-2-trifluoromethyl-[1,8]-naphthyridine-3-carbony}-cyclohexane-1,3-dione (from 2-phenoxyethyl chloride), $^1$H NMR (CDCl$_3$) δ:16.80 (1H, s), 7.76 (1H, s), 7.66 (1H, d), 7.25 (2H, m), 6.95 (3H, m), 6.86 (1H, d), 4.95 (2H, t), 4.36 (2H, t), 2.85 (2H, t), 2.42 (2H, t), 2.06 (2H, m).

2-{8-(2-ethoxyethyl)-7-oxo-7,8-dihydro-2-trifluoromethyl-[1,8]-naphthyridine-3-carbony}-cyclohexane-1,3-dione (from 2-ethoxyethyl chloride), $^1$H NMR (CDCl$_3$) δ: 16.80 (1H, s), 7.76 (1H, s), 7.64 (1H, d), 6.86 (1H, d), 4.78 (2H, t), 3.84 (2H, t), 3.60 (2H, q), 2.85 (2H, t), 2.44 (2H, t), 2.08 (2H, m), 1.16 (3H, t).

2-{8-(2-phenylethyl)-7-oxo-7,8-dihydro-2-trifluoromethyl-[1,8]-naphthyridine-3-carbonyl}-cyclohexane-1,3-dione (from 2-phenylethyl chloride), $^1$H NMR (CDCl$_3$) δ: 16.80 (1H, s), 7.76 (1H, s), 7.66 (1H, d), 7.30 (5H, m), 6.88 (1H, d), 4.70 (2H, m), 3.05 (2H, m), 2.85 (2H, t), 2.45 (2H, t), 2.08 (2H, m).

2-{8-allyl-7-oxo-7,8-dihydro-2-trifluoromethyl-[1,8]-naphthyridine-3-carbony}-cyclohexane-1,3-dione (from allyl bromide), $^1$H NMR (CDCl$_3$) δ:16.80 (1H, s), 7.76 (1H, s), 7.66 (1H, d), 6.86 (1H, d), 6.00 (1H, m), 5.32 (1H, m), 5.15 (2H, m), 2.85 (2H, t), 2.44 (2H, t), 2.08 (2H, m).

2-{8-n.-propyl-7-oxo-7,8-dihydro-2-trifluoromethyl-[1,8]-naphthyridine-3-carbonyl}-cyclohexane-1,3-dione (from n.-propyl bromide), $^1$H NMR (CDCl$_3$) δ:16.80 (1H, s), 7.74 (1H, s), 7.63 (1H, d), 6.86 (1H, d), 4.48 (2H, t), 2.82 (2H, m), 2.45 (2H, t), 2.08 (2H, m), 1.80 (2H, m), 1.00 (3H, t).

2-{8-(2-fluorophenylmethyl)-7-oxo-7,8-dihydro-2-trifluoromethyl-[1,8]-naphthyridine-3-carbony}-cyclohexane-1,3-dione (from 2-fluorophenylmethyl chloride), $^1$H NMR (CDCl$_3$) δ:16.80 (1H, s), 7.76 (1H, s), 7.68 (1H, d), 7.20 (2H, m), 7.00 (2H, m), 6.80 (1H, d), 5.78 (2H, s), 2.80 (2H, t), 2.40 (2H, t), 2.06 (2H, m).

2-{8-(2-fluoroethyl)-7-oxo-7,8-dihydro-2-trifluoromethyl-[1,8]-naphthyridine-3-carbony}-cyclohexane-1,3-dione (from 2-fluoroethyliodide), $^1$H NMR (CDCl$_3$) δ:16.80 (1H, s), 7.80 (1H, s), 7.68 (1H, d), 6.86 (1H, d), 4.95-4.75 (4H, m), 2.85 (2H, m), 2.42 (2H, t), 2.08 (2H, m).

2-{8-isopropyl-7-oxo-7,8-dihydro-2-trifluoromethyl-[1,8]-naphthyridine-3-carbonyl}-cyclohexane-1,3-dione (from isopropyl bromide), $^1$H NMR (CDCl$_3$) δ:16.80 (1H, s), 7.70 (1H, s), 7.68 (1H, d), 6.80 (1H, d), 5.86 (1H, m), 2.85 (2H, m), 2.45 (2H, t), 2.08 (2H, m), 1.68 (6H, d).

2-{8-(1-methylpentyl)-7-oxo-7,8-dihydro-2-trifluoromethyl-[1,8]-naphthyridine-3-carbony}-cyclohexane-1,3-dione (from 1-methylpent-1-yl bromide), $^1$H NMR (CDCl$_3$) δ:7.70 (1H, s), 7.66 (1H, d), 6.80 (1H, br s), 5.85 (1H, bs), 2.85 (2H, t), 2.45 (2H, t), 2.08 (2H, m), 1.65 (3H, m), 1.80 (2H, m), 1.30-1.20 (4H, m), 0.80-0.90 (3H, m).

2-{8-cyclopentyl-7-oxo-7,8-dihydro-2-trifluoromethyl-[1,8]-naphthyridine-3-carbonyl}-cyclohexane-1,3-dione (from cyclopentyl bromide), $^1$H NMR (CDCl$_3$) δ:7.70 (1H, s), 7.58 (1H, d), 6.82 (1H, d), 5.98 (1H, m), 2.84 (2H, m), 2.45 (2H, m), 2.36 (2H, m), 2.18-2.05 (4H, m), 1.95 (2H, m), 1.70 (2H, m).

2-{8-(3,3-dimethyl-2-oxo-butyl)-7-oxo-7,8-dihydro-2-trifluoromethyl-[1,8]-naphthyridine-3-carbony}-cyclohexane-1,3-dione (from 1-bromo-3,3-dimethylbutan-2-one), $^1$H NMR (CDCl$_3$) δ: 16.80 (1H, s), 7.76 (1H, s), 7.69 (1H, d), 6.86 (1H, d), 5.50 (2H, s), 2.82 (2H, t), 2.43 (2H, t), 2.06 (2H, m), 1.35 (9H, s).

2-{8-(2-phenyl-2-oxo-ethyl)-7-oxo-7,8-dihydro-2-trifluoromethyl-[1,8]-naphthyridine-3-carbony}-cyclohexane-1,3-dione (from 1-phenyl-2-bromoethanone), $^1$H NMR (CDCl$_3$) δ:16.80 (1H, s), 7.76 (1H, s), 7.69 (1H, d), 6.86 (1H, d), 5.50 (2H, s), 2.82 (2H, t), 2.43 (2H, t), 2.06 (2H, m), 1.35 (9H, s).

2-{8-methoxymethyl-7-oxo-7,8-dihydro-2-trifluoromethyl-[1,8]-naphthyridine-3-carbony}-cyclohexane-1,3-dione (from methoxymethyl bromide), $^1$H NMR (CDCl$_3$) δ: 16.70 (1H, s), 7.75 (1H, s), 7.68 (1H, d), 6.86 (1H, d), 5.96 (2H, s), 3.52 (3H, s), 2.84 (2H, t), 2.46 (2H, t), 2.08 (2H, m).

2-{8-(carbamoylmethyl)-7-oxo-7,8-dihydro-2-trifluoromethyl-[1,8]-naphthyridine-3-carbony}-cyclohexane-1,3-dione (from 2-bromoacetamide), $^1$H NMR (CDCl$_3$) δ: 8.30 (1H, s), 8.04 (1H, d), 7.68 (1H, s), 7.18 (1H, s), 6.90 (1H, d), 4.92 (2H, s), 2.55 (4H, m), 1.95 (2H, m).

2-{8-(2,2-difluoroethyl)-7-oxo-7,8-dihydro-2-trifluoromethyl-[1,8]-naphthyridine-3-carbony}-cyclohexane-1,3-dione (from difluoroethyl iodide), $^1$H NMR (CDCl$_3$) δ: 7.78 (1H, s), 7.68 (1H, d), 6.42-6.12 (1H, m), 4.95 (2H, m), 2.85 (2H, t), 2.46 (2H, t), 2.08 (2H, m).

2-{8-cyanomethyl)-7-oxo-7,8-dihydro-2-trifluoromethyl-[1,8]-naphthyridine-3-carbony}-cyclohexane-1,3-dione (from cyanomethyl chloride), $^1$H NMR (CDCl$_3$) δ:16.60 (1H, s), 7.73 (1H, s), 7.66 (1H, d), 6.89 (1H, d), 5.40 (2H, s), 2.84 (2H, t), 2.42 (2H, t), 2.08 (2H, m).

2-{8-(4,4-difluorobut-3-enyl)-7-oxo-7,8-dihydro-2-trifluoromethyl-[1,8]-naphthyridine-3-carbony}-cyclohexane-1,3-dione (from 4,4-difluorobut-3-enyl bromide), $^1$H NMR (CDCl$_3$) δ:16.70 (1H, s), 7.76 (1H, s), 7.66 (1H, d), 6.86 (1H, d), 4.56 (2H, t), 4.35-4.20 (1H, m), 2.85 (2H, m), 2.55-2.40 (3H, m), 2.08 (2H, m).

2-{8-(3,3,3-trifluoropropyl)-7-oxo-7,8-dihydro-2-trifluoromethyl-[1,8]-naphthyridine-3-carbony}-cyclohexane-1,3-dione (from 3,3,3-trifluoropropyl bromide), $^1$H NMR (CDCl$_3$) δ:16.70 (1H, s), 7.68 (1H, s), 7.68 (1H, d), 6.88 (1H, d), 4.78 (2H, m), 2.85 (2H, t), 2.65 (2H, m), 2.45 (2H, m), 2.08 (2H, m).

2-{8-(5-oxo-pyrrolidin-2-ylmethyl)-7-oxo-7,8-dihydro-2-trifluoromethyl-[1,8]-naphthyridine-3-carbony}-cyclohexane-1,3-dione (from 5-oxo-pyrrolidin-2-ylmethyl bromide), $^1$H NMR (CDCl$_3$) δ:16.70 (1H, s), 7.80 (1H, s), 7.68 (1H, d), 6.88 (1H, d), 6.24 (1H, bs), 4.75 (1H, dd), 4.58 (1H, dd), 4.15 (1H, m), 2.85 (2H, m), 2.50-2.40 (3H, m), 2.35-2.20 (2H, m), 2.12-1.98 (3H, m).

2-{8-(5-oxo-tetrahydrofuran-2-ylmethyl)-7-oxo-7,8-dihydro-2-trifluoromethyl-[1,8]-naphthyridine-3-carbony}-cyclohexane-1,3-dione (from 5-oxo-tetrahydrofuran-2-ylmethyl bromide), $^1$H NMR (CDCl$_3$) δ:16.70 (1H, s), 7.84 & 7.78 (1H, 2×s), 7.70 (1H, 2×d), 6.85 (1H, 2×d), 6.40 and 6.18 (1H, 2×t), 4.75 & 4.50 (2H, 2×m), 2.85-2.65 (4H, m), 2.45 (2H, m), 2.08 (2H, m).

2-{8-(5-methylisoxazol-3-ylmethyl)-7-oxo-7,8-dihydro-2-trifluoromethyl-[1,8]-naphthyridine-3-carbony}-cyclohexane-1,3-dione (from 5-methylisoxazol-3-ylmethyl bromide), $^1$H NMR (CDCl$_3$) δ:16.70 (1H, s), 7.78 (1H, s), 7.88 (1H, d), 6.89 (1H, d), 6.00 (1H, s), 5.75 (2H, s), 2.84 (2H, t), 2.44 (2H, t), 2.34 (3H, s), 2.08 (2H, m).

EXAMPLE 12

Preparation of 2-[7-(1-fluoroethyl)-2-trifluoromethyl-[1,8]-naphthyridine-3-carbony]-cyclohexane-1,3-dione Stage 1: Preparation of ethyl 7-acetyl-2-trifluoromethyl-[1,8]-naphthyridine-3-carboxylate To a stirred mixture of ethyl 2-trifluoromethyl-[1,8]-naphthyridine-3-carboxylate (11 g) in dichloromethane (250 ml) and water (250 ml) containing sulphuric acid (2.7 ml), silver nitrate (0.86 g) and pyruvic acid (10.4 ml) was added ammonium persulfate (12 g) then the mixture was heated to 40° C. for 1 hour. Further ammonium persulfate (12 g) was gradually added, the reaction heated for an additional 30 minutes then further ammonium persulfate (10 g) gradually added. The mixture was heated for 1 hour, cooled to ambient temperature and the organic phase separated. The aqueous phase was extracted with dichloromethane (100 ml), the extracts combined, dried over magnesium sulfate, filtered and evaporated under reduced pressure. The residue was purified by chromatography (silica, hexane/ethyl acetate, 4:1 by volume) to give the required product as a yellow solid, 4.5 g. $^1$H NMR (CDCl$_3$) δ: 8.79 (1H, s), 8.50 (1H, d), 8.41 (1H, d), 4.51 (2H, q), 2.97 (3H, s), 1.46 (3H, t). Molecular ion: (MH)$^+$313.

Alternative preparation of ethyl 7-acetyl-2-trifluoromethyl-[1,8]-naphthyridine-3-carboxylate To a stirred mixture of ethyl 7-chloro-2-trifluoromethyl-[1,8]-naphthyridine-3-carboxylate (25 g) in toluene (350 ml) and palladium bis(triphenylphosphine)dichloride (2.8 g) was added tributyl (1-ethoxyvinyl)stannane (36 ml) under nitrogen and the mixture heated to 70° C. for 16 hours then for a further 2 hours at 80° C. The mixture was cooled to ambient temperature, washed with aqueous potassium fluoride solution [10 g KF in water (100 ml)] then the mixture was filtered and the organic phase separated. The toluene solution was washed with water (three times) then treated with aqueous hydrochloric acid (6M, 250 ml) and stirred at ambient temperature for 1 hour. The organic phase was separated, washed with water then brine and dried over magnesium sulfate, filtered then evaporated under reduced pressure. The residual oil was purified by chromatography (silica; isohexane/ethyl acetate; 4:1 by volume) to give the required product as a yellow solid, 10 g, identical to the previously described material.

Stage 2: Preparation of ethyl 7-(1-hydroxyethyl)-2-trifluoromethyl-[1,8]-naphthyridine-3-carboxylate To a stirred solution of ethyl 7-acetyl-2-trifluoromethyl-[1,8]-naphthyridine-3-carboxylate (3.0 g) in ethanol (50 ml) cooled to 0° C. was added sodium borohydride (0.127 g). The mixture was stirred for 1 hour, acidified with aqueous 2M hydrochloric acid (10 ml), extracted with ethyl acetate (60 ml) and the extract washed with brine (30 ml). The extract was dried over magnesium sulfate, filtered and evaporated under reduced pressure to leave the required product as a yellow solid, 2.8 g. $^1$H NMR (CDCl$_3$) δ: 8.87 (1H, s), 8.36 (1H, d), 7.73 (1H, d), 5.19 (1H, quintet), 4.50 (2H, q), 4.19 (1H, d), 1.64 (3H, d), 1.45 (3H, t). Molecular ion: (MH)$^+$315.

Stage 3: Preparation of ethyl 7-(1-fluoroethyl)-2-trifluoromethyl-[1,8]-naphthyridine-3-carboxylate To a stirred solution of ethyl 7-(1-hydroxyethyl)-2-trifluoromethyl-[1,8]-naphthyridine-3-carboxylate (2.75 g) in dry dichloromethane (80 ml) was added N,N-diethylaminosulfur trifluoride (2.9 ml) at ambient temperature. On complete addition, the mixture was stirred for 16 hours, washed with saturated aqueous sodium hydrogen carbonate solution and the aqueous fraction separated and re-extracted with further dichloromethane (50 ml). The extracts were combined, dried over magnesium sulfate, filtered and evaporated under reduced pressure. The residue was purified by chromatography (silica, hexane/ethyl acetate) to give the required product as a pale yellow solid, 1.44 g. $^1$H NMR (CDCl$_3$) δ: 8.77 (1H, s), 8.43 (1H, d), 7.96 (1H, dd), 5.97 (1H, m), 4.50 (2H, q), 1.84 (3H, dd), 1.45 (3H, t). Molecular ion: (MH)$^+$317.

Stage 4: Preparation of 7-(1-fluoroethyl)-2-trifluoromethyl-[1,8]-naphthyridine-3-carboxylic acid To a stirred solution of ethyl 7(1-fluoroethyl)-2-trifluoromethyl-[1,8]-naphthyridine-3-carboxylate (1.43 g) in ethanol (100 ml) and water (30 ml) was added lithium hydroxide monohydrate (0.38 g) at ambient temperature. The mixture was stirred for 16 hours, acidified with aqueous 2M hydrochloric acid (20 ml), extracted with ethyl acetate (2×100 ml) and the extracts combined, washed with brine (100 ml), dried over magnesium sulfate, filtered and evaporated under reduced pressure to give the required product as a colourless solid, 1.26 g. $^1$H NMR (CDCl$_3$) δ: 9.19 (1H, s), 8.83 (1H, d), 8.02 (1H, d), 6.01 (1H, m), 1.75 (3H, dd).

Stage 5

To a stirred solution of 7-(1-fluoroethyl)-2-trifluoromethyl-[1,8]-naphthyridine-3-carboxylic acid (0.4 g) in dry acetonitrile (8 ml) containing cyclohexane 1,3-dione (0.188 g) and 3 A molecular sieves (0.2 g) was added N,N'-dicyclohexylcarbodiimide (0.341 g) at ambient temperature. The mixture was stirred for 2 hours, filtered and the filtrate collected. To the stirred filtrate was added 3 A molecular sieves (0.2 g) followed by triethylamine (0.572 ml) and acetone cyanhydrin (0.030 ml). The mixture was stirred for 3 hours, filtered and the filtrate evaporated under reduced pressure. The residue was purified by chromatography (silica, toluene:dioxane, ethanol:triethylamine:water, ratio by volume 20:8:4:4:1) to give the triethylamine salt of the required product. The salt was dissolved in ethyl acetate (30 ml), acidified with aqueous 2M hydrochloric acid (10 ml) and washed with brine (20 ml), dried over magnesium sulfate, filtered and evaporated under reduced pressure to give the required product as a pale orange solid, (0.265 g). $^1$H NMR (CDCl$_3$) δ: 16.61 (1H, s), 8.32 (1H, d), 8.11 (1H, s), 7.89 (1H, dd), 5.95 (1H, m), 2.83 (2H, bs), 2.42 (2H, bs), 2.07 (2H, m), 1.82 (3H, dd). Molecular ion: (MH)$^+$383. In a similar procedure to Example 12, Stage 5 the following compounds were prepared from 7(1-fluoroethyl)-2-trifluoromethyl-[1,8]-naphthyridine-3-carboxylic acid and the corresponding carbonyl derivatives:

3-(7-(1-fluoroethyl)-2-trifluoromethyl-[1,8]-naphthyridine-3-carbonyl)-bicyclo[3.2.1]octane-2,4-dione, yellow solid. $^1$H NMR (CDCl$_3$) δ: 8.33 (1H, d), 8.14 (1H, s), 7.90 (1H, dd), 5.95 (2H, dq), 3.91 (1H, bs), 2.87 (1H, bs), 2.24-1.65-(6H, m), 1.83 (3H, dd). Molecular ion: (MH)$^+$408.

5-[7-(1-Fluoro-ethyl)-2-trifluoromethyl-[1,8]naphthyridine-3-carbonyl]-spiro[2.5]octane-4,6-dione, pale orange gum. $^1$H NMR δ: 8.37 (1H, d), 8.17 (1H, s), 7.91 (1H, d), 5.97 (1H, dq), 2.90 (1H, bs), 2.53 (1H, bs), 2.02-1.90 (2H, m), 1.81 (3H, dd), 1.73 (1H, bs), 1.24-1.05 (2H, m), 0.73 (1H, bs); Molecular ion: (MH)$^+$409.08.

4-[7-(1-Fluoro-ethyl)-2-trifluoromethyl-[1,8]naphthyridine-3-carbonyl]-2-methyl-2,4-dihydro-pyrazol-3-one, pale orange gum.
$^1$H NMR δ: 8.49 (1H, s), 8.44 (1H, d), 8.00 (1H, d), 7.36 (1H, s), 5.98 (1H, dq), 3.76 (3H, s), 1.84 (3H, dd).

EXAMPLE 13

Preparation of 2-[7-(1,1-difluoroethyl)-2-trifluoromethyl-[1,8]-naphthyridine-3-carbony]-cyclohexane-1,3-dione Stage 1: Preparation of ethyl 7-(1,1-difluoroethyl)-2-trifluoromethyl-[1,8]-naphthyridine-3-carboxylate A stirred solution of ethyl 7-acetyl-2-trifluoromethyl-[1,8]-naphthyridine-3-carboxylate (0.625 g) in N,N-di(2-methoxyethyl)aminosulfur trifluoride (1.85 ml) was heated to 60° C. for 2 hours then cooled to ambient temperature. The mixture was diluted with dichloromethane (50 ml), washed with aqueous sodium hydrogen carbonate solution (3×15 ml), then water (20 ml). The organic phase was separated, dried over magnesium sulfate, filtered and evaporated under reduced pressure. The residue was purified by chromatography (silica, hexane/ethyl acetate) to give the required product as a yellow oil, 0.40 g. $^1$H NMR (CDCl$_3$) δ: 8.80 (1H, d), 8.51 (1H, d), 8.08 (1H, d), 4.51 (2H, q), 2.25 (3H, t), 1.46 (3H, t). Molecular ion: (MH)$^+$335

Stage 2

In a similar procedure to Example 12, Stage 4 ethyl 7-(1,1-difluoroethyl)-2-trifluoromethyl-[1,8]-naphthyridine-3-carboxylate was hydrolysed to give 7-(1,1-difluoroethyl)-2-trifluoromethyl-[1,8]-naphthyridine-3-carboxylic acid as a colourless solid. $^1$H NMR (CDCl$_3$) δ: 9.26 (1H, s), 8.96 (1H, d), 8.20 (1H, d), 2.17 (3H, t).

Stage 3

In a similar procedure to Example 12, Stage 5,7-(1,1-difluoroethyl)-2-trifluoromethyl-[1,8]-naphthyridine-3-carboxylic acid was reacted with cyclohexane-1,3-dione to give 2-[7-(1,1-difluoroethyl)-2-trifluoromethyl-[1,8]-naphthyridine-3-carbonyl]-cyclohexane-1,3-dione as a pale yellow solid.
$^1$H NMR (CDCl$_3$) δ: 16.56 (1H, s), 8.43 (1H, d), 8.18 (1H, s), 8.06 (1H, d), 2.87 (2H, bs), 2.46 (2H, bs), 2.28 (3H, t), 2.12 (2H, quintet). Molecular ion: (MH)$^+$401.

EXAMPLE 14

Preparation of 2-[7-(1-methoxyethyl)-2-trifluoromethyl-[1,8]-naphthyridine-3-carbony]-cyclohexane-1,3-dione Stage 1

To a stirred solution of ethyl [7-(1-hydroxyethyl)-2-trifluoromethyl-[1,8]-naphthyridine-3-carboxylate (1.15 g) in dry dichloromethane (20 ml) containing triethylamine (0.770 ml) at ambient temperature was added methane sulfonyl chloride (0.344 ml). The mixture was stirred for 1 hour then washed with water (10 ml) and brine (10 ml). The organic phase was dried over magnesium sulfate, filtered and evaporated under reduced pressure to give ethyl [7-(1-methanesulfonyloxyethyl)-2-trifluoromethyl-[1,8]-naphthyridine-3-carboxylate as a brown oil, 1.2 g, that was used in the next Stage without further purification.

Stage 2

The product from Stage 1 (1.2 g) was dissolved in methanol (5 ml) with stirring at ambient temperature and sodium methoxide (0.31 g) was added. The mixture was stirred at ambient temperature for 30 minutes. Lithium hydroxide monohydrate (0.48 g) was added to the mixture which was stirred for a further 1 hour. The reaction was acidified with aqueous 2M hydrochloric acid (10 ml), extracted with ethyl acetate (30 ml) and the organic phase separated, washed with water (10 ml), brine (10 ml) then dried over magnesium sulfate, filtered and evaporated under reduced pressure. The residue was taken into diethyl ether, filtered and the filtrate evaporated under reduced pressure to give 7-(1-methoxyethyl)-2-trifluoromethyl-[1,8]-naphthyridine-3-carboxylic acid as a yellow solid.

Stage 3

To a stirred mixture of 7-(1-methoxyethyl)-2-trifluoromethyl-[1,8]-naphthyridine-3-carboxylic acid (0.600 g), 1,3-cyclohexanedione (0.271 g) and 3 A molecular sieves (0.2 g) in acetonitrile (10 ml) was added N,N'-dicyclohexylcarbodiimide (0.593 g) at ambient temperature. The reaction was stirred for 1 hour, filtered and to the filtrate were added further 3 A molecular sieves (0.2 g) followed by triethylamine (0.83 ml) and acetone cyanhydrin (0.050 ml). The mixture was stirred at ambient temperature for 2 hours, filtered, evaporated under reduced pressure and the residue purified by chromatography (silica; toluene:dioxane, ethanol:triethylamine:water, ratio by volume 20:8:4:4:1) to give the triethylamine salt of the required product. The salt was dissolved in ethyl acetate (20 ml), acidified with aqueous 2M hydrochloric acid (8 ml) and washed with brine (10 ml), dried over magnesium sulfate, filtered and evaporated under reduced pressure to give the required product as a yellow solid, (0.190 g). $^1$H NMR (CDCl$_3$) δ: 16.69 (1H, s), 8.28 (1H, d), 8.09 (1H, s), 7.87 (1H, dd), 4.76 (1H, q), 3.36 (3H, s), 2.84 (2H, t), 2.42 (2H, t), 2.08 (2H, quintet), 1.56 (3H, d). Molecular ion: (MH)$^+$395.

EXAMPLE 15

Preparation of 2-[6-fluoro-7-methyl-2-trifluoromethyl-[1,8]-naphthyridine-3-carbony]-cyclohexane-1,3-dione Stage 1

Preparation of ethyl 6-fluoro-7-methyl-2-trifluoromethyl-[1,8]-naphthyridine-3-carboxylate To a stirred solution of ethyl 7-chloro-6-fluoro-2-trifluoromethyl-[1,8]-naphthyridine-3-carboxylate (0.332 g) in toluene (6 ml) containing palladium acetate (0.023 g), potassium phosphate (0.318 g) and dicyclohexyl-(2',6'-dimethoxybiphenyl-2-yl)phosphane (0.062 g) was added methyl boronic acid (0.227 g). The mixture was heated to reflux for 4 hours, cooled to ambient temperature and diluted with ethyl acetate (20 ml). The organic phase was washed with water (20 ml), brine (20 ml), dried over magnesium sulfate, filtered and evaporated under reduced pressure. The residue was purified by chromatography (silica; hexane/ethyl acetate) to provide the required product as a pale yellow solid, (0.185 g). $^1$H NMR (CDCl$_3$) δ: 8.67 (1H, s), 7.85 (1H, d), 4.49 (2H, q), 2.86 (3H, d), 1.43 (3H, t). Molecular ion: (MH)$^+$303.
The following compounds were similarly prepared from ethyl 7-chloro-6-fluoro-2-trifluoromethyl-[1,8]-naphthyridine-3-carboxylate and the corresponding boronic acid:
Ethyl 7-ethyl-6-fluoro-2-trifluoromethyl-[1,8]-naphthyridine-3-carboxylate, colourless solid, $^1$H NMR (CDCl$_3$) δ: 8.67 (1H, s), 7.85 (1H, d), 4.50 (2H, q), 3.19 (2H, q), 1.47 (3H, t), 1.45 (3H, t). Molecular ion: (MH)$^+$317.
Ethyl 7-n.butyl-6-fluoro-2-trifluoromethyl-[1,8]-naphthyridine-3-carboxylate, yellow oil, $^1$H NMR (CDCl$_3$) δ: 8.67 (1H, s), 7.85 (1H, d), 4.49 (2H, q), 3.17-3.14 (2H, m), 1.98 (2H, quintet), 1.45-1.43 (3H, m), 1.44 (3H, t), 0.98 (3H, t). Molecular ion: (MH)$^+$345.
Ethyl 6-fluoro-7-(2-methylpropyl)-2-trifluoromethyl-[1,8]-naphthyridine-3-carboxylate, colourless solid, $^1$H NMR (CDCl$_3$) δ: 8.67 (1H, s), 7.85 (1H, d), 4.49 (2H, q), 3.04 (2H, dd), 2.43-2.33 (1H, m), 1.44 (3H, t), 1.02 (6H, d). Molecular ion: (MH)$^+$345.

Ethyl 6-fluoro-7-[(E)-prop-1-enyl]-2-trifluoromethyl-[1,8]-naphthyridine-3-carboxylate. $^1$H NMR (CDCl$_3$) δ: 8.62 (1H, s), 7.84 (1H, d), 7.67-7.58 (1H, m), 6.96-6.91 (1H, m), 4.48 (2H, q), 2.09 (3H, double doublet), 1.44 (3H, t).

In a similar procedure to Example 15, Stage 1, ethyl 5-chloro-6-fluoro-2-trifluoromethyl-[1,8]-naphthyridine-3-carboxylate was reacted with methyl boronic acid to give ethyl 6-fluoro-5-methyl-2-trifluoromethyl-[1,8]-naphthyridine-3-carboxylate. $^1$H NMR (CDCl$_3$) δ: 9.11 (1H, s), 8.86 (1H, s), 4.52 (2H, q), 2.71 (3H, d), 1.46 (3H, t). Molecular ion: (MH)$^+$303.

Similarly, ethyl 7-chloro-6-fluoro-5-methyl-2-trifluoromethyl-[1,8]-naphthyridine-3-carboxylate was reacted with methyl boronic acid to give ethyl 5,7-dimethyl-6-fluoro-2-trifluoromethyl-[1,8]-naphthyridine-3-carboxylate, $^1$H NMR (CDCl$_3$) δ: 8.78 (1H, s), 4.50 (2H, q), 2.84 (3H, d), 2.68 (3H, d), 1.46 (3H, t). Molecular ion: (MH)$^+$317.

Stage 2

Preparation of 6-fluoro-7-methyl-2-trifluoromethyl-[1,8]-naphthyridine-3-carboxylic acid To a stirred solution of ethyl 6-fluoro-7-methyl-2-trifluoromethyl-[1,8]-naphthyridine-3-carboxylate (0.185 g) in ethanol (12 ml) containing water (3 ml) was added lithium hydroxide monohydrate (0.080 g). The mixture was stirred for 2 hours at ambient temperature, acidified with 2M aqueous hydrochloric acid (6 ml) and extracted with ethyl acetate (2×15 ml). The organic extracts were combined, washed with brine (2×10 ml), dried over magnesium sulfate, filtered and evaporated under reduced pressure to provide the required product as a colourless solid, 0.156 g. $^1$H NMR (d$_6$-DMSO) δ: 14.2 (1H, bs), 9.05 (1H, s), 8.48 (1H, d), 2.75 (3H, d).

In a similar procedure to Example 16, Stage 2, ethyl 6-fluoro-5-methyl-2-trifluoromethyl-[1,8]-naphthyridine-3-carboxylate was hydrolysed to give 6-fluoro-5-methyl-2-trifluoromethyl-[1,8]-naphthyridine-3-carboxylic acid, $^1$H NMR (CDCl$_3$+d$_4$-MeOH) δ: 8.86 (1H, s), 8.76 (1H, s), 2.53 (3H, s).

Similarly, the following compounds were prepared from their corresponding esters:

6-Fluoro-7-(2-methylpropyl)-2-trifluoromethyl-[1,8]-naphthyridine-3-carboxylic acid, $^1$H NMR (d$_6$-DMSO) δ: 9.01 (1H, s), 8.45 (1H, d), 2.90 (2H, m), 2.26-2.19 (1H, m), 0.92 (6H, d).

7-(Cyclopropyl)-6-fluoro-2-trifluoromethyl-[1,8]-naphthyridine-3-carboxylic acid, yellow solid, $^1$H NMR (d$_6$-DMSO) δ: δ: 8.92 (1H, s), 8.40 (1H, d), 2.50 (1H, m), 1.22 (4H, m).

7-(n.-Butyl)-6-fluoro-2-trifluoromethyl-[1,8]-naphthyridine-3-carboxylic acid, $^1$H NMR (d$_6$-DMSO) δ: δ: 8.77 (1H, s), 7.93 (1H, d), 3.17-3.12 (2H, m), 1.91-1.83 (2H, m), 1.53-1.43 (2H, m), 0.98 (3H, t).

6-Fluoro-[7-(E) styryl]-2-trifluoromethyl-[1,8]-naphthyridine-3-carboxylic acid, yellow solid. Molecular ion: (MH)$^+$ 363.

7-Methoxymethyl-2-trifluoromethyl-[1,8]-naphthyridine-3-carboxylic acid, colourless solid. Molecular ion: (MH)$^+$ 287.

Stage 3

In a similar procedure to Example 1, Stage 3, 6-fluoro-7-methyl-2-trifluoromethyl-[1,8]-naphthyridine-3-carboxylic acid was reacted with 1,3-cyclohexanedione to give the required product as a pale yellow solid.
$^1$H NMR (CDCl$_3$) δ: 8.02 (1H, s), 7.77 (1H, d), 2.85 (5H, m), 2.42 (2H, m), 2.46 (2H, bs), 2.08 (2H, q). Molecular ion: (MH)+369.

In a similar procedure to Stage 3, the following compounds were prepared from 1,3-cyclohexanedione and the corresponding naphthyridine carboxylic acids:

2-[7-Cyclopropyl-6-fluoro-2-trifluoromethyl-[1,8]-naphthyridine-3-carbony]-cyclohexane-1,3-dione, $^1$H NMR (CDCl$_3$) δ: 7.97 (1H, s), 7.79 (1H, d), 2.86-2.37 (5H, m), 2.07 (2H, quintet), 1.59-1.57 (2H, m), 1.29-1.24 (2H, m).

2-[7-(n.-Butyl)-6-fluoro-2-trifluoromethyl-[1,8]-naphthyridine-3-carbony]-cyclohexane-1,3-dione, $^1$H NMR (CDCl$_3$)) δ: 8.01 (1H, s), 7.74 (1H, d), 3.14 (2H, td), 2.78 (2H, bs), 2.47 (2H, bs), 2.07 (2H, qi), 1.87 (2H, qi), 1.52-1.43 (2H, m), 0.98 (3H, t).

6-fluoro-7-(prop-1-enyl)-2-trifluoromethyl-[1,8]-naphthyridine-3-carbony]-cyclohexane-1,3-dione, $^1$H NMR (CDCl$_3$) δ: 16.67 (1H, s), 7.97 (1H, s), 7.75 (1H, d), 7.63-7.52 (1H, m), 6.92 (1H, d), 2.84 (2H, t), 2.42 (2H, t), 2.09-2.07 (5H, m).

Similarly, the following compounds were prepared from 6-fluoro-7-methyl-2-trifluoromethyl-[1,8]-naphthyridine-3-carboxylic acid and the corresponding diones:

From 8-oxa-bicyclo[3.2.1]octane-2,4-dione, 3-[6-fluoro-7-methyl-2-trifluoromethyl-[1,8]-naphthyridine-3-carbony]-8-oxa-bicyclo[3.2.1]octane-2,4-dione $^1$H NMR (CDCl$_3$) δ: 8.15 (1H, s), 7.80 (1H, d), 4.90 (1H, d), 4.55 (1H, d), 2.87 (3H, d), 1.90-2.50 (4H, m).

From cyclopentane 1,3-dione, 2-[6-fluoro-7-methyl-2-trifluoromethyl-[1,8]-naphthyridine-3-carbony]-cyclopentane-1,3-dione, yellow solid
$^1$H NMR (CDCl$_3$) δ: 8.30 (1H, s), 7.82 (1H, d), 2.93 (2H, broad s), 2.87 (3H, d), 2.58 (2H, broad s). Molecular ion: (MH)$^+$355.

From 2,2,4,4-tetramethylcyclohexane-1,3,5-trione, 6-(6-fluoro-7-methyl-2-trifluoromethyl-[1,8]-naphthyridine-3-carbony)-2,2,4,4-tetramethylcyclohexane-1,3,5-trione, yellow solid, $^1$H NMR (CDCl$_3$) δ:17.19 (1H, s), 8.11 (1H, s), 7.79 (1H, d), 2.86 (3H, d), 1.60 (6H, s), 1.30 (6H, s). Molecular ion: (MH)$^+$439.

From bicyclo[3.2.1]octane-2,4-dione, 3-[6-fluoro-7-methyl-2-trifluoromethyl-[1,8]-naphthyridine-3-carbony]-bicyclo[3.2.1]octane-2,4-dione, yellow solid, $^1$H NMR (CDCl$_3$) δ: 16.64 (1H, s), 8.05 (1H, s), 7.76 (1H, d), 3.19 (1H, t), 2.87 (1H, t), 2.85 (3H, d), 2.30-2.02 (4H, m), 1.80-1.74 (2H, m); Molecular ion: (MH)$^+$395.

In a similar procedure to Example 1, Stage 3, 6-fluoro-5-methyl-2-trifluoromethyl-[1,8]-naphthyridine-3-carboxylic acid was reacted with the corresponding diones to give the following compounds:

2-[6-Fluoro-5-methyl-2-trifluoromethyl-[1,8]-naphthyridine-3-carbony]-cyclohexane-1,3-dione, $^1$H NMR (CDCl$_3$) δ: 9.06 (1H, s), 8.19 (1H, s), 2.81 (2H, bs), 2.62 (3H, d), 2.46 (2H, bs), 2.08 (2H, q). Molecular ion: (MH)$^+$ 369.

3-[6-Fluoro-5-methyl-2-trifluoromethyl-[1,8]-naphthyridine-3-carbony]-bicyclo[3.2.1]octane-2,4-dione $^1$H NMR (CDCl$_3$) δ: 16.60 (1H, s), 9.07 (1H, s), 8.23 (1H, s), 3.21-3.19 (1H, m), 2.89-2.86 (1H, m), 2.63 (3H, d), 2.28-2.04 (4H, m), 2.04-1.80 (2H, m). Molecular ion: (MH)$^+$395.

EXAMPLE 16

Preparation of 2-[6-hydroxy-2-trifluoromethyl-[1,8]-naphthyridine-3-carbony]-cyclohexane-1,3-dione A solution of 2-[6-fluoro-2-trifluoromethyl-[1,8]-naphthyridine-3-carbony]-cyclohexane-1,3-dione (0.080 g) in aqueous 2M sodium hydroxide (5 ml) was heated in a microwave oven at 150° C. for 10 minutes, cooled to ambient temperature, acidified with aqueous 2M hydrochloric acid and extracted with ethyl acetate (2×10 ml). The extracts were combined, washed with brine, dried over magnesium sulfate, filtered and evaporated under reduced pressure to provide the required product as a brown solid, 0.070 g. $^1$H NMR (CDCl$_3$) δ: 16.06 (1H, s), 10.28 (1H, s), 8.41 (1H, d), 7.55 (1H, s), 7.05 (1H, d), 2.37 (2H, bs), 1.90 (2H, bs), 1.57 (2H, quintet).

EXAMPLE 17

Preparation of salts of 2-[7-(1-fluoroethyl)-2-trifluoromethyl-[1,8]-naphthyridine-3-carbony]-cyclohexane-1,3-dione General Procedure for Salt Preparations
To a solution of 2-[7-(1-fluoroethyl)-2-trifluoromethyl-[1,8]-naphthyridine-3-carbony]-cyclohexane-1,3-dione (0.030 g) in a dry solvent (ca 0.5 ml) was added a suitable base (1 equivalent). The solution formed was allowed to evaporate over 72 hours to provide the required salt.
Examples of Salts Prepared:
Triethylamine salt (dichloromethane as solvent); pale yellow solid.
Sodium salt (from sodium methoxide in methanol); colourless solid.
Magnesium salt (from magnesium oxide in methanol); colourless solid.
Calcium salt (from calcium oxide in methanol); colourless solid.

EXAMPLE 18

Preparation of isobutyric acid 2-(7-ethoxy-2-trifluoromethyl-[1,8]-naphthyridine-3-carbonyl)-3-oxo-cyclohex-1-enyl ester To a stirred solution of 2-(7-ethoxy-2-trifluoromethyl-[1,8]-naphthyridine-3-carbonyl)-cyclohexane-1,3-dione (Example 2, 0.38 g) in dry dichloromethane (8 ml) containing triethylamine (0.28 ml) was added isobutyryl chloride (0.107 g) at 0° C. The mixture was stirred for 16 hours, washed with water, dried over magnesium sulfate, filtered and evaporated under reduced pressure. The residue was purified by chromatography (silica, hexane/ethyl acetate) to give the required product, 0.29 g. $^1$H NMR (CDCl$_3$) δ: 8.30 (1H, s), 8.08 (1H, d), 7.12 (1H, d), 4.68 (2H, q), 2.78 (2H, t), 2.60 (1H, m), 2.51 (2H, t), 2.16 (2H, quintet), 1.47 (3H, t), 1.13 (6H, d). Molecular ion: (MH)$^+$451.
In a similar procedure, the following compounds were prepared from 2-(6-fluoro-7-methyl-2-trifluoromethyl-[1,8]-naphthyridine-3-carbonyl)-cyclohexane-1,3-dione and the corresponding acid chloride:
Isobutyric acid 2-(6-fluoro-7-methyl-2-trifluoromethyl-[1,8]-naphthyridine-3-carbonyl)-3-oxo-cyclohex-1-enyl ester, $^1$H NMR (CDCl$_3$) δ: 8.35 (1H, S), 7.82 (1H, d), 2.85 (3H, d), 2.65 (1H, t) 2.50 (2H, t), 2.15 (2H, quintet), 1.16 (6H, d). Molecular ion: (MH)$^+$439.
n-Octanoic acid 2-(6-fluoro-7-methyl-2-trifluoromethyl-[1,8]-naphthyridine-3-carbonyl)-3-oxo-cyclohex-1-enyl ester, $^1$H NMR (CDCl$_3$) δ: δ: 8.32 (1H, s), 7.80 (1H, d), 2.84 (3H, d), 2.78 (2H, t), 2.48 (2H, t), 2.40 (2H, t), 2.12 (2H, quintet), 1.25 (10H, bs), 0.82 (3H, t).
2,2-Dimethylacetic acid 2-(6-fluoro-7-methyl-2-trifluoromethyl-[1,8]-naphthyridine-3-carbonyl)-3-oxo-cyclohex-1-enyl ester, $^1$H NMR (CDCl$_3$) δ: 8.38 (1H, s), 7.84 (1H, d), 2.85 (3H, d), 2.78 (2H, t), 2.50 (2H, t), 2.15 (2H, quintet), 1.20 (9H, s). Molecular ion: (MH)$^+$453.

EXAMPLE 19

Preparation of 2-[2-(methoxymethyl)-7-trifluoromethyl-[1,8]-naphthyridine-3-carbony]-cyclohexane-1,3-dione To a stirred suspension of 2(methoxymethyl)-7-trifluoromethyl-[1,8]-naphthyridine-3-carboxylic acid (0.34 g) in dry acetonitrile (1.4 ml) was added 4-nitrophenol (0.166 g) followed by N,N'-dicyclohexylcarbodiimide (0.270 g) at ambient temperature. The mixture was stirred for 3 hours, 3 A molecular sieves (ca. 100 mg) were added then cyclohexane-1,3-dione (0.134 g) was added followed by dry triethylamine (0.30 g) and acetone cyanhydrin (0.005 g). The mixture was stirred for a further 18 hours, filtered, evaporated under reduced pressure and the residue purified by reverse phase HPLC to give the required product (0.045 g) as a gum.
$^1$H NMR (CDCl$_3$) δ: 8.40 (1H, d), 8.00 (1H, s), 7.85 (1H, d), 4.88 (2H, s), 3.25 (3H, m), 2.85-2.45 (6H, m).

EXAMPLE 20

Preparation of 2-[2-chlorodifluoromethyl-7-methyl [1,8]-naphthyridine-3-carbony]-cyclohexane-1,3-dione To a stirred suspension of 2-chlorodifluoromethyl-7-methyl [1,8]-naphthyridine-3-carboxylic acid (0.25 g) in dry dichloromethane (10 ml) containing N,N-dimethylformamide (1 drop, catalyst) was added oxalyl chloride (0.14 g) at ambient temperature. The dark green solution was stirred for 1 hour, evaporated under reduced pressure to give a green solid. The solid was dissolved in dry acetonitrile (10 ml) with stirring and cyclohexane1,3-dione (0.12 g) and dry triethylamine (0.38 ml) were added. The mixture was stirred at ambient temperature for 2 hours then further triethylamine (0.26 ml) was added followed by acetone cyanhydrin (2 drops, catalyst). The mixture was stirred for 18 hours, acidified with dilute aqueous hydrochloric acid then extracted with ethyl acetate (3 times). The extracts were combined, washed with water, dried over magnesium sulfate, filtered and evaporated under reduced pressure to give a brown gum. The gum was purified by reverse phase HPLC to afford the required product as a yellow foam, 0.12 g. $^1$H NMR (CDCl$_3$) δ: 16.70 (1H, s), 8.12-8.14 (1H, d), 8.00 (1H, s), 7.50-7.52 (1H, d), 2.88 (3H, s), 2.82-2.86 (2H, t), 2.40-2.44 (2H, t), 2.04-2.08 (2H, m).

EXAMPLE 21

Preparation of 2-[6-fluoro-2-(methoxydifluoromethyl)-7-methyl-[1,8]-naphthyridine-3-carbony]-cyclohexane-1,3-dione Stage 1

In a similar procedure to Example 1, Stage 1, 2-amino-5-fluoro-6-methylpyridinyl-3-carboxaldehyde and ethyl 4,4-difluoro-4-iodoacetoacetate were reacted to give ethyl 2-difluoroiodomethyl-6-fluoro-7-methyl-[1,8]-naphthyridine-3-carboxylate, yellow solid, $^1$H NMR (CDCl$_3$) δ: 8.48 (1H, s), 7.81 (1H, d), 4.46-4.52 (2H, q), 2.84 (3H, d), 1.44-1.50 (3H, t).

Stage 2

Preparation of ethyl 2-[6-fluoro-2-(methoxydifluoromethyl)-7-methyl [1,8]-naphthyridine-3-carboxylate To stirred solution of ethyl 2-difluoroiodomethyl-6-fluoro-7-methyl-[1,8]-naphthyridine-3-carboxylate (1.64 g) in dry methanol (20 ml) under an atmosphere of nitrogen was added silver tetrafluoroborate (1.17 g). The reaction flask was covered with aluminium foil to protect the contents from light then the reaction mixture was heated to reflux for 2 hours. The mixture was cooled to ambient temperature, poured into dilute aqueous ammonia, filtered, evaporated under reduced pressure to remove excess methanol then diluted with water. The mixture was extracted with dichloromethane (three times), the extracts were combined and washed with water then dried over magnesium sulfate, filtered and evaporated under reduced pressure to give the required product as a dark yellow oil that partially solidified on storing, 1.20 g. $^1$H NMR (CDCl$_3$) δ: 8.46 (1H, s), 7.81 (1H, d), 4.44-4.50 (2H, q), 3.80 (3H, s), 2.83 (3H, d), 1.42-1.46 (3H, t).
In a similar procedure, the following compounds were made from ethyl 2-difluoroiodomethyl-6-fluoro-7-methyl-[1,8]-naphthyridine-3-carboxylate and the appropriate alcohol:
Ethyl 6-fluoro-2-(ethoxydifluoromethyl)-7-methyl-[1,8]-naphthyridine-3-carboxylate $^1$H NMR (CDCl$_3$) δ: 8.42 (1H, s), 7.79 (1H, d), 4.42-4.48 (2H, q), 4.16-4.22 (2H, q), 2.82 (3H, d), 1.40-1.44 (3H, t), 1.34-1.38 (3H, t).
Ethyl 6-fluoro-2-(2-methoxyethoxydifluoromethyl)-7-methyl-[1,8]-naphthyridine-3-carboxylate, $^1$H NMR (CDCl$_3$) δ: 8.44 (1H, s), 7.79 (1H, d); 4.42-4.48 (2H, q); 4.24-4.28 (2H, m); 3.66-3.70 (2H, m); 3.38 (3H, s); 2.82 (3H, d); 1.40-1.44 (3H, t).
$^{19}$F NMR (CFCCl$_3$ as standard): −119.7 ppm & −71.7 ppm.
Ethyl 6-fluoro-7-methyl-2-[(tetrahydrofuran-3-yl-methoxy)-difluoromethyl-[1,8]-naphthyridine-3-carboxylate, yellow oil, $^1$H NMR (CDCl$_3$) δ: 8.46 (1H, s), 7.80 (1H, d), 4.48 (2H, q), 4.12 (2H, m), 4.04 (1H, m), 3.80 (3H, m), 2.86 (3H, d), 2.65 (1H, m), 2.05 (1H, m) 1.70 (1H, m), 1.43 (3H, t).
Ethyl 6-fluoro-7-methyl-2-(1-methylethoxydifluoromethyl)-7-methyl-[1,8]-naphthyridine-3-carboxylate, $^1$H NMR (CDCl$_3$) δ: 8.40 (1H, s), 7.79 (1H, d), 4.84-4.90 (1H, m), 4.42-4.48 (2H, q), 2.84 (3H, d), 1.40-1.46 (3H, t), 1.36-1.40 (6H, d).
$^{19}$F NMR (CFCCl$_3$ as standard): −120.0 ppm and −69.1 ppm Stage 3

In a similar procedure to Example 4, Stage 5, ethyl 6-fluoro-2-methoxydifluoromethyl-7-methyl-[1,8]-naphthyridine-3-carboxylate was hydrolysed to give 6-fluoro-2-methoxydifluoromethyl-7-methyl-[1,8]-naphthyridine-3-carboxylic acid, yellow solid, $^1$H NMR (CDCl$_3$+1 drop d$_6$-DMSO) δ: 8.52 (1H, s), 7.83 (1H, d), 3.78 (3H, s), 2.80 (3H, d).
In a similar procedure, the following carboxylic acids were made from their corresponding naphthyridine esters:
2-(Ethoxydifluoromethyl)-6-fluoro-7-methyl-[1,8]-naphthyridine-3-carboxylic acid, $^1$H NMR (CDCl$_3$+1 drop d$_6$-DMSO) δ: 8.50 (1H, s), 7.83 (1H, d), 4.16-4.22 (2H, q), 2.82 (3H, d), 1.36-1.40 (3H, t).

6-Fluoro-2-(2-methoxyethoxydifluoromethyl)-7-methyl-[1,8]-naphthyridine-3-carboxylic acid, $^1$H NMR (CDCl$_3$+drop d$_6$-DMSO) δ: 8.56 (1H, s), 7.78-7.80 (1H, d), 4.28-4.34 (2H, m), 3.72-3.76 (2H, m), 3.40 (3H, s), 2.84 (3H, d).
6-Fluoro-7-methyl-2-[(tetrahydrofuran-3-yl-methoxy)-difluoromethyl]-[1,8]-naphthyridine-3-carboxylic acid, $^1$H NMR (CDCl$_3$+1 drop d$_6$-DMSO) δ: 8.56 (1H, s), 7.81 (1H, d), 4.20-4.24 (1H, m), 3.96-4.02 (2H, m), 3.78-3.88 (2H, m), 2.84 (3H, d), 2.08-2.16 (1H, m), 1.72-1.82 (1H, m).
6-Fluoro-2-(1-methylethoxydifluoromethyl)-7-methyl-[1,8]-naphthyridine-3-carboxylic acid, $^1$H NMR (CDCl$_3$+5 drop d$_6$-DMSO) δ: 8.60 (1H, s), 7.82-7.84 (1H, d), 4.90-4.96 (1H, m), 2.84 (3H, d), 1.38-1.40 (6H, d).

Stage 4

In a similar procedure to Example 4, Stage 6, 6-fluoro-2-methoxydifluoromethyl-7-methyl-[1,8]-naphthyridine-3-carboxylic acid was reacted with cyclohexane-1,3-dione to give 2-[6-fluoro-2-(methoxydifluoromethyl)-7-methyl [1,8]-naphthyridine-3-carbonyl]-cyclohexane-1,3-dione, yellow solid, m.p. 143-146° C., $^1$H NMR (CDCl$_3$) δ: 16.6 (1H, s), 7.94 (1H, s), 7.83 (1H, d), 7.71 (1H, d), 3.68 (3H, s), 2.84-2.80 (5H, m), 2.38-2.42 (2H, t), 2.02-2.10 (2H, m).
In a similar procedure, the following compounds were made from cyclohexane-1,3-dione and the corresponding naphthyridine carboxylic acid:
2-[2-(Ethoxydifluoromethyl)-6-fluoro-7-methyl-[1,8]-naphthyridine-3-carbonyl]-cyclohexane-1,3-dione, yellow solid, m.p. 168-170° C., $^1$H NMR (CDCl$_3$) δ:16.7 (1H, s), 7.94 (1H, s), 7.70-7.72 (1H, d), 4.06-4.12 (2H, q), 2.78-2.84 (5H, m), 2.38-2.42 (2H, t), 2.02-1.24-1.28 (3H, t), 2.08 (2H, m).
2-[6-Fluoro-2-(2-methoxyethoxydifluoromethyl)-7-methyl-[1,8]-naphthyridine-3-carbonyl]-cyclohexane-1,3-dione, yellow solid, m.p. 156-158° C., $^1$H NMR (CDCl$_3$) δ: 7.94 (1H, s), 7.71 (1H, d), 7.71 (1H, d), 4.12-4.14 (2H, m), 3.56-3.58 (2H, m), 3.34 (3H, s), 2.78-2.84 (5H, m), 2.36-2.40 (2H, t), 2.02-2.08 (2H, m).
2-[6-Fluoro-7-methyl-2-[(tetrahydrofuran-3-yl-methoxy)-difluoromethyl-[1,8]-naphthyridine-3-carbonyl]-cyclohexane-1,3-dione, pale brown solid, Molecular ion: (MH)$^+$ 451, $^1$H NMR (CDCl$_3$) δ:16.8 (1H, s), 7.92 (1H, s), 7.70-7.72 (1H, d), 3.90-4.12 (2H, m), 3.70-3.86 (3H, m), 3.52-3.56 (1H, m), 2.80-2.86 (5H, m), 2.50-2.58 (1H, m), 2.39-2.43 (2H, t), 1.98-2.10 (3H, m), 1.58-1.66 (1H, m).
2-[6-Fluoro-2-(1-methylethoxydifluoromethyl)-7-methyl-[1,8]-naphthyridine-3-carbonyl]-cyclohexane-1,3-dione, yellow solid, Molecular ion: (MH)$^+$409, $^1$H NMR (CDCl$_3$) δ: 16.8 (1H, s), 7.90 (1H, s), 7.71 (1H, d), 4.76-4.82 (1H, m), 2.78-2.84 (5H, m), 2.38-2.42 (2H, t), 2.02-2.08 (2H, m), 1.25-1.29 (6H, d).
Similarly, (2-methoxy-1,1-difluoroethyl)-6-fluoro-7-methyl-[1,8]-naphthyridine-3-carboxylic acid was reacted with bicyclo[3.2.1]octane-2,4-dione to give 3-[6-fluoro-2-(2-methoxy-1,1-difluoroethyl)-7-methyl [1,8]-naphthyridine-3-carbonyl]-bicyclo[3.2.1]octane-2,4-dione, yellow solid, Molecular ion: (MH)$^+$421, m.p. 177-180° C., $^1$H NMR (CDCl$_3$) δ: 16.7 (1H, s), 7.98 (1H, s), 7.73 (1H, d), 4.20-4.45 (2H, broad in); 3.50 (3H, s), 3.14-3.18 (1H, broad triplet), 2.82-2.86 (4H, m), 2.18-2.26 (2H, m), 2.00-2.16 (2H, m), 1.70-1.76 (2H, m).

EXAMPLE 22

Preparation of 2-(6-fluoro-7-methyl-2-trifluoromethyl-[1,8]-naphthyridine-8-oxy-3-carbony)-cyclohexane-1,3-dione To a stirred solution of 2-(6-fluoro-7-methyl-2-trifluoromethyl-[1,8]-naphthyridine-3-carbony)-cyclohexane-1,3- dione (0.150 g) in dichloromethane (10 ml) containing urea hydrogenperoxide complex (0.166 g, 30% peroxide by weight) at ambient temperature was added trifluoroacetic anhydride (0.074 ml). The reaction mixture began to reflux on addition of the anhydride and was allowed to stir for a further 3 hours. The mixture was washed with water (50 ml) then brine (50 ml) and the organic phase separated and dried over magnesium sulfate, filtered and evaporated under reduced pressure to give a solid. The solid was purified by chromatography (silica; toluene/dioxane/ethanol/triethylamine/water, 20:8:4:4:1 by volume) to give the required product as the triethylamine salt. The salt was dissolved in ethyl acetate (20 ml), washed with aqueous 2M hydrochloric acid (2×5 ml), water (1×5 ml) and dried over magnesium sulfate then evaporated under reduced pressure to give the required product, 0.027 g. $^1$H NMR (CDCl$_3$) δ: 16.41 (1H, s), 8.08 (1H, s), 7.37 (1H, d), 2.85 (2H, t), 2.73 (3H, d), 2.41 (2H, t), 2.07 (2H, quintet).

Preparation of methyl 4,4-difluoro-5-methoxy-3-oxopentanoate

To a stirred solution of dry N,N-diisopropylamine (1.31 g) in dry tetrahydrofuran (10 ml) under an atmosphere of nitrogen was added a solution of n-butyl lithium (5.2 ml, 2.5M in hexane) dropwise over 5 minutes at −40° C. On complete addition, the reaction temperature was allowed to slowly rise to 0° C. then the mixture was cooled to −78° C. and a solution of dry ethyl acetate (1.14 g) in dry tetrahydrofuran (2 ml) was added dropwise over 2 minutes. After 1 hr, a solution of methyl 2,2-difluoro-3-methoxypropionate (1.0 g) in dry tetrahydrofuran (2 ml) was added dropwise over 5 minutes. The reaction was stirred at −78° C. for 3 hours then allowed to attain ambient temperature, quenched with saturated aqueous ammonium chloride and extracted with ethyl acetate (three times). The extracts were combined, washed with aqueous 1M hydrochloric acid then brine and dried over magnesium sulfate, filtered and evaporated under reduced pressure to give a colourless oil, 1.39 g, containing a mixture of methyl 4,4-difluoro-5-methoxy-3-oxopentanoate and some ethyl acetoacetate. The product was used without further purification.
$^1$H NMR showed the required product to exist as a mixture of enol and keto forms: $^1$H NMR (CDCl$_3$) δ: enol form 12.0 (1H, s), 5.58 (1H, s) and keto form 3.72 (2H, s).
In a similar procedure, ethyl difluoroiodoacetate was reacted with ethyl acetate to give ethyl 4,4-difluoro-4-iodo-acetoacetate, $^1$H NMR (CDCl$_3$) δ: enol form 12.0 (1H, s), 5.50 (1H, s) and keto form 3.82 (2H, s).

Preparation of Intermediate Acids

Preparation of 2-difluoromethyl-[1,8]-naphthyridine-3-carboxylic acid

A mixture of 2-amino-pyridine-3-carboxaldehyde (2.0 g), ethyl difluoroacetoacetate (2.7 g) and piperidine (1.58 ml) in ethanol (5 ml) were heated in a sealed tube in a microwave oven with stirring for 10 minutes at 130° C. The reaction mixture was cooled, diluted with a mixture of ethanol and water (3:1 by volume, 50 ml) then lithium hydroxide hydrate (2.0 g) was added. The mixture was stirred for 1 hour at ambient temperature, evaporated under reduced pressure to remove most of the ethanol then acidified to pH 1 with aqueous hydrochloric acid. The required product was filtered from solution and sucked to dryness to give the required product as a colourless solid, 2.5 g.
$^1$H NMR (CDCl$_3$) δ: 9.10 (1H, dd), 8.77 (1H, s), 8.19 (1H, dd), 7.43 (1H, dd), 7.38 (1H, t), 7.31 (1H, s).
In a similar procedure to the preparation of 2-difluoromethyl-[1,8]-naphthyridine-3-carboxylic acid, the following naphthyridine-3-carboxylic acids were made from 2-amino-pyridine-3-carboxaldehyde and the corresponding ketoesters:
From ethyl acetoacetate, 2-methyl-[1,8]-naphthyridine-3-carboxylic acid, pale yellow solid, $^1$H NMR (CDCl$_3$) δ: 9.10 (1H, dd), 8.77 (1H, s), 8.19 (1H, dd), 7.43 (1H, dd), 7.38 (1H, t), 7.31 (1H, s).
From ethyl 3-oxo-4,4,5,5,5-pentafluoropentanoate, 2-pentafluoroethyl-[1,8]-naphthyridine-3-carboxylic acid, colourless solid. $^1$H NMR (CDCl$_3$) δ: 9.32 (1H, m), 9.13 (1H, s), 8.72 (1H, m), 7.89 (1H, m).

Preparation of 7-isopropoxy-2-trifluoromethyl-[1,8]-naphthyridine-3-carboxylic acid Sodium hydride (0.16 g, 60% dispersion in mineral oil) was added to propan-2-ol (5 ml) and stirred at ambient temperature for 10 minutes to generate a solution of sodium propan-2-oxide. To this was added ethyl 7-chloro-2-trifluoromethyl-[1,8]-naphthyridine-3-carboxylate (0.612 g) then the mixture was sealed in a tube and heated with stirring in a microwave oven at 130° C. for 10 minutes. The mixture was evaporated under reduced pressure, acidified to pH 1 with aqueous 2M hydrochloric acid and extracted with ethyl acetate (2×15 ml). The extracts were combined, washed with brine (10 ml), dried over magnesium sulfate, filtered and evaporated under reduced pressure to give the required product as a yellow solid, 0.52 g. $^1$H NMR (d$_6$-DMSO) δ: 9.33 (1H, s), 8.89 (1H, d), 7.63 (1H, d), 6.05 (1H, septet), 1.83 (3H, d).
In a similar procedure, the following 7-alkoxynaphthyridine-3-carboxylic acids were prepared from ethyl 7-chloro-2-trifluoromethyl-[1,8]-naphthyridine-3-carboxylate and the corresponding alkoxide/alcohol:
7-(2-Methoxyethoxy)-2-trifluoromethyl-[1,8]-naphthyridine-3-carboxylic acid using 2-methoxyethanol. $^1$H NMR (d$_6$-DMSO) δ: 14.0 (1H, bs), 9.00 (1H, s), 8.55 (1H, d), 7.40 (1H, d), 4.65 (2H, m), 3.75 (2H, m), 3.35 (3H, s).
7-Allyloxy-2-trifluoromethyl-[1,8]-naphthyridine-3-carboxylic acid using allyl alcohol. $^1$H NMR (CDCl$_3$) δ: 8.43 (1H, s), 7.94 (1H, d), 6.90 (1H, d), 5.87-5.78 (1H, m), 5.12-5.16 (1H, m), 5.00 (1H, m), 4.80 (2H, m).
7-(2,2,2-Trifluoroethoxy)-2-trifluoromethyl-[1,8]-naphthyridine-3-carboxylic acid using 2,2,2-trifluoroethanol. $^1$H NMR (d$_6$-DMSO) δ: 9.10 (1H, s), 8.70 (1H, d), 7.58 (1H, d), 5.28 (2H, q).

Preparation of 6-chloro-2-trifluoromethyl-[1,8]-naphthyridine-3-carboxylic acid

Stage 1

Preparation of 2-amino-5-chloropyridine-3-carboxaldehyde

A mixture of 2-amino-3-carboxaldehyde (10.00 g) and N-chlorosuccinimide (11.54 g) in dichloromethane (300 ml) was stirred and heated to reflux for 1.5 hours then cooled to 0° C. in an ice bath. The solid that precipitated was filtered from solution, washed with acetonitrile and sucked to dryness to give the required product as a yellow solid, 10.05 g. $^1$H NMR (CDCl$_3$) δ:9.83 (1H, s), 8.22 (1H, d), 7.78 (1H, d).

Stage 2

Preparation of ethyl 6-chloro-2-trifluoromethyl-[1,8]-naphthyridine-3-carboxylate A mixture of 2-amino-5-chloropyridine-3-carboxaldehyde (2.34 g), ethyl 4,4,4-trifluoroacetoacetate (2.19 ml) in ethanol (3 ml) containing piperidine (1.5 ml) was sealed in tube and heated with stirring in a microwave oven to 130° C. for 10 minutes. The yellow solid that had formed was filtered from solution, washed with ethanol and sucked to dryness to give the required product, 2.70 g. $^1$H NMR (CDCl$_3$) δ:9.21 (1H, d), 8.68 (1H, s), 8.33 (1H, d), 4.50 (2H, q), 1.45 (3H, t).

Stage 3

To a stirred suspension of ethyl 6-chloro-2-trifluoromethyl-[1,8]-naphthyridine-3-carboxylate (2.50 g) in ethanol (60 ml) and water (30 ml) was added lithium hydroxide monohydrate (0.800 g) at ambient temperature. The mixture was stirred for 2 hours, acidified to pH 1 with aqueous 2M hydrochloric acid and precipitate was filtered from solution and sucked to dryness to give 6-chloro-2-trifluoromethyl-[1,8]-naphthyridine-3-carboxylic acid as a pale yellow solid, 1.90 g. $^1$H NMR (d$_6$-DMSO) δ:14.27 (1H, s), 9.33 (1H, d), 9.10 (1H, s), 8.92 (1H, d).

Preparation of 7-chloro-2-trifluoromethyl-[1,8]-naphthyridine-3-carboxylic acid

To a stirred suspension of ethyl 7-chloro-2-trifluoromethyl-[1,8]-naphthyridine-3-carboxylate (0.57 g) in propan-2-ol (15 ml) containing water (7.5 ml) was added lithium hydroxide monohydrate (0.16 g). The mixture was heated to 50° C. for 5 minutes to produce a solution that was stirred for a further 1 hour allowing the mixture to gradually cool to ambient temperature. The mixture was acidified to pH 1 with aqueous 2M hydrochloric acid and the required product that precipitated as a colourless solid, 0.45 g, was filtered from solution and sucked to dryness. $^1$H NMR (d$_6$-DMSO) δ: 9.21 (1H, s), 8.79 (1H, d), 8.00 (1H, d).

Preparation of 7-(morpholin-4-yl)-2-trifluoromethyl-[1,8]-naphthyridine-3-carboxylic acid Stage 1

Preparation of ethyl 7-(morpholin-4-yl)-2-trifluoromethyl-[1,8]-naphthyridine-3-carboxylate A suspension of ethyl 7-chloro-2-trifluoromethyl-[1,8]-naphthyridine-3-carboxylate (0.57 g) in ethanol (2 ml) containing morpholine (0.711 ml) was sealed in a tube and heated with stirring in a microwave oven to 140° C. for 20 minutes then allowed to cool to ambient temperature. The mixture was evaporated under reduced pressure and the residue purified by chromatography (silica, hexane/ethyl acetate) to give the required product, 0.45 g. $^1$H NMR (CDCl$_3$) δ: 8.47 (1H, s), 7.89 (1H, d), 7.14 (1H, d), 4.44 (2H, q), 3.92 (4H, m), 3.84 (4H, m), 1.42 (3H, t).
In a similar procedure, ethyl 7-chloro-6-fluoro-2-trifluoromethyl-[1,8]-naphthyridine-3-carboxylate was heated in N,N-dimethylformamide with 2,2,2-trifluoroethylamine to give ethyl 6-fluoro-7-(2,2,2-trifluoroethylamino)-2-trifluoromethyl-[1,8]-naphthyridine-3-carboxylate. $^1$H NMR (CDCl$_3$) δ: 8.51 (1H, s), 7.69 (1H, d), 5.75 (1H, broad s), 4.61-4.52 (2H, m), 4.47 (2H, q), 1.44 (3H, t).

The following compounds were made in a similar procedure:
From 3,3-difluoroazetidine, ethyl 6-fluoro-7-(3,3-difluoroazetidin-1-yl)-2-trifluoromethyl-[1,8]-naphthyridine-3-carboxylate, yellow solid. $^1$H NMR (CDCl$_3$) δ: 8.48 (1H, s), 6.62 (1H, d), 4.82 (4H, td), 4.45 (2H, q), 1.42 (3H, t). Molecular ion: (MH)$^+$380.

From 3-methoxyazetidine, ethyl 6-fluoro-7-(3-methoxyazetidin-1-yl)-2-trifluoromethyl-[1,8]-naphthyridine-3-carboxylate. $^1$H NMR (CDCl$_3$) δ: 8.40 (1H, s), 7.48 (1H, d), 4.68 (2H, m), 4.42 (5H, m), 3.37 (3H, s), 1.40 (3H, t).

The following compounds were made in a similar procedure by stirring ethyl 7-chloro-6-fluoro2-trifluoromethyl-[1,8]-naphthyridine-3-carboxylate in N,N-dimethylformamide with the corresponding amine (or the amine hydrochloride and an equivalent of triethylamine) at ambient temperature for 20 minutes.

From cyclopropylamine hydrochloride, ethyl 7-(cyclopropylamino)-6-fluoro-2-trifluoromethyl-[1,8]-naphthyridine-3-carboxylate. $^1$H NMR (CDCl$_3$) δ: 8.47 (1H, s), 7.52 (1H, d), 5.70 (1H, bs), 4.42 (2H, q), 3.26 (1H, m), 1.42 (3H, t), 1.02 (2H, m), 0.68 (2H, m).

From methylamine hydrochloride, ethyl 6-fluoro-7-methylamino-2-trifluoromethyl-[1,8]-naphthyridine-3-carboxylate, yellow solid. $^1$H NMR (CDCl$_3$) δ: 8.42 (1H, s), 7.51 (1H, s), 5.64 (1H, bs), 4.45 (2H, q), 3.31 (3H, d), 1.42 (3H, t). Molecular ion: (MH)$^+$318.

From ethylamine hydrochloride, ethyl 7-ethylamino-6-fluoro-2-trifluoromethyl-[1,8]-naphthyridine-3-carboxylate. $^1$H NMR (CDCl$_3$) δ: 8.41 (1H, s), 7.52 (1H, d), 5.53 (1H, broad s), 4.44 (2H, q), 3.86-3.79 (2H, m), 1.42 (3H, t), 1.36 (3H, t).

From dimethylamine hydrochloride, ethyl 7-(dimethylamino)-6-fluoro-2-trifluoromethyl-[1,8]-naphthyridine-3-carboxylate. $^1$H NMR (CDCl$_3$) δ: 8.40 (1H, s), 7.53 (1H, d), 4.43 (2H, q), 3.43 (6H, d), 1.42 (3H, t).

From diethylamine hydrochloride, ethyl 7-(diethylamino)-6-fluoro-2-trifluoromethyl-[1,8]-naphthyridine-3-carboxylate. $^1$H NMR (CDCl$_3$) δ: 8.35 (1H, s), 7.50 (1H, d), 4.45 (2H, q), 3.80 (4H, q), 1.40 (3H, t), 1.30 (6H, t). Molecular ion: (MH)$^+$360

From N-methylethylamine, ethyl 6-fluoro-7-(N-methylethylamino)-2-trifluoromethyl-[1,8]-naphthyridine-3-carboxylate. $^1$H NMR (CDCl$_3$) δ: 8.39 (1H, s), 7.52 (1H, d), 4.43 (2H, q), 3.82 (2H, quartet of doublets), 3.39 (3H, d), 1.42 (3H, t), 1.32 (3H, t).

From 2-methoxyethylamine, ethyl 6-fluoro-7-(2-methoxyethylamino)-2-trifluoromethyl-[1,8]-naphthyridine-3-carboxylate. $^1$H NMR (CDCl$_3$) δ: 8.43 (1H, s), 7.54 (1H, d), 6.02 (1H, broad s), 4.44 (2H, q), 3.99 (2H, q), 3.66 (2H, t), 3.42 (3H, s), 1.42 (3H, t).

From (2-methoxyethyl)methylamine, ethyl 6-fluoro-7-((2-methoxyethyl)methylamino)-2-trifluoromethyl-[1,8]-naphthyridine-3-carboxylate. $^1$H NMR (CDCl$_3$) δ: 8.44 (1H, s), 7.59 (1H, d), 4.48 (2H, q), 4.04 (2H, t), 3.74 (2H, t), 3.51 (3H, d), 3.39 (3H, d), 1.46 (3H, t).

From morpholine, ethyl 6-fluoro-7-(morpholin-4-yl)-2-trifluoromethyl-[1,8]-naphthyridine-3-carboxylate. $^1$H NMR (CDCl$_3$) δ: 8.47 (1H, s), 7.89 (1H, d), 4.45 (2H, q), 3.99 (2H, t), 3.87 (2H, t), 1.42 (3H, t).

From propargylamine, ethyl 6-fluoro-7-propargylamino)-2-trifluoromethyl-[1,8]-naphthyridine-3-carboxylate. Molecular ion: (MH)$^+$314.

Stage 2

The product from Stage 1 (0.42 g) was suspended in ethanol (15 ml) containing water (7.5 ml) and lithium hydroxide monohydrate (0.105 g) was added. The mixture was heated to 50° C. for 5 minutes then stirred at ambient temperature for 1 hour. The mixture was acidified to pH 6 with aqueous 2M hydrochloric acid and extracted with ethyl acetate (3×20 ml). The extracts were combined, washed with brine (15 ml), dried over magnesium sulfate, filtered and evaporated under reduced pressure to give the required product as a colourless solid, 0.35 g. $^1$H NMR ($d_6$-DMSO) δ: 8.66 (1H, s), 8.22 (1H, d), 7.48 (1H, d), 3.78 (4H, m), 3.67 (4H, m).

Preparation of 7-phenoxy-2-trifluoromethyl-[1,8]-naphthyridine-3-carboxylic acid

Stage 1

Preparation of ethyl 7-phenoxy-2-trifluoromethyl-[1,8]-naphthyridine-3-carboxylate A mixture of ethyl 7-chloro-2-trifluoromethyl-[1,8]-naphthyridine-3-carboxylate (0.608 g) in acetonitrile (4 ml) containing phenol (0.184 g) and cesium carbonate (0.975 g) was sealed in a tube and heated with stirring in a microwave oven to 130° C. for 15 minutes then allowed to cool to ambient temperature. The mixture was diluted with ethyl acetate (20 ml) and washed with water (2×10 ml), dried and evaporated under reduced pressure and the residue purified by chromatography (silica, hexane/ethyl acetate) to give the required product, 0.55 g. $^1$H NMR (CDCl$_3$) δ: 8.66 (1H, s), 8.27 (1H, d), 7.46 (2H, t), 7.40 (1H, d), 7.31-7.27 (3H, m), 4.46 (2H, q), 1.43 (3H, t).

Stage 2

The product from Stage 1 (0.515 g) was suspended in ethanol (7.5 ml) containing water (2.5 ml) and lithium hydroxide (0.12 g) was added. The mixture was stirred at ambient temperature for 3 hour, acidified to pH 1 with aqueous 2M hydrochloric acid and extracted with ethyl acetate. The extracts were combined, washed with brine, dried over magnesium sulfate, filtered and evaporated under reduced pressure to give the required product, 0.42 g. $^1$H NMR ($d_6$-DMSO) δ: 8.60 (1H, s), 8.20 (1H, d), 7.40 (1H, d), 7.30-7.00 (5H, m).

Preparation of 7-(6-fluoropyrid-3-yl)-2-trifluoromethyl-[1,8]-naphthyridine-3-carboxylic acid

Stage 1

Preparation of ethyl 7-(6-fluoropyrid-3-yl)-2-trifluoromethyl-[1,8]-naphthyridine-3-carboxylate A mixture of ethyl 7-chloro-2-trifluoromethyl-[1,8]-naphthyridine-3-carboxylate (0.400 g) in toluene (6 ml) containing 6-fluoropyridyl-3-boronic acid (0.282 g), potassium phosphate (0.422 g), palladium acetate (0.015 g) and dicyclohexyl-(2',6'-dimethoxybiphenyl-2-yl)phosphane (0.054 g) were stirred and heated to reflux for 16 hours then cooled to ambient temperature. The mixture was evaporated under reduced pressure and the residue purified by chromatography (silica, hexane/ethyl acetate) to give the required product as a colourless solid, 0.33 g. $^1$H NMR (CDCl$_3$) δ: 9.07 (1H, d), 8.90 (1H, d), 8.79 (1H, s), 8.48 (1H, d), 8.18 (1H, d), 7.15 (1H, dd), 4.50 (2H, q), 1.46 (3H, t).

Stage 2

The product from Stage 1 (0.300 g) was suspended in propan-2-ol (15 ml) containing water (7.5 ml) and lithium hydroxide monohydrate (0.160 g) was added. The mixture was heated to 50° C. for 2 hours then cooled to ambient temperature. The mixture was acidified to pH 6 with aqueous 2M hydrochloric acid and extracted with ethyl acetate (3×20 ml). The extracts were combined, washed with brine (15 ml), dried over magnesium sulfate, filtered and evaporated under reduced pressure to give the required product as a pale yellow solid, 0.28 g. $^1$H NMR ($d_6$-DMSO) δ: 9.23 (1H, d), 9.17 (1H, s), 8.95 (1H, d), 8.86 (1H, d), 8.60 (1H, d).

Preparation of 7-methyl-2-trifluoromethyl-[1,8]-naphthyridine-3-carboxylic acid

Stage 1

Preparation of ethyl 7-methyl-2-trifluoromethyl-[1,8]-naphthyridine-3-carboxylate To a solution of ethyl 7-chloro-2-trifluoromethyl-[1,8]-naphthyridine-3-carboxylate (0.304 g) in toluene (6 ml) containing water (0.25 ml) was added palladium (II) acetate (0.012 g), potassium phosphate (0.425 g), and methyl boronic acid (0.090 g) and dicyclohexyl-(2',6'-dimethoxybiphenyl-2-yl)phosphane (0.041 g). The mixture was stirred and heated to reflux for 16 hours then cooled to ambient temperature. The mixture was diluted with ethyl acetate (20 ml), washed with water (15 ml), brine (10 ml) then dried over magnesium sulphate. The solution was filtered, evaporated under reduced pressure and the residue was purified by chromatography (silica, ethyl acetate/hexane) to give the required product as a colourless solid, 0.090 g. $^1$H NMR (CDCl$_3$) δ: 8.71 (1H, s), 8.23 (1H, d), 7.59 (1H, s), 4.49 (2H, q), 2.89 (3H, s), 1.45 (3H, t).

Stage 2

To a suspension of ethyl 7-methyl-2-trifluoromethyl-[1,8]-naphthyridine-3-carboxylate (0.300 g) in ethanol (15 ml) containing water (7.5 ml) was added lithium hydroxide monohydrate (0.126 g) and the mixture stirred at ambient temperature for 3 hours. The mixture was then acidified to pH 6 with aqueous 2M hydrochloric acid and extracted with dichloromethane (2×15 ml). The extracts were combined, washed with brine (10 ml), dried over magnesium sulfate, filtered and evaporated under reduced pressure to give the required product a pale yellow solid, 0.27 g. $^1$H NMR (CDCl$_3$) δ: 8.71 (1H, d), 8.19 (1H, d), 7.51 (1H, d), 2.80 (3H, s).

Preparation of 6-methyl-2-trifluoromethyl-[1,8]-naphthyridine-3-carboxylic acid

Stage 1

In a similar procedure to Example 15, Stage 1, ethyl 6-bromo-2-trifluoromethyl-[1,8]-naphthyridine-3-carboxylate was reacted with methyl boronic acid to give ethyl 6-methyl-2-trifluoromethyl-[1,8]-naphthyridine-3-carboxylate as a pale pink solid. $^1$H NMR (CDCl$_3$) δ: 9.14 (1H, d), 8.85 (1H, s), 8.08 (1H, d), 4.48 (2H, q), 2.62 (3H, s), 1.44 (3H, t).

Stage 2

In a similar procedure to Example 1, Stage 2, ethyl 6-methyl-2-trifluoromethyl-[1,8]-naphthyridine-3-carboxylate was hydrolysed with lithium hydroxide to give 6-methyl-2-trifluoromethyl-[1,8]-naphthyridine-3-carboxylic acid as a pale yellow solid. $^1$H NMR (d$_6$-DMSO) δ: 9.19 (1H, d), 9.03 (1H, s), 8.47 (1H, d), 2.80 (3H, s).

Preparation of 2-(2,7-bis(trifluoromethyl)[1,8]-naphthyridine-3-carboxylic acid

Stage 1

Preparation of methyl 2-amino-6-trifluoromethylpyridine-3-carboxylate

A mixture of methyl 2-bromo-6-trifluoromethylpyridine-3-carboxylate (2.00 g), cesium carbonate (3.40 g), palladium acetate (0.080 g), benzophenone imine (1.4 ml) and 4,5-bis-diphenylphosphoranyl-9,9-dimethyl-9H-xanthene (0.31 g) in dioxane (5 ml) was heated with stirring to 150° C. in a sealed vessel in a microwave oven for 30 minutes then cooled to ambient temperature. The reaction mixture was diluted with dichloromethane (30 ml), washed with water and evaporated under reduced pressure. The residue was dissolved in ethyl acetate (20 ml), washed with aqueous 2M hydrochloric acid (2×20 ml) then brine and dried over magnesium sulphate, filtered and evaporated under reduced pressure. The residue was purified by chromatography (silica, hexane/ethyl acetate) to give the required product as a colourless solid, 0.850 g. $^1$H NMR (CDCl$_3$) δ: 8.28 (1H, d), 6.98 (1H, d), 3.92 (3H, s).

Stage 2

Preparation of 2-amino-3-hydroxymethyl-6-trifluoromethylpyridine

To a stirred solution of methyl 2-amino-6-trifluoromethylpyridine-3-carboxylate (0.220 g) in dry tetrahydrofuran (10 ml) at 0° C. was added a solution of lithium aluminium hydride in tetrahydrofuran (0.500 ml, 2M). The mixture was stirred for 2 hours, diluted with ethyl acetate (20 ml) then water (0.50 ml) was added followed by aqueous sodium hydroxide (0.200 ml, 2M). The mixture was dried by adding magnesium sulphate, filtered, the insoluble material washed with ethyl acetate and the combined filtrate evaporated under reduced pressure to give the required product as a colourless solid, 0.190 g. $^1$H NMR (CDCl$_3$) δ: 7.44 (1H, d), 6.96 (1H, d), 5.40 (2H, s), 4.62 (2H, s), 4.03 (1H, s).

Stage 3

Preparation of 2-amino-6-trifluoromethylpyridine-3-carboxaldehyde

To a solution of 2-amino-3-hydroxymethyl-6-trifluoromethylpyridine (0.190 g) in chloroform (10 ml) was added manganese dioxide (0.348 g) and the mixture stirred at ambient temperature for 3 hours. The insoluble material was filtered from solution, washed with ethyl acetate and the combined filtrate evaporated under reduced pressure to give the required product as a colourless solid, 0.18 g. $^1$H NMR (CDCl$_3$) δ: 9.95 (1H, s), 8.00 (1H, d), 7.10 (1H, d).

Stage 4

Preparation of ethyl 2,7-bis(trifluoromethyl)-[1,8]-naphthyridine-3-carboxylate

A mixture of 2-amino-6-trifluoromethylpyridine-3-carboxaldehyde (0.170 g), ethyl 4,4,4-trifluoroacetoacetate (0.131 ml) in ethanol (3 ml) containing piperidine (0.089 ml) was sealed in a tube and heated with stirring to 130° C. for 20 minutes then cooled to ambient temperature and evaporated under reduced pressure. The residue was purified by chromatography (silica, hexane/ethyl acetate) to give ethyl 2,7-bis(trifluoromethyl)-[1,8]-naphthyridine-3-carboxylate as a colourless solid, (0.065 g). $^1$H NMR (CDCl$_3$) δ: 8.85 (1H, s), 8.62 (1H, d), 8.05 (1H, d), 4.51 (2H, q), 1.46 (3H, t).

Stage 5

To a solution of ethyl 2,7-bis(trifluoromethyl)-[1,8]-naphthyridine-3-carboxylate (1.50 g) in ethanol (50 ml) containing water (25 ml) was added lithium hydroxide monohydrate (0.56 g) at ambient temperature and the mixture stirred for 3 hours. The solution was acidified with aqueous 2M hydrochloric acid, the precipitate filtered from solution and sucked to dryness to give the required product as a colourless solid, 1.15 g. $^1$H NMR (d$_6$-DMSO) δ: 9.33 (1H, s), 9.09 (1H, d), 8.38 (1H, d).

Preparation of 2-methyl-7-trifluoromethyl-[1,8]-naphthyridine-3-carboxylic acid

Stage 1

Preparation of methyl 2-methyl-7-trifluoromethyl-[1,8]-naphthyridine-3-carboxylate 2-amino-6-trifluoromethylpyridine-3-carboxaldehyde was reacted with methyl acetoacetate to give methyl 2-methyl-7-trifluoromethyl-[1,8]-naphthyridine-3-carboxylate as a colourless solid. $^1$H NMR (CDCl$_3$) δ: 8.85 (1H, s), 8.48 (1H, d), 7.87 (1H, d), 4.03 (3H, s), 3.10 (3H, s).

In a similar process to Stage 1, 2-amino-6-trifluoromethylpyridine-3-carboxaldehyde was reacted with the following ketoesters to give the corresponding [1,8]-naphthyridine esters:

From methyl 4-methoxyacetoacetate, methyl 2-(methoxymethyl)-7-trifluoromethyl-[1,8]-naphthyridine-3-carboxylate as a colourless oil. $^1$H NMR (CDCl$_3$) δ: 8.73 (1H, s), 8.50 (1H, d), 7.90 (1H, d), 5.10 (2H, s), 4.05 (3H, s), 3.45 (3H, s).

From ethyl-4-oxopentanoate, ethyl 2-ethyl-7-trifluoromethyl-[1,8]-naphthyridine-3-carboxylate as a yellow solid. $^1$H NMR (CDCl$_3$) δ: 8.78 (1H, s), 8.48 (1H, d), 7.86 (1H, d), 4.49 (2H, q), 3.43 (2H, q), 1.48 (3H, t), 1.45 (3H, t).

From methyl 4-(methanesulfonyl-N-methylamino)-3-oxobutyrate, methyl 2-(methanesulfonyl-N-methylaminomethyl)-7-trifluoromethyl-[1,8]-naphthyridine-3-carboxylate, $^1$H NMR (CDCl$_3$) δ: 8.75 (1H, s), 8.50 (1H, d), 7.90 (1H, d), 5.10 (2H, s), 4.05 (3H, s), 3.45 (3H, s).

Stage 2

In a similar procedure to Example 1, Stage 2, methyl 2-methyl-7-trifluoromethyl-[1,8]-naphthyridine-3-carboxylate was hydrolysed with lithium hydroxide to give 2-methyl-7-trifluoromethyl-[1,8]-naphthyridine-3-carboxylic acid as a colourless solid. $^1$H NMR (d$_6$-DMSO) δ:13.74 (1H, bs), 9.11 (1H, s), 8.94 (1H, d), 8.13 (1H, d), 2.96 (3H, s).

The following compounds were prepared in a similar procedure from their corresponding esters:

2-Ethyl-7-trifluoromethyl-[1,8]-naphthyridine-3-carboxylic acid, colourless solid. $^1$H NMR (d$_6$-DMSO) δ: 8.98 (1H, s), 8.84 (1H, d), 8.13 (1H, d), 3.24 (2H, q), 1.24 (3H, t).

2-Ethyl-6-fluoro-7-trifluoromethyl-[1,8]-naphthyridine-3-carboxylic acid, yellow solid. $^1$H NMR (d$_6$-DMSO) δ: 8.99 (1H, s), 8.42 (1H, d), 3.04 (2H, q), 1.31 (3H, t).

7-Methoxymethyl-2-trifluoromethyl-[1,8]-naphthyridine-3-carboxylic acid, yellow solid. Molecular ion: (MH)$^+$288

2-Chlorodifluoromethyl-7-methyl-[1,8]-naphthyridine-3-carboxylic acid, colourless solid, $^1$H NMR (d$_6$-DMSO) 8.66 (1H, s), 8.19-8.21 (1H, d), 7.52-7.54 (1H, d), 2.88 (3H, s).

2-(Methanesulfonyl-N-methylaminomethyl)-7-trifluoromethyl-[1,8]-naphthyridine-3-carboxylic acid, $^1$H NMR (d$_6$-DMSO) δ: 9.00 (1H, s), 8.90 (1H, d), 8.10 (1H, d), 4.90 (2H, s), 3.30 (3H, s).

2-Difluoromethyl-7-methyl-[1,8]-naphthyridine-3-carboxylic acid, colourless solid, $^1$H NMR (d$_6$-DMSO) 8.66 (1H, s), 8.19-8.21 (1H, d), 7.52-7.54 (1H, d), 2.88 (3H, s).

2-Difluoromethyl-6-fluoro-7-methyl-[1,8]-naphthyridine-3-carboxylic acid, yellow solid, $^1$H NMR (d$_6$-DMSO) δ: 9.05 (1H, s), 8.42 (1H, d), 7.60 (1H, t), 2.68 (3H, t).

2-Pentafluoroethyl-6-fluoro-7-methyl-[1,8]-naphthyridine-3-carboxylic acid, yellow solid, $^1$H NMR (d$_6$-DMSO) δ: 8.94 (1H, s), 8.35 (1H, d), 2.30 (3H, d).

2-Methoxymethyl-6-fluoro-7-methyl-[1,8]-naphthyridine-3-carboxylic acid, yellow solid, $^1$H NMR (d$_6$-DMSO) δ: 8.76 (1H, s), 8.30 (1H, d), 4.86 (2H, s), 3.22 (3H, s), 2.64 (3H, d).

7-(3,3-Difluoroazetidin-1-yl)-6-fluoro-2-trifluoromethyl-[1,8]-naphthyridine-3-carboxylic acid, yellow solid. $^1$H NMR (CDCl$_3$) δ: 8.80 (1H, s), 8.22 (1H, d), 4.84 (4H, t).

6-Fluoro-7-(3-methoxyazetidin-1-yl)-2-trifluoromethyl-[1,8]-naphthyridine-3-carboxylic acid, yellow solid, $^1$H NMR (d$_6$-DMSO) δ: 8.65 (1H, s), 8.05 (1H, d), 4.50 (2H, bs), 4.34 (1H, m), 4.15 (2H, bs), 3.24 (3H, s). Molecular ion: (MH)$^+$346.

7-(3,3-Difluoroazetidin-1-yl)-6-fluoro-2-trifluoromethyl-[1,8]-naphthyridine-3-carboxylic acid, $^1$H NMR (CDCl$_3$) δ: 8.47 (1H, s), 7.89 (1H, d), 7.14 (1H, d), 6-Fluoro-7-(3-methoxyazetidin-1-yl)-2-trifluoromethyl-[1,8]-naphthyridine-3-carboxylic acid, $^1$H NMR (CDCl$_3$) δ: 8.47 (1H, s), 7.89 (1H, d), 7.14 (1H, d), 7-(Cyclopropylamino)-6-fluoro-2-trifluoromethyl-[1,8]-naphthyridine-3-carboxylic acid, yellow solid, $^1$H NMR (CDCl$_3$) δ: 8.70 (1H, s), 8.35 (1H, d), 8.06 (1H, d), 3.10-3.06 (1H, m), 0.86-0.82 (2H, m), 0.71-0.67 (2H, m).

6-Fluoro-7-methylamino-2-trifluoromethyl-[1,8]-naphthyridine-3-carboxylic acid, Molecular ion: (MH)$^+$290.

7-Ethylamino-6-fluoro-2-trifluoromethyl-[1,8]-naphthyridine-3-carboxylic acid, yellow solid, $^1$H NMR (CDCl$_3$) δ: 8.58 (1H, s), 8.16 (1H, t), 7.97 (1H, d), 3.51 (2H, quintet), 1.17 (3H, t).

7-Dimethylamino-6-fluoro-2-trifluoromethyl-[1,8]-naphthyridine-3-carboxylic acid, yellow solid, $^1$H NMR (CDCl$_3$) δ: 8.63 (1H, s), 7.96 (1H, d), 3.26 (6H, s).

7-Diethylamino-6-fluoro-2-trifluoromethyl-[1,8]-naphthyridine-3-carboxylic acid, yellow solid, $^1$H NMR (CDCl$_3$) δ: 8.62 (1H, s), 8.07 (1H, d), 3.65 (4H, q), 1.19 (6H, t).

6-Fluoro-7-(N-methylethylamino)-2-trifluoromethyl-[1,8]-naphthyridine-3-carboxylic acid, yellow solid, $^1$H NMR (CDCl$_3$) δ: 8.62 (1H, s), 8.07 (1H, d), 3.68 (2H, quartet of doublets), 3.22 (3H, d), 1.18 (3H, t).

6-Fluoro-7-methoxyethylamino-2-trifluoromethyl-[1,8]-naphthyridine-3-carboxylic acid, yellow solid, $^1$H NMR (CDCl$_3$) δ: 8.62 (1H, s), 8.19 (1H, t), 8.01 (1H, d), 3.65 (2H, q), 3.53 (2H, t), 3.23 (3H, s).

6-Fluoro-7-((2-methoxyethyl)methylamino)-2-trifluoromethyl-[1,8]-naphthyridine-3-carboxylic acid, $^1$H NMR (d$_6$DMSO) δ: 9.18 (1H, s), 8.6 (1H, d), 4.20 (2H, t), 4.08 (2H, m), 3.78 (3H, s), 3.76 (3H, d).

6-Fluoro-7-(morpholin-4-yl)-2-trifluoromethyl-[1,8]-naphthyridine-3-carboxylic acid, $^1$H NMR (CDCl$_3$) δ: 9.05 (1H, s), 8.70 (1H, s), 8.17 (1H, d), 3.77-3.76 (4H, m), 3.72-3.70 (4H, m).

6-Fluoro-7-propargylamino-2-trifluoromethyl-[1,8]-naphthyridine-3-carboxylic acid, yellow solid. Molecular ion: (MH)$^+$314.

6-Fluoro-7-methyl-2[(2,2,2-trifluoroethoxy)difluoromethyl]-[1,8]-naphthyridine-3-carboxylic acid, yellow solid, $^1$H NMR (CDCl$_3$) δ: 8.81 (1H, s), 8.35 (1H, d), 4.75 (2H, q), 2.43 (3H, d).

2-(1,1-Difluoro-2-methoxyethyl)-6-fluoro-7-methyl-[1,8]-naphthyridine-3-carboxylic acid,
$^1$H NMR (CDCl$_3$+drop d$_6$-DMSO) 8.49 (1H, s), 7.81 (1H, d), 4.34-4.42 (2H, t), 3.55 (3H, s), 2.82 (3H, d).

7-Ethyl-6-fluoro-2-trifluoromethyl-[1,8]-naphthyridine-3-carboxylic acid, yellow solid, $^1$H NMR (CDCl$_3$) δ: 8.99 (1H, s), 8.42 (1H, d), 3.04 (2H, q), 1.31 (3H, t).

6-Fluoro-7-(1-methylethyl)-2-trifluoromethyl-[1,8]-naphthyridine-3-carboxylic acid, yellow solid, $^1$H NMR (CDCl$_3$) δ: 9.02 (1H, s), 8.46 (1H, d), 3.59-3.49 (1H, m), 1.33 (6H, d).

6-Fluoro-7-(2-methylpropyl-2-trifluoromethyl-[1,8]-naphthyridine-3-carboxylic acid, colourless solid, $^1$H NMR (CDCl$_3$) δ: 9.01 (1H, s), 8.45 (1H, d), 2.90 (2H, m), 2.26-2.19 (1H, m), 0.92 (6H, d). Molecular ion: (MH)$^+$317.

7-n.Butyl-6-fluoro-2-trifluoromethyl-[1,8]-naphthyridine-3-carboxylic acid, yellow solid, $^1$H NMR (CDCl$_3$) δ: 8.77 (1H, s), 7.93 (1H, d), 3.17-3.12 (2H, m), 1.91-1.83 (2H, m), 1.53-1.43 (2H, m), 0.98 (3H, t).

6-Fluoro-7-[(E)-prop-1-enyl]-2-trifluoromethyl-[1,8]-naphthyridine-3-carboxylic acid, yellow solid, $^1$H NMR (CDCl$_3$) δ: 8.95 (1H, s), 8.45 (1H, d), 7.38-7.29 (1H, m), 7.89-7.85 (1H, m), 2.01 (3H, double doublet).

6-Fluoro-7-(thiophen-3-yl)-2-trifluoromethyl-[1,8]-naphthyridine-3-carboxylic acid, yellow solid, $^1$H NMR (CDCl$_3$) δ: 9.00 (1H, s), 8.59 (1H, d), 8.55-8.53 m), 7.96-7.94 (1H, m), 7.76-7.74 (1H, m).

6-Fluoro-7-[(4-methoxyphenyl)]-2-trifluoromethyl-[1,8]-naphthyridine-3-carboxylic acid, yellow solid, $^1$H NMR (CDCl$_3$) δ: 8.78 (1H, s), 8.28 (1H, d), 8.04 (1H, d), 7.05 (2H, d), 3.95 (3H, s).

6-Fluoro-7-[(4-fluorophenyl)]-2-trifluoromethyl-[1,8]-naphthyridine-3-carboxylic acid, $^1$H NMR (CDCl$_3$) δ: 9.00 (1H, s), 8.63 (1H, d), 8.16-8.18 (2H, m), 7.42-7.44 (2H m).

5-Fluoro-2-methoxymethyl-[1,8]-naphthyridine-3-carboxylic acid, yellow solid, $^1$H NMR (CDCl$_3$) δ: 9.14 (1H, d), 8.84 (1H, s), 8.55-8.53 (1H, m), 8.43 (1H, double doublet), 4.87 (2H, s), 3.28 (3H, s).

Preparation of 6-fluoro-7-fluoromethyl-2-trifluoromethyl-[1,8]-naphthyridine-3-carboxylic acid Stage 1

In a similar procedure to Example 5, Stage 1, ethyl 6-fluoro-7-methyl-2-trifluoromethyl-[1,8]-naphthyridine-3- carboxylate was oxidised to give ethyl 6-fluoro-7-methyl-8-oxy-2-trifluoromethyl-[1,8]-naphthyridine-1-oxide-3-carboxylate, $^1$H NMR (CDCl$_3$) δ: 8.74 (1H, s), 7.48 (1H, d), 4.50 (2H, q), 2.72 (3H, d), 1.46 (3H, t)

Stage 2

Preparation of ethyl 6-fluoro-7-hydroxymethyl-2-trifluoromethyl-[1,8]-naphthyridine-3-carboxylate To a stirred solution of ethyl 6-fluoro-7-methyl-8-oxy-2-trifluoromethyl-[1,8]-naphthyridine-1-oxide-3-carboxylate (2.00 g) in dry dichloromethane (20 ml) at ambient temperature was added trifluoroacetic anhydride (2.6 ml) drop-wise. During the addition, the mixture gradually became warm until it eventually began to reflux. The reaction was heated at 40° C. for 6 hours then an aqueous 2M solution of potassium carbonate (30 ml) was added and the mixture stirred for a further 1 hour. The organic phase was separated and the aqueous phase extracted with dichloromethane (3×20 ml). The organic extracts were combined, washed with brine, dried over magnesium sulfate, filtered and evaporated under reduced pressure. The residue was purified by chromatography (silica; hexane/ethyl acetate) to give the required product as a yellow solid, 0.800 g, $^1$H NMR (CDCl$_3$) δ: 8.74 (1H, s), 7.94 (1H, d), 5.12 (2H, broad s), 4.51 (2H, q), 4.07 (1H, broad s), (1.46, 3H, t).

Stage 3

Preparation of ethyl 6-fluoro-7-fluoromethyl-2-trifluoromethyl-[1,8]-naphthyridine-3-carboxylate In a similar procedure to Example 12, Stage 3, ethyl 6-fluoro-7-hydroxymethyl-2-trifluoromethyl-[1,8]-naphthyridine-3-carboxylate was reacted with N,N-diethylaminosulfur trifluoride to give the required product. as a pale brown solid, $^1$H NMR (CDCl$_3$) δ: 8.74 (1H, s), 8.03 (1H, d), 5.83 (2H, double doublet), 4.51 (1H, q), 1.45 (3H, t).

Stage 4

In a similar procedure to Example 1, Stage 2, ethyl 6-fluoro-7-fluoromethyl-2-trifluoromethyl-[1,8]-naphthyridine-3-carboxylate was hydrolysed to give the required product as an off-white solid, $^1$H NMR (CDCl$_3$) δ: 8.85 (1H, s), 8.14 (1H, d), 5.83 (2H, double doublet).

Preparation of 7-(1,1-difluoroethyl)-6-fluoro-2-trifluoromethyl-[1,8]-naphthyridine-3-carboxylic acid Stage 1

Preparation of ethyl 7-acetyl-6-fluoro-2-trifluoromethyl-[1,8]-naphthyridine-3-carboxylate To a stirred solution of ethyl 7-chloro-6-fluoro-2-trifluoromethyl-[1,8]-naphthyridine-3-carboxylate (3.00 g) in dry toluene (20 ml) containing tri-n.-butyl(1-ethoxyvinyl)stannane (5 ml) was added bis(triphenylphosphan)palladium(II)-chloride (0.70 g) and the mixture heated to reflux for 3 hours under an atmosphere of nitrogen.

Analysis of a sample of the reaction mixture by LC-MS showed that formation of the required intermediate 7-(1-ethoxyvinyl)naphthyridine was complete. The reaction mixture was treated with aqueous 2M sulphuric acid (10 ml) and reheated to reflux for 10 minutes to form the required 7-acetylnaphthyridine. The mixture was passed through a pad of silica and the filtrate collected. The organic phase was separated, washed with water and dried over magnesium sulfate, filtered and evaporated under reduced pressure to give a brown oil that partially solidified. The material was crystallised from diethyl ether/hexane to afford the required product (0.50 g). $^1$H NMR (CDCl$_3$) δ: 8.75 (1H, s), 8.10 (1H, d), 4.50 (2H, q), 2.92 (3H, s), 1.45 (3H, t). Further slightly less-pure required product (0.4 g) was obtained as a second crop from the recrystallisation liquors on storing.

Stage 2

Preparation of ethyl 7-(1,1-difluoroethyl)-6-fluoro-2-trifluoromethyl-[1,8]-naphthyridine-3-carboxylate In a similar procedure to Example 13, Stage 1, a mixture of ethyl 7-acetyl-6-fluoro-2-trifluoromethyl-[1,8]-naphthyridine-3-carboxylate and N,N-di(2-methoxyethyl)aminosulfur trifluoride was reacted at 50° C. for 2 hours to provide the required product as a colourless solid. $^1$H NMR (CDCl$_3$) δ: 8.74 (1H, s), 8.08 (1H, d), 4.51 (2H, q), 2.25 (3H, t), 1.46 (3H, t); Molecular ion: (MH)$^+$353.

Stage 3

In a similar procedure to Example 1, Stage 2, ethyl 7-(1,1-difluoroethyl)-6-fluoro-2-trifluoromethyl-[1,8]-naphthyridine-3-carboxylate was hydrolysed to the required naphthyridine carboxylic acid as a colourless solid. $^1$H NMR (CDCl$_3$) δ: 9.15 (1H, s), 8.80 (1H, d), 2.20 (3H, t). Molecular ion: (MH)$^+$325.)

Alternative preparation of ethyl 6-fluoro-2-trifluoromethyl-[1,8]-naphthyridine-3-carboxylate Stage 1

Preparation of N-(5-fluoro-pyridin-2-yl)-2,2-dimethylpropionamide

To a stirred solution of 2-amino-5-fluoropyridine (50.0 g, commercially available) and triethylamine (93 ml) in dichloromethane (600 ml) was added pivaloyl chloride (56 ml) at ambient temperature. The slurry that formed was stirred for 3 hours, stored for 18 hours then washed with water (200 ml), brine (100 ml) then dried over magnesium sulfate, filtered and evaporated under reduced pressure to give the required product as a brown oil, 86 g. $^1$H NMR (CDCl$_3$) δ: 8.30 (1H, dd), 8.10 (1H, d), 8.00 (1H, bs), 7.42 (1H, m), 1.30 (9H, s).

In a similar procedure, N-(6-methylpyridin-2-yl)-2,2-dimethylpropionamide was prepared from 2-amino-6-methylpyridine. $^1$H NMR (CDCl$_3$) δ: 8.02-8.04 (1H, d), 7.95 (1H, broad s), 7.54-7.60 (1H, t), 6.86-6.88 (1H, d), 2.44 (3H, s), 1.31 (9H, s). Similarly, N-(5-fluoro-6-methylpyridin-2-yl)-2,2-dimethylpropionamide was prepared from 2-amino-5-fluoro-6-methylpyridine. $^1$H NMR (CDCl$_3$) δ: 8.02 (1H, dd), 7.95 (1H, broad s), 7.35 (1H, t), 2.44 (3H, d), 1.32 (9H, s).

Stage 2

Preparation of N-(5-fluoro-3-formyl-pyridin-2-yl)-2,2-dimethylpropionamide

To a stirred solution of N-(5-fluoro-pyridin-2-yl)-2,2-dimethylpropionamide (39.2 g) in dry diethyl ether (1200 ml) under an atmosphere of nitrogen at −78° C. was added dropwise t.-butyl lithium in hexanes (1.7M, 300 ml). The mixture was stirred at −78° C. for 2 hours then dry N,N-dimethylformamide (160 ml) was added and the slurry stirred at −78° C. for 1 hour then allowed to slowly warm to ambient temperature and stirred for an additional 1 hour. The mixture was quenched with aqueous 2M hydrochloric acid until a clear biphasic solution was formed and the organic phase separated. The aqueous phase was further extracted with diethyl ether. The extracts were combined, washed with brine (300 ml), dried over magnesium sulfate, filtered and evaporated under reduced pressure to give the required product as a pale yellow solid, 40 g. $^1$H NMR (CDCl$_3$) δ: 11.20 (1H, s), 9.94 (1H, s), 8.59 (1H, d), 7.84 (1H, dd), 1.42 (9H, s).

In a similar procedure, N-(3-formyl-6-methylpyridin-2-yl)-2,2-dimethylpropionamide was prepared from N-(6-methylpyridin-2-yl)-2,2-dimethylpropionamide $^1$H NMR (CDCl$_3$) δ: 10.9 (1H, broad s), 9.88 (1H, s), 7.89-7.91 (1H, d), 7.03-7.05 (1H, d), 2.64 (3H, s), 1.38 (9H, s).

Similarly, N-(5-fluoro-3-formyl-6-methylpyridin-2-yl)-2,2-dimethylpropionamide was prepared from N-(5-fluoro-6-methylpyridin-2-yl)-2,2-dimethylpropionamide $^1$H NMR (CDCl$_3$) δ: 10.15 (1H, s), 9.82 (1H, s), 7.68 (1H, d), 2.60 (3H, d), 1.38 (9H, s), Similarly, N-(3-formyl-6-methoxymethylpyridin-2-yl)-2,2-dimethylpropionamide was prepared from N-(6-methoxymethylpyridin-2-yl)-2,2-dimethylpropionamide, brown oil, $^1$H NMR (CDCl$_3$) δ: 9.91 (1H, s), 8.04 (1H, d), 7.36 (1H, d), 4.66 (2H, s), 3.51 (3H, s), 1.37 (9H, s).

Stage 3

Preparation of
2-amino-5-fluoropyridinyl-3-carboxaldehyde

A mixture of N-(5-fluoro-3-formyl-pyridin-2-yl)-2,2-dimethylpropionamide (14.2 g) in aqueous 2M hydrochloric acid (200 ml) was stirred at 100° C. for 45 minutes, cooled to ambient temperature, treated with sodium hydrogen carbonate until the mixture was pH 5 then extracted with dichloromethane (2×100 ml). The extracts were combined, washed with aqueous sodium hydrogen carbonate (50 ml) then water (50 ml), dried over magnesium sulfate, filtered and evaporated under reduced pressure to give the required product as a yellow solid, 6.5 g. $^1$H NMR (CDCl$_3$) δ: 9.82 (1H, s), 8.18 (1H, d), 7.54 (1H, dd), 6.62 (2H, bs).

In a similar procedure, 2-amino-6-methylpyridinyl-3-carboxaldehyde was prepared from N-(3-formyl-6-methylpyridin-2-yl)-2,2-dimethylpropionamide, $^1$H NMR (CDCl$_3$) δ: 9.80 (1H, s), 7.68-7.70 (1H, d), 6.56-6.58 (1H, d), 2.42 (3H, s).

Similarly, 2-amino-5-fluoro-6-methylpyridinyl-3-carboxaldehyde was prepared from N-(5-fluoro-3-formyl-6-methylpyridin-2-yl)-2,2-dimethylpropionamide, $^1$H NMR (CDCl$_3$) δ: 9.78 (1H, s), 7.43 (1H, d), 2.42 (3H, d).

Similarly, 2-amino-6-methoxymethylpyridinyl-3-carboxaldehyde was prepared from N-(3-formyl-6-methoxymethylpyridin-2-yl)-2,2-dimethylpropionamide, $^1$H NMR (CDCl$_3$) δ: 9.84 (1H, s), 7.82 (1H, d), 6.87 (1H, d), 4.43 (2H, s), 3.48 (3H, s).

Stage 4

A mixture of 2-amino-5-fluoropyridinyl-3-carboxaldehyde (6.5 g), ethyl 4,4,4-trifluoroacetoacetate (7.3 ml) and piperidine (0.465 ml, catalyst) in ethanol (70 ml) were heated to reflux with stirring for 16 hours The mixture was cooled to ambient temperature and the pale yellow crystals that had formed were filtered from solution, washed with a small amount of ethanol and sucked to dryness to give the required product, 5.7 g, identical by NMR to the product obtained in Example 4, Stage 4.

The following compounds were prepared in a similar procedure:

From 2-amino-5-fluoropyridinyl-3-carboxaldehyde and methyl 4-methoxyacetoacetate to give methyl 5-fluoro-2-methoxymethyl-[1,8]-naphthyridine-3-carboxylate, yellow solid, $^1$H NMR (CDCl$_3$) δ: 9.09 (1H, d), 8.65 (1H, s), 7.87 (1H, double doublet), 5.08 (2H, s), 4.01 (3H, s), 3.45 (3H, s). Molecular ion: (MH)$^+$251.

From 2-amino-5-fluoro-6-methylpyridinyl-3-carboxaldehyde and ethyl 4,4-difluoroacetoacetate to give ethyl 2-difluoromethyl-6-fluoro-7-methyl-[1,8]-naphthyridine-3-carboxylate, $^1$H NMR (CDCl$_3$) δ: 8.82 (1H, s), 7.84 (1H, d), 7.42 (1H, t), 4.50 (2H, q), 2.86 (3H, d), 1.47 (3H, t).

From 2-amino-5-fluoro-6-methylpyridinyl-3-carboxaldehyde and methyl 4-methoxyacetoacetate to give methyl 2-methoxymethyl-6-fluoro-7-methyl-[1,8]-naphthyridine-3-carboxylate, $^1$H NMR (CDCl$_3$) δ: 8.61 (1H, s), 7.77 (1H, d), 5.06 (2H, d), 4.00 (3H, s), 3.43 (3H, s), 2.81 (3H, d).

From 2-amino-5-fluoro-6-methylpyridinyl-3-carboxaldehyde and methyl 4-chloro-4,4-difluoroacetoacetate to give methyl 2-chloro-2,2-difluoromethyl-6-fluoro-7-methyl-[1,8]-naphthyridine-3-carboxylate $^1$H NMR (CDCl$_3$) δ: 8.57 (1H, s), 7.82 (1H, d), 4.02 (3H, s), 2.88 (3H, s).

From 2-amino-5-fluoro-6-methylpyridinyl-3-carboxaldehyde and ethyl 4-(2,2,2-trifluoroethoxy)-4,4-difluoroacetoacetate to give ethyl 6-fluoro-7-methyl-2[(2,2,2-trifluoroethoxy)difluoromethyl]-[1,8]-naphthyridine-3-carboxylate, yellow solid, $^1$H NMR (CDCl$_3$) δ: 8.53 (1H, s), 7.82 (1H, d), 4.49-4.43 (4H, m), 2.85 (3H, d), 1.42 (3H, t).

From 2-amino-5-fluoro-6-methylpyridinyl-3-carboxaldehyde and ethyl 4,4-difluoro-5-methoxy-3-oxopentanoate to give ethyl 2-(1,1-difluoro-2-methoxyethyl)-6-fluoro-7-methyl-[1,8]-naphthyridine-3-carboxylate, yellow gum, $^1$H NMR (CDCl$_3$) δ: 8.42 (1H, s), 7.80 (1H, d), 4.44-4.50 (2H, q), 4.35-4.41 (2H, t), 3.54 (3H, s), 2.84 (3H, d), 1.42-1.46 (3H, t).

From 2-amino-5-fluoro-6-methylpyridinyl-3-carboxaldehyde and ethyl 4,4-difluoro-4-iodoacetoacetate to give ethyl 2-difluoroiodomethyl-6-fluoro-7-methyl-[1,8]-naphthyridine-3-carboxylate, yellow solid, $^1$H NMR (CDCl$_3$) δ: 8.48 (1H, s), 7.81 (1H, d), 4.46-4.52 (2H, q), 2.84 (3H, d), 1.44-1.50 (3H, t).

Preparation of N-(6-methoxymethylpyridin-2-yl)-2,
2-dimethylpropionamide

A mixture of 2-bromo-6-methoxymethylpyridine [1.00 g; *J Heterocyclic Chem.*, 30, 563, (1993)], pivaloyl amide (0.756 g), palladium acetate (0.112 g), cesium carbonate (2.40 g), 4.5-bis(diphenylphosphino)-9,9-dimethylxanthene (0.434 g) and 1,4-dioxan (5 ml) were sealed in a microwave vial and heated in a microwave oven with stirring for 30 minutes at 150° C. This process was repeated with a second batch of reagents and the products combined, the insoluble material filtered from solution and the filtrate evaporated under reduced pressure. The residue was purified by chromatography (silica; hexane/ethyl acetate) to afford the desired product as a yellow oil, 1.75 g. $^1$H NMR (CDCl$_3$) δ: 9.84 (1H, s), 7.82 (1H, d), 6.87 (1H, d), 4.43 (2H, s), 3.48 (3H, s).

Preparation of ethyl 6-fluoro-7-(thiophen-3-yl)-2-trifluoromethyl-[1,8]-naphthyridine-3-carboxylate To a stirred mixture of ethyl 6-fluoro-[1,8]-naphthyridine-8-oxy-3-carboxylate (0.50 g) and thiophene-3-boronic acid in toluene (10 ml) was heated to reflux for 16 hours then cooled to ambient temperature. The mixture was diluted with ethyl acetate (10 ml), washed with water then brine and dried over magnesium sulfate, filtered and evaporated under reduced pressure. The residue was purified by chromatography (silica; hexane/ethyl acetate) to give the required product as a yellow solid, 0.34 g, $^1$H NMR (CDCl$_3$) δ: 8.67 (1H, s), 8.50 (1H, m), 8.20 (1H, double triplet), 7.99 (1H, d), 7.48 (1H, double doublet), 4.50 (2H, q), 1.45 (3H, t). Molecular ion: (MH)$^+$371.

The following compounds were prepared in a similar procedure from the corresponding boronic acids:

Ethyl 6-fluoro-7-[(E)-styryl]-2-trifluoromethyl-[1,8]-naphthyridine-3-carboxylate, $^1$H NMR (CDCl$_3$) δ: 8.65 (1H, s), 8.46 (1H, d), 7.89 (1H, d), 7.73-7.71 (2H, m), 7.58 (1H, double doublet), 7.47-7.41 (3H, m), 4.49 (2H, q), 1.45 (3H, t).

Ethyl 6-fluoro-7-[(4-fluorophenyl)]-2-trifluoromethyl-[1,8]-naphthyridine-3-carboxylate, yellow solid, $^1$H NMR (CDCl$_3$) δ: 8.71 (1H, s), 8.32-8.39 (2H, m), 8.04 (1H, d), 7.23-7.27 (2H, m), 4.51 (2H, q), 1.46 (3H, t). Molecular ion: (MH)$^+$383

Ethyl 6-fluoro-7-[(4-methoxyphenyl)]-2-trifluoromethyl-[1,8]-naphthyridine-3-carboxylate, yellow solid, $^1$H NMR (CDCl$_3$) δ: 8.66 (1H, s), 8.35 (2H, d), 7.95 (1H, d), 7.05 (2H, d), 4.49 (2H, q), 3.92 (3H, s), 1.45 (3H, t).

Preparation of ethyl 6-fluoro-7-(1-methylethyl)-2-trifluoromethyl-[1,8]-naphthyridine-3-carboxylate To a stirred solution of ethyl 6-fluoro-8-oxy-[1,8]-naphthyridine-1-oxide-3-carboxylate (0.50 g) in dry tetrahydrofuran (5 ml) at ambient temperature under an atmosphere of nitrogen was added a solution of isopropyl magnesium chloride (2 ml, 2M solution in tetrahydrofuran). The mixture was stirred for 3 hours, quenched with water and acidified with aqueous 2M hydrochloric acid then extracted into ethyl acetate (3 times). The extracts were combined, washed with brine, dried over magnesium sulfate, filtered and evaporated under reduced pressure to give a brown oil. The oil was dissolved in acetic anhydride (5 ml) with stirring and heated to 110° C. for 1 hour then cooled to ambient temperature. The product was purified by chromatography (silica; hexane/ethyl acetate) to give the required product, 0.13 g, as a yellow solid. $^1$H NMR (CDCl$_3$) δ: 8.70 (1H, s), 7.89 (1H, d), 4.53 2H, q), 3.74-3.64 (1H, m), 1.52 (6H, s), 1.49 (3H, t). Molecular ion: (MH)$^+$331.

The following compound was prepared in a similar procedure:

Ethyl 7-cyclopropyl-6-fluoro-2-trifluoromethyl-[1,8]-naphthyridine-3-carboxylate, pale yellow solid, $^1$H NMR (CDCl$_3$) δ: 8.62 (1H, s), 7.79 (1H, d), 4.47 (2H, q), 2.63-2.57 (1H, m), 1.62-1.57 (2H, m), 1.44 (3H, t), 1.32-1.27 (2H, m); Molecular ion: (MH)$^+$329.

Preparations of Diones

Preparation of 8-oxa-bicyclo[3.2.1]octane-2,4-dione

Stage 1

Preparation of 2,3,4,4-tetrachloro-8-oxa-bicyclo[3.2.1]octa-2,6-diene

A stirred mixture of 1,2,3,3-tetrachlorocyclopropene (60 g) and furan (22.97 g) in dry toluene (600 ml) was heated to reflux for 30 hours. The solvent was evaporated under reduced pressure to afford the required product, 75.4 g. $^1$H NMR (CDCl$_3$) δ: 6.90 (1H, dd), 6.45 (1H, dd), 5.41 (1H, d), 4.93 (1H, d).

Stage 2

Preparation of 3-chloro-8-oxa-bicyclo[3.2.1]oct-6-ene-2,4-dione

A mixture of 2,3,4,4-tetrachloro-8-oxa-bicyclo[3.2.1]octa-2,6-diene (20 g) and concentrated sulfuric acid (100 ml) was stirred and heated to 100° C. for 30 minutes then poured onto ice and extracted with chloroform. The solvent was evaporated under reduced pressure, dried over magnesium sulfate, filtered and the residue triturated with diethyl ether. The solid obtained was filtered from solution and sucked to dryness to afford the required product, 6.44 g, as a colourless solid. $^1$H NMR (CDCl$_3$) δ: 6.40 (2H, m), 5.90 (1H, s), 5.48 (2H, m).

Stage 3

Preparation of 8-oxa-bicyclo[3.2.1]oct-6-ene-2,4-dione

To a stirred suspension of 3-chloro-8-oxa-bicyclo[3.2.1]oct-6-ene-2,4-dione (6.44 g) in aqueous hydrochloric acid (35 ml, 2M) was added zinc powder (4.88 g) in portions maintaining the reaction temperature below 25° C. by cooling with an icebath. After 45 minutes, the mixture was filtered through a bed of celite then extracted with ethyl acetate. the extract was dried over magnesium sulfate, filtered and evaporated under reduced pressure to afford the required product. $^1$H NMR (d$_6$-DMSO) δ: 6.50 (2H, s), 5.18 (2H, s), 4.15 (1H, d), 3.34 (1H, d).

Stage 4

To a stirred solution of 8-oxa-bicyclo[3.2.1]oct-6-ene-2,4-dione (5.1 g) in ethanol (100 ml) was added palladium on charcoal (0.51 g, 5% by wt. catalyst) and the mixture hydrogenated at ambient temperature and pressure over 6 hours. The catalyst was removed by filtration and the solvent evaporated under reduced pressure to afford the required product containing some ethyl enolether of the required product.

$^1$H NMR (d$_6$-DMSO) δ: 4.92 (1H, s), 4.40 (2H, m), 2.05 (2H, m), 1.64 (2H, m). The product was used in subsequent reactions without further purification.

Thus, according to the present invention there is further provided a method of making a compound of Formula (Ia) or (Ib) wherein Q=Q1 which comprises reacting together a compound of Formula (Ia') or (Ib')

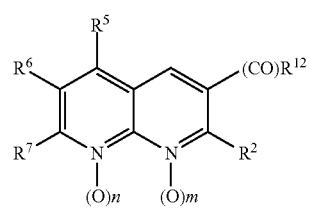

Ia'

-continued

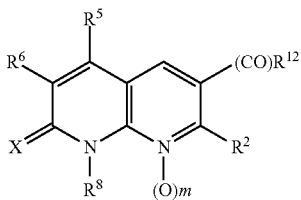
Ib' wherein the various substituents are as defined previously, and wherein $R^{12}$ is halogen or aryloxy with a compound of Formula (II)

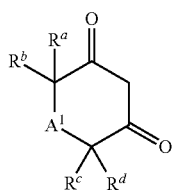
(II)

wherein the various substituents are as defined previously, in the presence of an inert organic solvent and a base. The method may further comprise a subsequent rearrangement step known to the skilled person using, for example, a suitable catalyst, for example acetone cyanhydrin.

Preferably $R^{12}$ is selected from the group consisting of fluorine, chlorine, bromine, and 4-nitrophenoxy. In an especially preferred embodiment $R^{12}$ is chlorine.

The present invention still further provides a compound of Formula (IIIa) or (IIIb)

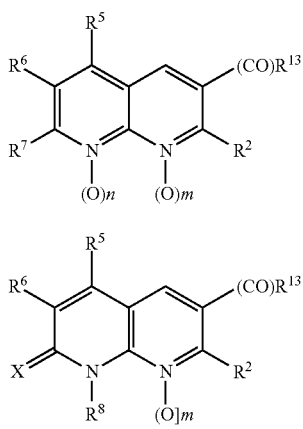

IIIa

IIIb wherein
$R^2$ is haloalkyl, in particularly fluoroalkyl, and most preferably difluoromethyl or trifluoromethyl;
$R^5$ is hydrogen or methyl, preferably hydrogen;
$R^6$ is selected from the group consisting of hydrogen, fluorine, chlorine, hydroxyl and methyl, preferably hydrogen or fluorine;
$R^8$ is selected from the group consisting of hydrogen, $C_1$-$C_6$alkyl, $C_1$-$C_3$alkoxy$C_1$-$C_3$alkylenyl and $C_1$-$C_6$haloalkyl, n and m are as defined above and wherein $R^{13}$ is selected from the group consisting of halogen, $C_1$-$C_6$-alkoxy, aryloxy, OH, $O^-M^+$ wherein $M^+$ is an alkali metal cation (preferably sodium) or an ammonium cation, and wherein $R^7$ is selected from the group consisting of hydrogen, hydroxyl, halogen, $C_1$-$C_6$alkyl, $C_3$-$C_6$cycloalkyl, $C_1$-$C_6$haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl, $C_1$-$C_6$-alkoxy-$C_2$-$C_6$-alkoxy-$C_1$-$C_6$ alkyl $C_1$-$C_6$alkylamino, $C_1$-$C_6$dialkylamino, $C_2$-$C_6$alkenylamino, $C_1$-$C_6$alkoxyalkylamino, ($C_1$-$C_6$alkoxyalkyl)alkylamino, $C_3$-$C_6$cycloalkylamino, $C_3$-$C_6$ cyclohaloalkylamino, $C_1$-$C_3$alkoxy-$C_3$-$C_6$ cycloalkylamino, $C_3$-$C_6$ alkynylamino and a dialkylamino group in which the substituents join to form a 4-6 membered ring, optionally containing oxygen, or optionally substituted by $C_1$-$C_3$-alkoxy or halogen, especially fluorine. In an even more preferred embodiment $R^7$ is selected from the group consisting of hydrogen, methyl, ethyl, 1-chloroethyl, 1,1-dichloroethyl, fluoromethyl, difluoromethyl, trifluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, methoxyethyl, ethoxyethoxy, ethoxyethoxymethyl, methoxyethoxy, methoxyethoxymethyl, (2-methoxyethyl)amino and (2-ethoxyethyl)methylamino with the exception of compounds of Formula (IIIa) wherein $R^5$, $R^6$ and $R^7$ are hydrogen, m and n are 0, $R^2$ is $CF_3$ and $R^{13}$ is OH, ethoxy or methoxy;

A particularly preferred embodiment of the present invention is wherein the compound is of Formula (IIIa) and wherein n is 0, m is 0, $R^2$ is $CF_3$, $R^5$=H, $R^6$=H or F, $R^7$ is selected from the group consisting of methyl, ethyl, fluoromethyl, difluoromethyl, trifluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, methoxyethyl, ethoxyethoxy, ethoxyethoxymethyl, methoxyethoxy and methoxyethoxymethyl, and $R^{13}$ is selected from the group consisting of ethoxy, chlorine and hydroxyl.

The present invention still further provides a method of making a compound of Formula (IV):—

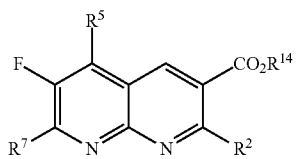
IV wherein $R^2$, $R^5$ and $R^7$ are as defined previously and wherein $R^{14}$=$C_1$-$C_4$alkyl; which comprises reacting a compound of Formula (V)

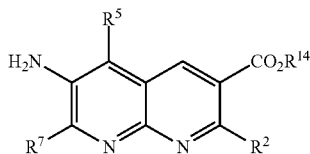
V with a compound selected from the group consisting of HF, aqueous $HBF_4$, HF.pyridine and HF.triethylamine which may also be used as the reaction solvent in the presence of aqueous sodium nitrite or an alkyl nitrite ester such as t.butyl nitrite. In a preferred embodiment $R^{14}$ is methyl or ethyl.

The present invention still further provides a method of making a compound of Formula (VI) or Formula (VII)

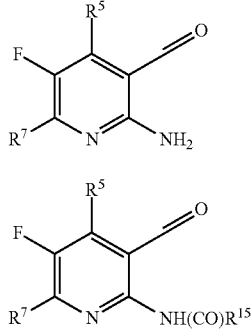

wherein $R^5$ and $R^7$ are as previously described and $R^{15}$ is $C_1$-$C_6$ alkyl, preferably t.butyl, from a compound of Formula (VIII)

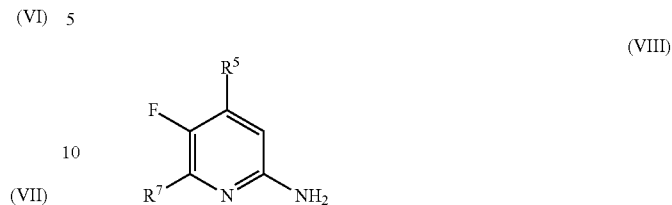

using a strong base (such as t.butyl lithium) and a formyl transfer agent (such as N,N-dimethyl formamide).

The present invention further provides the use of a compound of Formula (Ia) or (Ib) as a herbicide.

Examples of specific compounds of the present invention.

TABLE 1

| Compound | $R^2$ | $R^5$ | $R^6$ | $R^7$ |
|---|---|---|---|---|
| 1.1 | $CF_3$ | H | H | H |
| 1.2 | $CF_3$ | H | H | $CH_3$ |
| 1.3 | $CF_3$ | H | H | Et, |
| 1.4 | $CF_3$ | H | H | n-Propyl |
| 1.5 | $CF_3$ | H | H | i-Propyl |
| 1.6 | $CF_3$ | H | H | c-Propyl |
| 1.7 | $CF_3$ | H | H | n-Butyl |
| 1.8 | $CF_3$ | H | H | i-Butyl |
| 1.9 | $CF_3$ | H | H | s-Butyl |
| 1.10 | $CF_3$ | H | H | c-Butyl |
| 1.11 | $CF_3$ | H | H | $CH_2F$ |
| 1.12 | $CF_3$ | H | H | $CF_2H$ |
| 1.13 | $CF_3$ | H | H | $CF_3$ |
| 1.14 | $CF_3$ | H | H | $C_2F_5$ |
| 1.15 | $CF_3$ | H | H | $CH_2OCH_3$ |
| 1.16 | $CF_3$ | H | H | O-cPentyl |
| 1.17 | $CF_3$ | H | H | O—Ph |
| 1.18 | $CF_3$ | H | H | $OCH(CH_3)CH_2CH_2CH_2CH_3$ |
| 1.19 | $CF_3$ | H | F | $OCH_2CH_3$ |
| 1.20 | $CF_3$ | H | H | $SO_2Me$ |
| 1.21 | $CF_3$ | H | H | OH |
| 1.22 | $CF_3$ | H | H | $OCH(CH_3)_2$ |
| 1.23 | $CF_3$ | H | H | $OCH_3$ |
| 1.24 | $CH_3$ | H | H | $CF_3$ |
| 1.25 | $CF_3$ | H | $CH_3$ | H |
| 1.26 | $CF_3$ | H | H | $OC_2H_5$ |
| 1.27 | $CF_3$ | H | H | Cl |
| 1.28 | $CF_3$ | H | F | H |
| 1.29 | $C_2F_5$ | H | H | H |
| 1.30 | $C_2F_5$ | H | H | $OC_2H_5$ |
| 1.31 | $CH_2F$ | H | H | $OC_2H_5$ |
| 1.32 | $CF_3$ | H | Cl | H |
| 1.33 | $CH_3$ | H | H | H |
| 1.34 | $CF_2H$ | H | H | H |
| 1.35 | $CF_3$ | H | H | $CHFCH_3$ |
| 1.36 | $CF_3$ | H | H | $CF_2CH_3$ |
| 1.37 | $CF_3$ | H | H | $CF(CH_3)_2$ |
| 1.38 | $CF_3$ | H | F | $CHFCH_3$ |
| 1.39 | $CF_3$ | H | F | $CF_2CH_3$ |
| 1.40 | $CF_3$ | H | F | $CF(CH_3)_2$ |
| 1.41 | $CF_3$ | H | F | $CH_3$ |
| 1.42 | $CH_2F$ | H | F | H |

TABLE 1-continued

| Compound | R² | R⁵ | R⁶ | R⁷ |
|---|---|---|---|---|
| 1.43 | CH₂F | H | F | H |
| 1.44 | CH₂F | H | F | H |
| 1.45 | CF₃ | H | H | morpholin-4-yl (N-linked morpholine) |
| 1.46 | CF₃ | H | H | 6-fluoropyridin-3-yl |
| 1.47 | CH₂F | H | H | H |
| 1.48 | CH₂F | H | H | H |
| 1.49 | CF₃ | H | H | —O—CH₂—CH₂—O—CH₃ |
| 1.50 | CF₃ | H | H | —O—CH₂—CF₃ |
| 1.51 | CF₃ | H | H | —O—CH₂—CH=CH₂ |
| 1.52 | CF₃ | H | H | —SCH₃ |
| 1.53 | CF₃ | H | F | —O—CH₂—CH₃ |
| 1.54 | CF₃ | H | F | OH |
| 1.55 | CF₃ | H | H | —O—CH₂C≡C—CH₃ |
| 1.56 | CF₃ | H | H | OCH(CH₃)CH₂CH₂CH₃ |
| 1.57 | CF₃ | H | H | —O—CH₂CH₂Ph |
| 1.58 | CF₃ | H | H | —OCH₂CH₂C(O)OCH₂CH₃ |
| 1.59 | CF₃ | H | H | —O—CH₂—CH₂—CH₃ |
| 1.60 | CF₃ | H | H | —O—CH₂-cPropyl |
| 1.61 | CF₃ | H | H | —O—CH₂C(O)—C(CH₃)₃ |
| 1.62 | CF₃ | CH₃ | F | H |
| 1.63 | CF₃ | H | H | —CH(CH₃)OCH₃ |
| 1.64 | CF₃ | H | OH | H |
| 1.65 | CF₃ | H | F | 4-fluorophenyl |
| 1.66 | CF₃ | H | F | 4-methoxyphenyl |
| 1.67 | CF₃ | H | F | —CH₂—CH₃ |
| 1.68 | CF₃ | H | F | (E)-2-phenylethenyl |
| 1.69 | CF₃ | H | F | —CH₂—CH₂F |
| 1.70 | CF₃ | H | F | —CH₂—CH(CH₃)₂ |
| 1.71 | CF₃ | H | F | thiophen-3-yl |
| 1.72 | CF₃ | H | F | —CH=CH—CH₃ |
| 1.73 | CF₃ | H | F | —N(C₂H₅)₂ |
| 1.74 | CH₂OCH₃ | H | F | H |
| 1.75 | CF₃ | H | F | i-Propyl |
| 1.76 | CF₃ | H | F | c-Propyl |
| 1.77 | CH₂OCH₃ | H | F | —CH₃ |
| 1.78 | CF₂H | H | F | —CH₃ |

TABLE 1-continued

| Compound | R² | R⁵ | R⁶ | R⁷ |
|---|---|---|---|---|
| 1.79 | CF₃ | H | F | morpholin-4-yl |
| 1.80 | CF₃ | H | F | N(CH₃)CH₂CH₂OCH₃ |
| 1.81 | CF₃ | H | F | N(CH₃)CH₂CH₃ |
| 1.82 | CF₃ | H | F | N(CH₃)₂ |
| 1.83 | CF₃ | H | F | NHCH₂CH₂OCH₃ |
| 1.84 | CF₃ | H | F | NHCH₂CH₃ |
| 1.85 | CF₂H | H | H | CH₃ |
| 1.86 | CF₃ | H | F | n-Butyl |
| 1.87 | CF₂Cl | H | F | CH₃ |
| 1.88 | CF₃ | CH₃ | F | CH₃ |
| 1.89 | CF₂Cl | H | H | CH₃ |
| 1.90 | CF₃ | H | F | NHCH₂CF₃ |
| 1.91 | CF₂OCH₂CF₃ | H | F | CH₃ |
| 1.92 | CF₃ | H | F | —NH-c-propyl |
| 1.93 | CF₂CH₂OCH₃ | H | F | CH₃ |
| 1.94 | —CF₂CF₃ | H | F | CH₃ |
| 1.95 | CF₂OCH₃ | H | F | CH₃ |
| 1.96 | CF₃ | H | F | 3,3-difluoroazetidin-1-yl |
| 1.97 | CF₃ | H | F | 3-methoxyazetidin-1-yl |
| 1.98 | CF₃ | H | F | NHCH₃ |
| 1.99 | CF₃ | H | H | Br |
| 1.100 | CH₂OCH₃ | H | H | CF₃ |
| 1.101 | CF₂OCH₂CH₂OCH₃ | H | F | CH₃ |
| 1.102 | CF₂OCH₂CH₃ | H | F | CH₃ |
| 1.103 | CF₃ | H | F | —NHCH₂C≡CH |
| 1.104 | (CH₃)CF₂OCH₂-(tetrahydrofuran-2-yl) | H | F | CH₃ |
| 1.105 | (CH₃)CF₂OCH₂-(tetrahydrofuran-3-yl) | H | F | CH₃ |
| 1.106 | CF₂OCH(CH₃)₂ | H | F | CH₃ |
| 1.107 | —C₂H₅ | H | H | CF₃ |
| 1.108 | CH₂N(CH₃)SO₂CH₃ | H | H | CF₃ |

TABLE 2

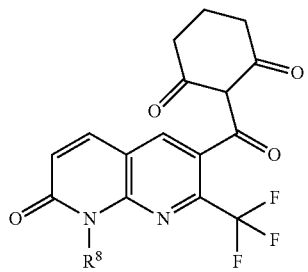

| Compound | R[8] |
|---|---|
| 2.1 | —CH$_2$-(3-methyl-isoxazol-5-yl) |
| 2.2 | —CH$_2$CH$_2$CHCF$_2$ |
| 2.3 | —CH$_2$CN |
| 2.4 | —CH$_2$CF$_2$ |
| 2.5 | —CH$_2$OCH$_3$ |
| 2.6 | —CH$_2$COPh |
| 2.7 | —CH$_2$(CO)C(CH$_3$)$_3$ |
| 2.8 | -Cyclopentyl |
| 2.9 | —CH$_2$cPr |
| 2.10 | —CH(CH$_3$)$_2$ |
| 2.11 | —CH$_2$CH$_2$F |
| 2.12 | —CH$_2$-(2-fluorophenyl) |
| 2.13 | —CH$_2$CH$_2$CH$_3$ |
| 2.14 | —CH$_2$CHCH$_2$ |
| 2.15 | —CH$_2$CH$_2$Ph |
| 2.16 | —CH$_2$CH$_2$OCH$_2$CH$_3$ |
| 2.17 | —CH$_2$CH$_2$OPr |
| 2.18 | —CH$_2$-(tetrahydrofuran-2-yl) |
| 2.19 | —CH$_2$CCH$_3$ |
| 2.20 | —CH$_2$Ph |
| 2.21 | —CH$_3$ |
| 2.22 | —CH$_2$CH$_2$OCH$_3$ |

TABLE 3

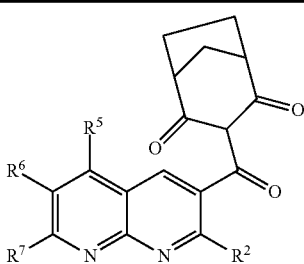

| Compound | R[2] | R[5] | R[6] | R[7] |
|---|---|---|---|---|
| 3.1 | CF$_3$ | H | F | OH |
| 3.2 | CF$_3$ | H | H | OH |
| 3.3 | CF$_3$ | H | H | H |
| 3.4 | CF$_3$ | H | F | OCH$_2$CH$_3$ |
| 3.5 | CF$_3$ | CH$_3$ | F | H |

TABLE 3-continued

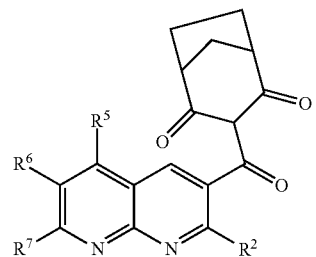

| Compound | R[2] | R[5] | R[6] | R[7] |
|---|---|---|---|---|
| 3.6 | CF$_3$ | H | H | —O—CH$_3$ |
| 3.7 | CF$_3$ | H | H | —OCH$_2$CH$_3$ |
| 3.8 | CF$_3$ | H | H | OH |
| 3.9 | CF$_3$ | H | F | H |
| 3.10 | CF$_3$ | H | H | —CH$_2$CH$_2$F |
| 3.11 | CF$_3$ | H | H | —CH(CH$_3$)CH$_2$F |
| 3.12 | CF$_3$ | H | F | —CH$_3$ |
| 3.13 | CF$_2$CH$_2$OCH$_3$ | H | F | —CH$_3$ |

TABLE 4

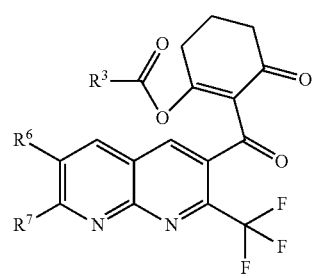

| Compound | R[3] | R[6] | R[7] |
|---|---|---|---|
| 4.1 | —CH(CH$_3$)$_2$ | H | H |
| 4.2 | —CH(CH$_3$)$_2$ | H | CH$_3$ |
| 4.3 | —CH(CH$_3$)$_2$ | H | Et, |
| 4.4 | —CH(CH$_3$)$_2$ | H | n-Propyl |
| 4.5 | —CH(CH$_3$)$_2$ | H | i-Propyl |
| 4.6 | —CH(CH$_3$)$_2$ | H | c-Propyl |
| 4.7 | —CH(CH$_3$)$_2$ | H | n-Butyl |
| 4.8 | —CH(CH$_3$)$_2$ | H | i-Butyl |
| 4.9 | —CH(CH$_3$)$_2$ | H | s-Butyl |
| 4.10 | —CH(CH$_3$)$_2$ | H | c-Butyl |
| 4.11 | —CH(CH$_3$)$_2$ | H | CH$_2$F |
| 4.12 | —CH(CH$_3$)$_2$ | H | CF$_2$H |
| 4.13 | —CH(CH$_3$)$_2$ | H | CF$_3$ |
| 4.14 | —CH(CH$_3$)$_2$ | H | C$_2$F$_5$ |
| 4.15 | —CH(CH$_3$)$_2$ | H | CH$_2$OCH$_3$ |
| 4.16 | —CH(CH$_3$)$_2$ | H | O-cPentyl |
| 4.17 | —CH(CH$_3$)$_2$ | H | O—Ph |
| 4.18 | —CH(CH$_3$)$_2$ | H | OCH(CH$_3$)CH$_2$CH$_2$CH$_3$ |
| 4.19 | —CH(CH$_3$)$_2$ | H | OCH$_2$CH$_3$ |
| 4.20 | —C(CH$_3$)$_3$ | F | CH$_3$ |
| 4.21 | —CH(CH$_3$)$_2$ | F | CH$_3$ |
| 4.22 | n-heptyl | F | CH$_3$ |

TABLE 5

| Compound | R⁵ | R⁶ | R⁷ |
|---|---|---|---|
| 5.1 | H | H | H |
| 5.2 | H | F | CH₃ |

TABLE 6

| Compound | R⁵ | R⁶ | R⁷ |
|---|---|---|---|
| 6.1 | H | H | H |
| 6.2 | H | H | —O—CH₂—CH₃ |
| 6.3 | H | H | OH |

TABLE 7

| Compound | R⁵ | R⁶ | R⁷ |
|---|---|---|---|
| 7.1 | H | H | H |

TABLE 8

| Compound | R⁵ | R⁶ | R⁷ |
|---|---|---|---|
| 8.1 | H | H | H |
| 8.2 | H | H | CHFCH₃ |

TABLE 9

| Compound | R⁵ | R⁶ | R⁷ |
|---|---|---|---|
| 9.1 | H | H | H |

TABLE 10

| Compound | R⁵ | R⁶ | R⁷ |
|---|---|---|---|
| 10.1 | H | H | H |

TABLE 11

| Compound | R⁵ | R⁶ | R⁷ |
|---|---|---|---|
| 11.1 | H | H | H |
| 11.2 | H | F | CH₃ |

TABLE 12

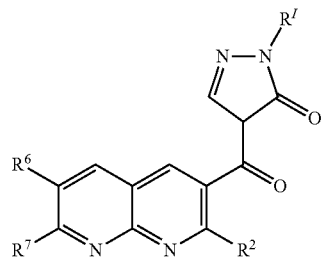

| Compound | $R^i$ | $R^2$ | $R^6$ | $R^7$ |
|---|---|---|---|---|
| 12.1 | —CH$_2$CH$_3$ | CF$_3$ | H | —OCH$_2$CH$_3$ |
| 12.2 | —CH$_2$CH$_3$ | CF$_3$ | H | OH |
| 12.3 | —CH$_3$ | CF$_3$ | H | H |
| 12.4 | —CH$_3$ | CF$_3$ | H | CHFCH$_3$ |
| 12.5 | —CH$_2$CH$_3$ | CF$_2$CH$_2$OCH$_3$ | F | —CH$_3$ |

BIOLOGICAL EXAMPLES

Seeds of a variety of test species were sown in standard soil in pots (*Alopecurus myosuroides* (ALOMY), *Setaria faberi* (SETFA), *Echinochloa crus-galli* (ECHCG), *Solanum nigrum* (SOLNI) and *Amaranthus retoflexus* (AMARE)). After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds were applied at 1000 g/ha. The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

|  | POST Application | | | | | PRE Application | | | | |
|---|---|---|---|---|---|---|---|---|---|---|
| Compound | SOLNI | AMARE | SETFA | ALOMY | ECHCG | SOLNI | AMARE | SETFA | ALOMY | ECHCG |
| 1.3 | 90 | 100 | 90 | 70 | 80 | 100 | 90 | 80 | 80 | 100 |
| 1.11 | 100 | 100 | 90 | 70 | 90 | 100 | 80 | 100 | 60 | 100 |
| 1.12 | 100 | 60 | 100 | 100 | 100 | 100 | 100 | 100 | 90 | 100 |
| 1.16 | 90 | 70 | 90 | 70 | 70 | 90 | 80 | 90 | 60 | 90 |
| 1.17 | 100 | 70 | 100 | 90 | 90 | 100 | 100 | 100 | 100 | 100 |
| 1.20 | 100 | 80 | 100 | 20 | 90 | 100 | 30 | 80 | 20 | 70 |
| 1.21 | 100 | 100 | 100 | 100 | 100 | 100 | 100 | 100 | 80 | 100 |
| 1.35 | 90 | 100 | 90 | 90 | 90 | 100 | 100 | 100 | 70 | 100 |
| 1.36 | 100 | 100 | 90 | 90 | 90 | 100 | 100 | 100 | 70 | 90 |
| 1.37 | 70 | 100 | 90 | 80 | 90 | 100 | 100 | 100 | 80 | 100 |
| 1.41 | 90 | 100 | 100 | 90 | 90 | 100 | 100 | 100 | 90 | 100 |
| 1.56 | 80 | 70 | 80 | 30 | 70 | 100 | 40 | 90 | 20 | 80 |
| 1.62 | 80 | 50 | 70 | 0 | 70 | 60 | 20 | 30 | 0 | 50 |
| 1.63 | 80 | 100 | 90 | 90 | 90 | 100 | 100 | 100 | 70 | 100 |
| 1.66 | 100 | 80 | 90 | 60 | 80 | 90 | 40 | 90 | 50 | 90 |
| 1.67 | 100 | 80 | 90 | 90 | 90 | 100 | 100 | 100 | 90 | 100 |
| 1.69 | 80 | 90 | 80 | 60 | 80 | 100 | 20 | 90 | 60 | 100 |
| 1.70 | 80 | 90 | 90 | 90 | 90 | 100 | 40 | 100 | 90 | 100 |
| 1.71 | 70 | 100 | 80 | 30 | 80 | 70 | 0 | 70 | 10 | 90 |
| 1.72 | 60 | 70 | 80 | 50 | 70 | 90 | 60 | 90 | 30 | 90 |
| 1.73 | 70 | 70 | 80 | 60 | 80 | 100 | 70 | 100 | 60 | 100 |
| 1.74 | 80 | 90 | 80 | 40 | 80 | 100 | 100 | 100 | 70 | 100 |
| 1.75 | 90 | 80 | 90 | 80 | 90 | 90 | 80 | 90 | 80 | 90 |
| 1.78 | 80 | 100 | 90 | 60 | 90 | 100 | 100 | 100 | 80 | 100 |
| 1.79 | 70 | 90 | 90 | 80 | 90 | 100 | 100 | 100 | 90 | 100 |
| 1.80 | 80 | 80 | 80 | 80 | 90 | 100 | 100 | 100 | 80 | 100 |
| 1.81 | 80 | 90 | 80 | 70 | 90 | 100 | 100 | 100 | 70 | 100 |
| 1.83 | 80 | 80 | 80 | 80 | 80 | 100 | 100 | 100 | 60 | 100 |
| 1.84 | 80 | 80 | 80 | 70 | 80 | 100 | 100 | 100 | 60 | 100 |
| 1.85 | 80 | 80 | 80 | 50 | 80 | 100 | 90 | 80 | 10 | 100 |
| 1.86 | 90 | 100 | 90 | 70 | 80 | 100 | 100 | 100 | 80 | 100 |
| 1.87 | 90 | 80 | 80 | 70 | 90 | 100 | 100 | 100 | 60 | 100 |
| 1.88 | 90 | 100 | 80 | 30 | 90 | 100 | 90 | 100 | 40 | 100 |
| 1.89 | 90 | 100 | 80 | 70 | 90 | 100 | 100 | 100 | 40 | 100 |
| 1.90 | 90 | 80 | 90 | 80 | 90 | 100 | 100 | 100 | 70 | 100 |
| 1.91 | 90 | 90 | 80 | 40 | 80 | 100 | 100 | 90 | 10 | 100 |
| 1.92 | 80 | 100 | 80 | 80 | 80 | 100 | 100 | 100 | 60 | 100 |
| 1.94 | 90 | 100 | 80 | 60 | 80 | 90 | 100 | 100 | 20 | 100 |
| 1.96 | 80 | 90 | 80 | 80 | 80 | 100 | 100 | 100 | 60 | 100 |
| 1.97 | 50 | 90 | 80 | 80 | 80 | 50 | 90 | 80 | 80 | 80 |
| 1.98 | 40 | 90 | 80 | 70 | 80 | 100 | 100 | 100 | 20 | 100 |
| 1.99 | 70 | 100 | 80 | 30 | 80 | 90 | 100 | 40 | 10 | 90 |
| 1.100 | 80 | 90 | 80 | 40 | 80 | 100 | 100 | 100 | 20 | 100 |
| 1.102 | 60 | 90 | 80 | 60 | 80 | 100 | 100 | 100 | 30 | 90 |
| 1.103 | 90 | 80 | 90 | 70 | 80 | 100 | 80 | 100 | 40 | 100 |
| 1.107 | 100 | 100 | 90 | 50 | 80 | 90 | 100 | 100 | 30 | 100 |
| 1.108 | 90 | 70 | 80 | 20 | 80 | 90 | 80 | 40 | 0 | 70 |
| 2.1 | 90 | 100 | 90 | 90 | 80 | 90 | 90 | 90 | 80 | 90 |
| 2.2 | 100 | 100 | 90 | 70 | 90 | 90 | 70 | 90 | 60 | 90 |
| 2.3 | 90 | 90 | 90 | 20 | 80 | 90 | 90 | 60 | 20 | 80 |
| 2.4 | 90 | 60 | 80 | 60 | 70 | 90 | 90 | 70 | 40 | 90 |

-continued

| Compound | POST Application | | | | | PRE Application | | | | |
|---|---|---|---|---|---|---|---|---|---|---|
| | SOLNI | AMARE | SETFA | ALOMY | ECHCG | SOLNI | AMARE | SETFA | ALOMY | ECHCG |
| 2.6 | 90 | 90 | 70 | 40 | 70 | 90 | 60 | 10 | 20 | 40 |
| 2.7 | 100 | 70 | 70 | 40 | 70 | 100 | 60 | 40 | 30 | 80 |
| 2.8 | 90 | 70 | 90 | 70 | 80 | 90 | 80 | 70 | 30 | 70 |
| 2.9 | 90 | 100 | 90 | 90 | 90 | 90 | 60 | 90 | 60 | 100 |
| 2.10 | 100 | 100 | 90 | 80 | 90 | 90 | 80 | 80 | 50 | 90 |
| 2.11 | 100 | 100 | 90 | 90 | 90 | 100 | 60 | 90 | 40 | 100 |
| 2.12 | 100 | 70 | 90 | 70 | 70 | 90 | 60 | 90 | 80 | 90 |
| 2.13 | 90 | 70 | 90 | 80 | 90 | 100 | 90 | 90 | 60 | 90 |
| 2.14 | 90 | 70 | 90 | 80 | 90 | 90 | 60 | 80 | 40 | 100 |
| 2.15 | 90 | 70 | 90 | 40 | 80 | 90 | 30 | 40 | 10 | 90 |
| 2.16 | 90 | 70 | 90 | 90 | 90 | 90 | 90 | 90 | 60 | 90 |
| 2.17 | 90 | 90 | 90 | 30 | 80 | 80 | 40 | 50 | 10 | 80 |
| 2.18 | 100 | 90 | 100 | 100 | 90 | 100 | 100 | 100 | 100 | 100 |
| 2.19 | 100 | 70 | 100 | 100 | 90 | 100 | 100 | 100 | 100 | 100 |
| 2.20 | 80 | 80 | 70 | 70 | 70 | 100 | 100 | 100 | 100 | 100 |
| 2.21 | 80 | 90 | 80 | 80 | 70 | 100 | 100 | 100 | 90 | 100 |
| 2.22 | 90 | 80 | 80 | 80 | 80 | 100 | 100 | 100 | 100 | 100 |
| 3.1 | 80 | 80 | 80 | 60 | 70 | 100 | 100 | 90 | 60 | 90 |
| 3.4 | 90 | 70 | 90 | 70 | 80 | 100 | 100 | 100 | 70 | 100 |
| 3.5 | 80 | 50 | 70 | 0 | 70 | 60 | 20 | 30 | 0 | 50 |
| 3.10 | 90 | 100 | 90 | 80 | 90 | 100 | 70 | 90 | 70 | 100 |
| 3.11 | 90 | 100 | 90 | 70 | 80 | 100 | 100 | 90 | 70 | 100 |
| 3.13 | 70 | 70 | 80 | 40 | 80 | 80 | — | 80 | 10 | 100 |
| 4.19 | 90 | 70 | 90 | 80 | 80 | 100 | 100 | 100 | 70 | 100 |
| 4.20 | 80 | 100 | 80 | 70 | 80 | 100 | 100 | 100 | 80 | 100 |
| 4.21 | 80 | 90 | 80 | 80 | 80 | 100 | 100 | 100 | 80 | 100 |
| 4.22 | 90 | 90 | 80 | 70 | 90 | 100 | 100 | 100 | 60 | 100 |
| 5.2 | 70 | 90 | 80 | 70 | 80 | 100 | 100 | 100 | 90 | 100 |
| 12.5 | 80 | 80 | 80 | 0 | 80 | 20 | 0 | 60 | 0 | 60 |

The invention claimed is:

1. A herbicidal compound of Formula (Ia) or Formula (Ib)

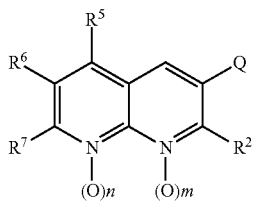

Ia

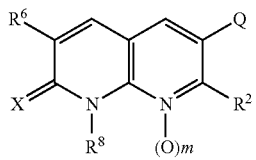

Ib or an agronomically acceptable salt of said compound wherein:

$R^2$ is selected from the group consisting of $C_1$-$C_3$alkyl, $C_1$-$C_3$haloalkyl, $C_1$-$C_3$alkoxy-$C_1$-$C_3$ alkyl, $C_1$-$C_3$-alkoxy-$C_2$-$C_3$alkoxy-$C_1$-$C_3$-alkyl, $C_1$-$C_3$-alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkoxy-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$-alkanesulfonyl-$C_1$-$C_3$-alkylamino)-$C_1$-$C_3$-alkyl and ($C_1$-$C_3$-alkanesulfonyl-$C_3$-$C_4$-cycloalkylamino)-$C_1$-$C_3$-alkyl;

$R^5$ is hydrogen or methyl;

$R^6$ is selected from the group consisting of hydrogen, fluorine, chlorine, hydroxyl and methyl;

$R^7$ is selected from the group consisting of hydrogen, halogen, hydroxyl, sulfhydryl $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_3$-$C_6$alkynyl, $C_1$-$C_6$alkoxy, $C_4$-$C_7$cycloalkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, amino, $C_1$-$C_6$alkylamino, $C_2$-$C_6$dialkylamino, $C_2$-$C_6$alkenylamino, $C_1$-$C_6$alkoxy-$C_1$-$C_6$-alkylamino, ($C_1$-$C_6$-alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino, dialkylamino in which the alkyl groups join to form a 4-6 membered ring optionally containing oxygen and/or optionally substituted by $C_1$-$C_3$-alkoxy and/or halogen, $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$-alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-R', $C_1$-$C_4$alkyleneyl-$CO_2$—R', $C_1$-$C_4$alkyleneyl-(CO)N—R'R', aryl, phenylthio, phenylsulfinyl, phenylsulfonyl, aryloxy and a 5 or 6-membered heteroaryl or heteroaryloxy, the heteroaryl containing one to three heteroatoms, each independently selected from the group consisting of oxygen, nitrogen and sulphur, wherein the aryl or heteroaryl component may be optionally substituted by a substituent selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

X═O or S;

n═0 or 1;

m═0 or 1 with the proviso that if m═1 then n═0 and if n═1 then m═0;

p═0, 1 or 2;

R' is independently selected from the group consisting of hydrogen and $C_1$-$C_6$alkyl;

$R^8$ is selected from the group consisting of hydrogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkylalkenyl, $C_3$-$C_6$alkynylalkylenyl, $C_2$-$C_6$-alkenylalkylenyl, $C_1$-$C_6$alkoxy-$C_1$-$C_6$alkyl, cyano-$C_1$-$C_6$-alkyl, arylcarbonyl-$C_1$-$C_3$-alkyl wherein the arylcarbonyl may be optionally substituted with a substituent selected from the group consisting of halo, $C_1$-$C_3$-alkoxy, $C_1$-$C_3$-alkyl and $C_1$-$C_3$ haloalkyl, aryl-$C_1$-$C_6$alkyl wherein the aryl may be optionally substituted with a substituent selected from the group consisting of halo, $C_1$-$C_3$-alkoxy, $C_1$-$C_3$-alkyl and $C_1$-$C_3$ haloalkyl, $C_1$-$C_6$alkoxy-$C_1$-$C_6$alkoxy-$C_1$-$C_6$alkyl, aryl, 5 or 6-membered heteroaryl-$C_1$-$C_3$-alkyl or heterocyclyl-$C_1$-$C_3$-alkyl, the heteroaryl or heterocyclyl containing one to three heteroatoms each independently selected from the group consisting of oxygen, nitrogen and sulphur, wherein the aryl, heterocyclyl or heteroaryl component may be optionally substituted by a substituent selected from the group consisting of halo, $C_1$-$C_3$alkyl, $C_1$-$C_3$haloalkyl and $C_1$-$C_3$alkoxy;

Q is selected from the group consisting of:—

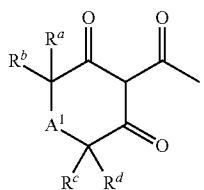
(Q1)

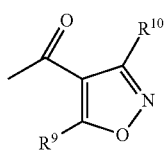
(Q2)

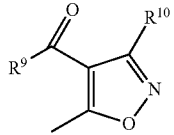
(Q3)

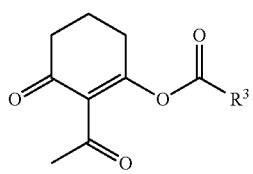
(Q4)

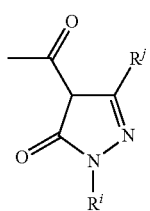
(Q5)

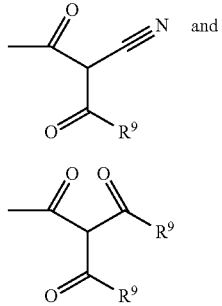
(Q6)

(Q7)

wherein $A^1$ is selected from the group consisting of O, C(O), S, SO, $SO_2$ and $(CR^eR^f)_q$;

q=0, 1 or 2;

$R^a$, $R^b$, $R^c$, $R^d$, $R^e$ and $R^f$ are each independently selected from the group consisting of $C_1$-$C_4$alkyl which may be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl and heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, wherein the substituents on the nitrogen in the heterocyclic ring are other than halogen; or $R^a$, $R^b$, $R^c$, $R^d$, $R^e$ and $R^f$ are each independently selected from the group consisting of hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by substituents selected from the group consisting of $C_1$-$C_4$alkoxy, halogen, hydroxy, cyano, hydroxycarbonyl, $C_1$-$C_4$alkoxycarbonyl, $C_1$-$C_4$alkylsulfonyl and $C_1$-$C_4$haloalkyl, the substituents on a nitrogen in the heterocyclic ring are other than halogen; or $R^a$ and $R^b$ together form a 3- to 5-membered carbocyclic ring which may be substituted by $C_1$-$C_4$alkyl and may be interrupted by oxygen, sulfur, S(O), $SO_2$, OC(O), $NR^g$ or by C(O); or $R^a$ and $R^c$ together form a $C_1$-$C_3$alkylene chain which may be interrupted by oxygen, sulfur, SO, $SO_2$, OC(O), $NR^h$ or by C(O); it being possible for that $C_1$-$C_3$alkylene chain in turn to be substituted by $C_1$-$C_4$alkyl;

$R^g$ and $R^h$ are each independently of the other $C_1$-$C_4$alkyl, $C_1$-$C_4$haloalkyl, $C_1$-$C_4$alkylsulfonyl, $C_1$-$C_4$alkylcarbonyl or $C_1$-$C_4$alkoxycarbonyl;

$R^i$ is $C_1$-$C_4$alkyl;

$R^j$ is selected from the group consisting of hydrogen, $C_1$-$C_4$ alkyl and $C_3$-$C_6$ cycloalkyl;

$R^3$ is selected from the group consisting of $C_1$-$C_6$alkyl, optionally substituted with halogen and/or $C_1$-$C_3$alkoxy and $C_3$-$C_6$ cycloalkyl optionally substituted with halogen and/or $C_1$-$C_3$alkoxy;

$R^9$ is selected from the group consisting of cyclopropyl, $CF_3$ and isopropyl;

$R^{10}$ is selected from the group consisting of hydrogen, I, Br, $SR^{11}$, $S(O)R^{11}$, $S(O)_2R^{11}$ and $CO_2R^{11}$;

$R^{11}$ is $C_{1-4}$ alkyl.

2. A herbicidal compound according to claim 1 having Formula Iaa

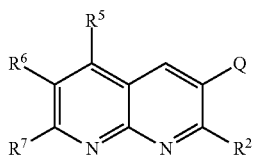

Iaa

3. A herbicidal compound according to claim 1, wherein Q is Q1.

4. A herbicidal compound according to claim 3, wherein $A^1$ is $CR^eR^f$ and wherein $R^a$, $R^b$, $R^c$, $R^d$, $R^e$ and $R^f$ are hydrogen and wherein q=1.

5. A herbicidal compound of claim 1, wherein $R^2$ is fluoroalkyl or $C_{1-3}$alkoxy-$C_{1-3}$-haloalkyl.

6. A herbicidal compound according to claim 5, wherein $R^2$ is trifluoromethyl.

7. A herbicidal compound according to claim 1, wherein $R^6$ is hydrogen or fluorine.

8. A herbicidal compound according to claim 1, wherein $R^7$ is selected from the group consisting of hydrogen, hydroxyl, halogen, $C_1$-$C_6$alkyl, $C_1$-$C_6$ haloalkyl, $C_1$-$C_6$ alkoxy, $C_1$-$C_6$ alkoxy-$C_2$-$C_6$-alkoxy, $C_1$-$C_6$-alkoxy-$C_1$-$C_6$ alkyl and $C_1$-$C_6$-alkoxy-$C_2$-$C_6$-alkoxy-$C_1$-$C_6$ alkyl.

9. A herbicidal compound according to claim 1, wherein $R^7$ is selected from the group consisting of hydrogen, methyl, ethyl, 1-methylethyl, cyclopropyl, 1-chloroethyl, 1,1-dichloroethyl, fluoromethyl, difluoromethyl, trifluoromethyl, 1-fluoroethyl, 1,1-difluoroethyl, 2,2-difluoroethyl, 1-fluoro-1-methylethyl, 2,2,2-trifluoroethyl, difluorochloromethyl, methoxy, ethoxy, methoxymethyl, methoxyethyl, ethoxyethoxy, ethoxyethoxymethyl, methoxyethoxy and methoxyethoxymethyl, (2-methoxyethyl)amino and (2-methoxyethyl)methylamino.

10. An agronomically acceptable salt of the compound according to claim 1, wherein the salt is selected from the group consisting of $Na^+$, $Mg^{2+}$ and $Ca^{2+}$.

11. A herbicidal composition comprising a herbicidal compound according to claim 1 and an agriculturally acceptable formulation adjuvant.

12. A herbicidal composition according to claim 11, further comprising at least one additional pesticide.

13. A herbicidal composition according to claim 12, wherein the additional pesticide is a herbicide or herbicide safener.

14. A method of selectively controlling weeds at a locus comprising crop plants and weeds, wherein the method comprises application to the locus of a weed controlling amount of a composition according to claim 11.

15. A method of making a compound of Formula (Ia) or (Ib) wherein Q=Q1 which comprises reacting together a compound of Formula (Ia') or (Ib')

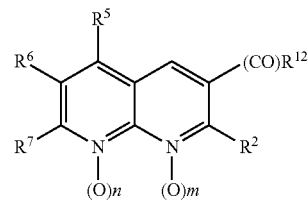

Ia'

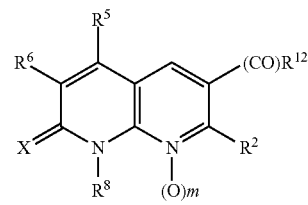

Ib' wherein the various substituents are as defined in claim 1, and wherein $R^{12}$ is halogen or aryloxy with a compound of Formula (II)

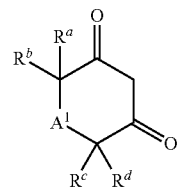

(II)

wherein the various substituents are as defined in claim 1, in the presence of an inert organic solvent and a base.

* * * * *